United States Patent [19]

Hull et al.

[11] Patent Number: 4,941,746
[45] Date of Patent: Jul. 17, 1990

[54] APPARATUS FOR AUTOMATICALLY DETERMINING THE DENSITIES OF A GRAPHIC IMAGE

[75] Inventors: Frank A. Hull, Circle Pines, Minn.; H. Brent Archer, Miami, Fla.; Curt Frederick, Blaine, Minn.

[73] Assignee: Chesley F. Carlson Company, Plymouth, Minn.

[21] Appl. No.: 132,521

[22] Filed: Dec. 14, 1987

Related U.S. Application Data

[63] Continuation-in-part of Ser. No. 51,270, May 4, 1987, abandoned, which is a continuation of Ser. No. 722,907, Apr. 12, 1983, abandoned.

[51] Int. Cl.$^5$ .............................................. C01N 21/00
[52] U.S. Cl. ..................................... 356/444; 364/525
[58] Field of Search ............... 356/444, 445, 448, 429, 356/447, 380, 379; 364/525

[56] References Cited

U.S. PATENT DOCUMENTS

| | | | |
|---|---|---|---|
| 3,765,778 | 10/1973 | Bey et al. | 356/223 |
| 4,003,660 | 1/1977 | Christie et al. | 356/429 |
| 4,180,741 | 12/1979 | Palmatier et al. | 356/444 |
| 4,187,435 | 2/1980 | Palmatier et al. | 356/444 |
| 4,441,819 | 4/1984 | Takeuchi et al. | 356/380 |
| 4,512,662 | 4/1985 | Tobias | 356/380 |
| 4,609,291 | 9/1986 | Takahashi | 356/418 |
| 4,666,306 | 5/1987 | Matsumoto | 356/444 |

Primary Examiner—Richard A. Rosenberger
Attorney, Agent, or Firm—Dorsey & Whitney

[57] ABSTRACT

An automatic scanning densitometer which is self calibrating and accurately measures highlight density, shadow density and tonal distribution of midtones occurring in the subject matter of the photograph to be reproduced. A reflection densitometer is disclosed which in one or more scans identifies and measures first the highlight and shadow densities and the tonal distribution of the subject matter to be reproduced, as opposed to the background of the photo. The instrument automatically determines the size of the original and, with an input to the device, the size of the window in which the original is to be reproduced to provide enlargement or reduction. Measurement of density values are uniquely stabilized and with the use of a monolithic sensor on a single substrate the entire image is processed and measured, not just target areas which must be manually measured or aligned with an apertured scanning bar. Using plant press data as an input to the system, all values for a near perfect reproduction are rapidly displayed by the device and can be printed or can be used as an input for an exposure computer to automate the graphic arts reproduction process.

19 Claims, 64 Drawing Sheets

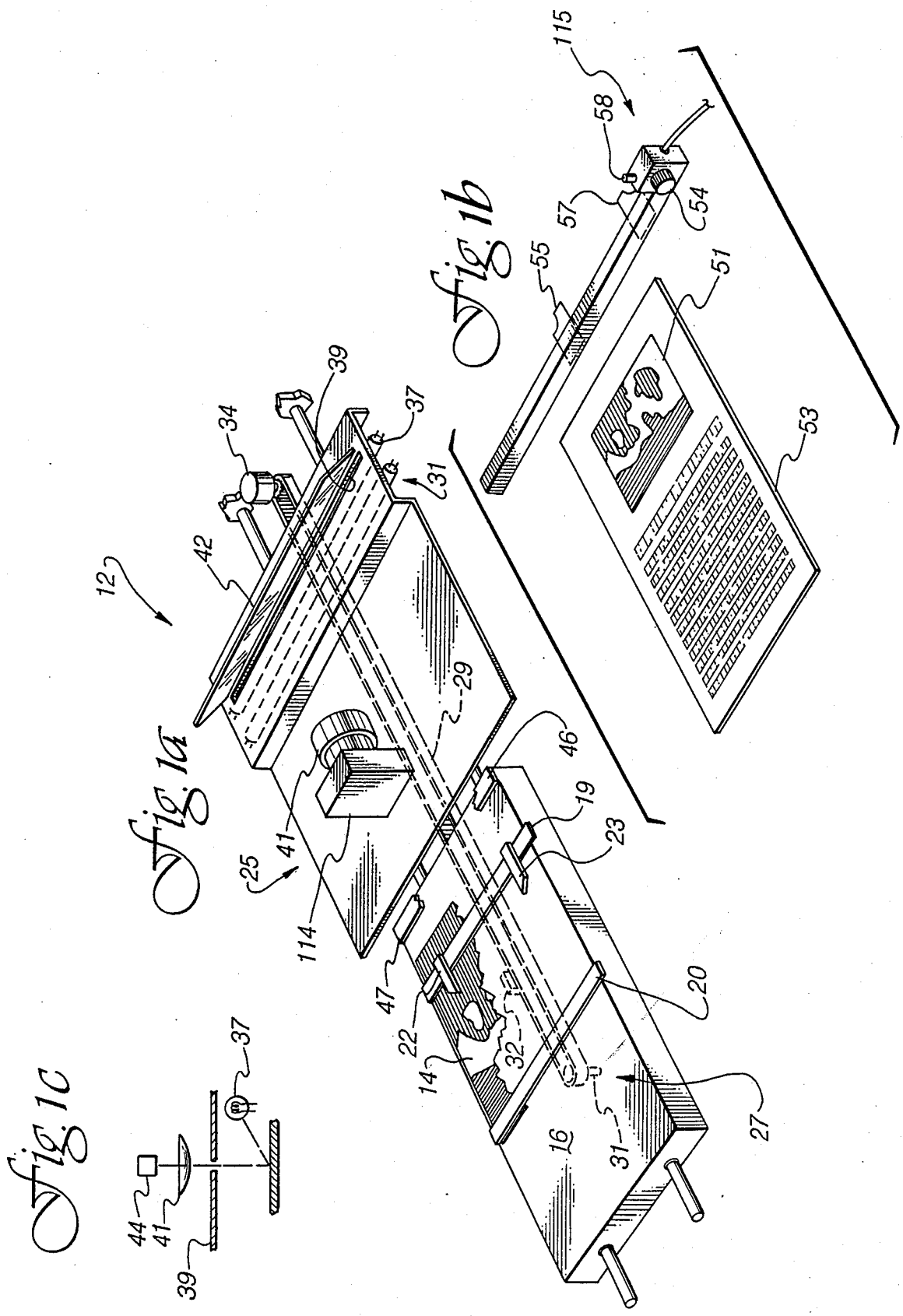

Fig. 3

| FIG.3a | FIG.3b | FIG.3c |
|---|---|---|

Fig. 4

| FIG.4a | FIG.4d |
|---|---|
| FIG.4b | FIG.4e |
| FIG.4c | FIG.4f |

Fig. 5a

| FIG.5a-1 | FIG.5a-2 | FIG.5a-3 | FIG.5a-4 | FIG.5a-5 | FIG.5a-6 |
|---|---|---|---|---|---|
| FIG.5a-7 | FIG.5a-8 | FIG.5a-9 | FIG.5a-10 | FIG.5a-11 | |

Fig. 5c

| FIG.5c-1 | FIG.5c-2 |
|---|---|

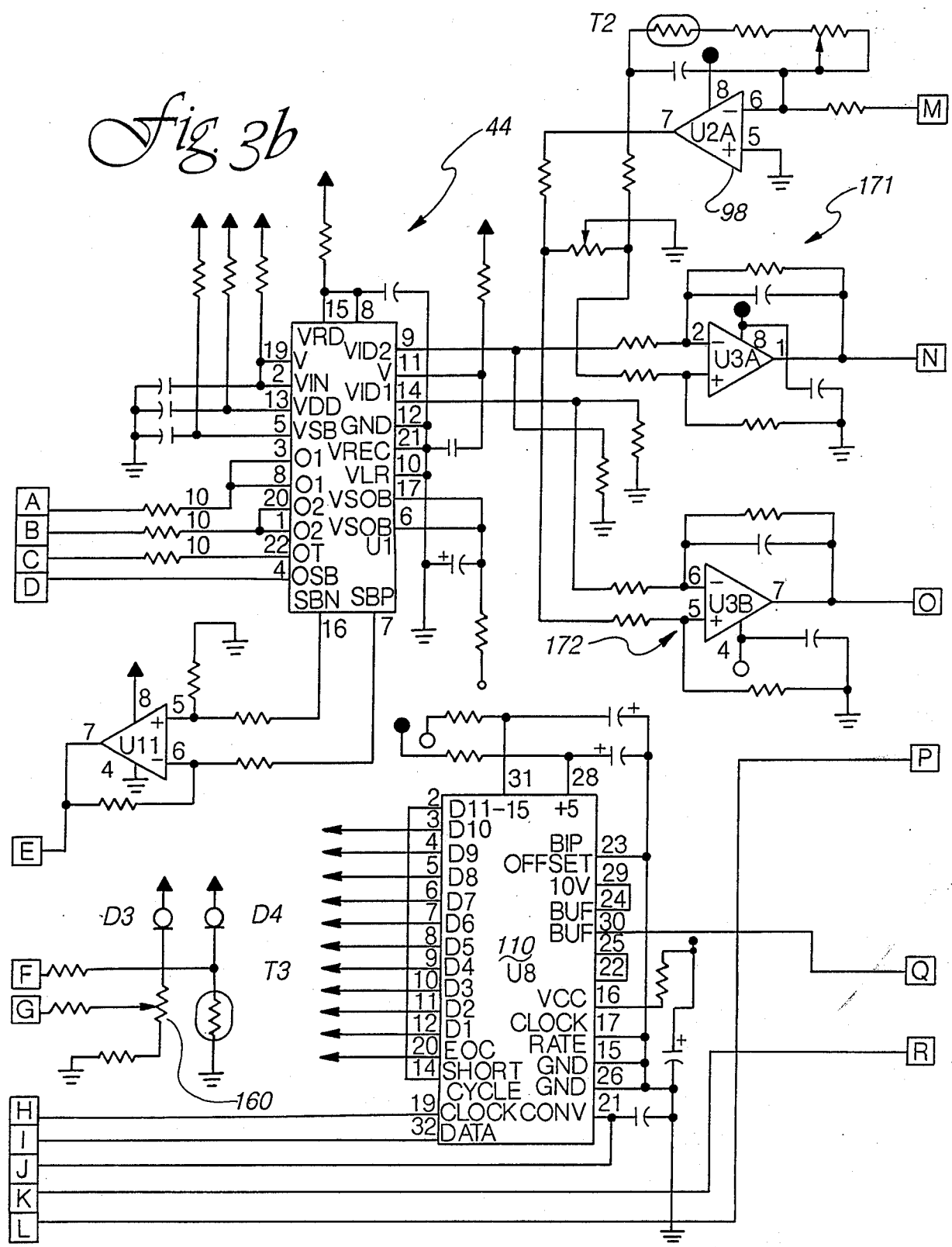

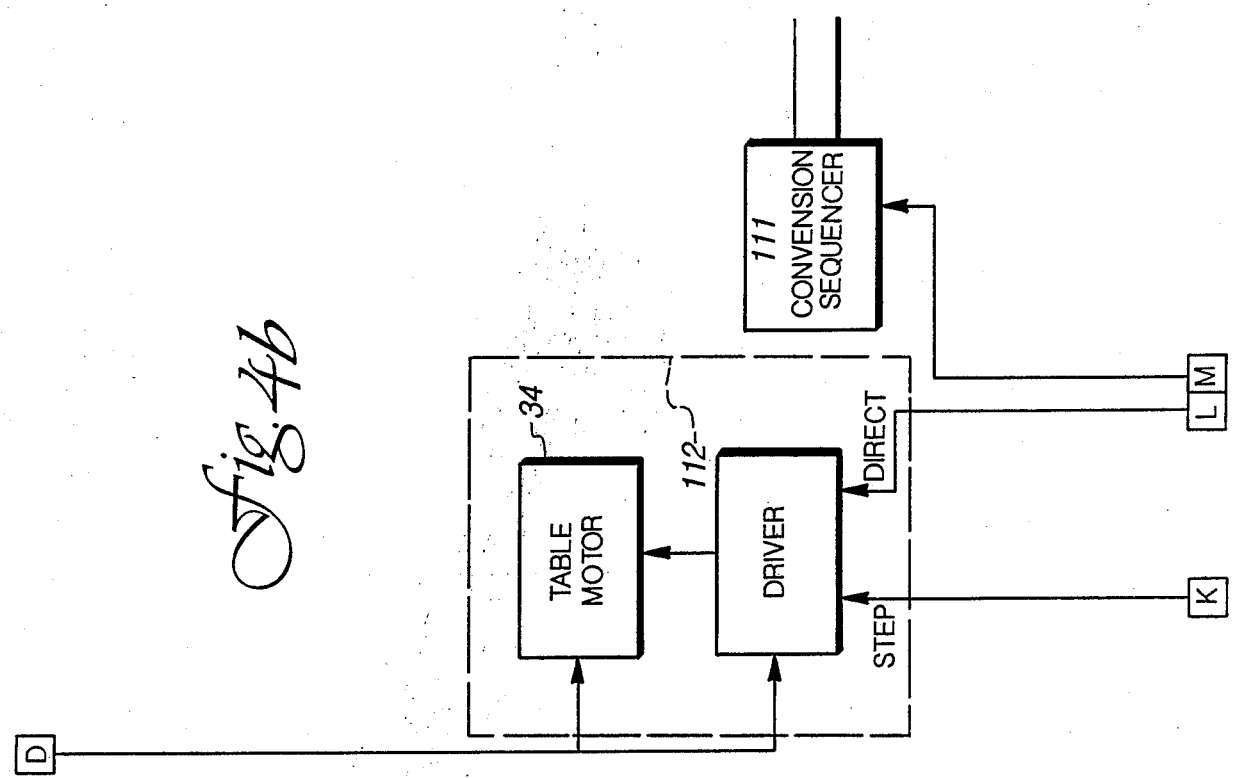
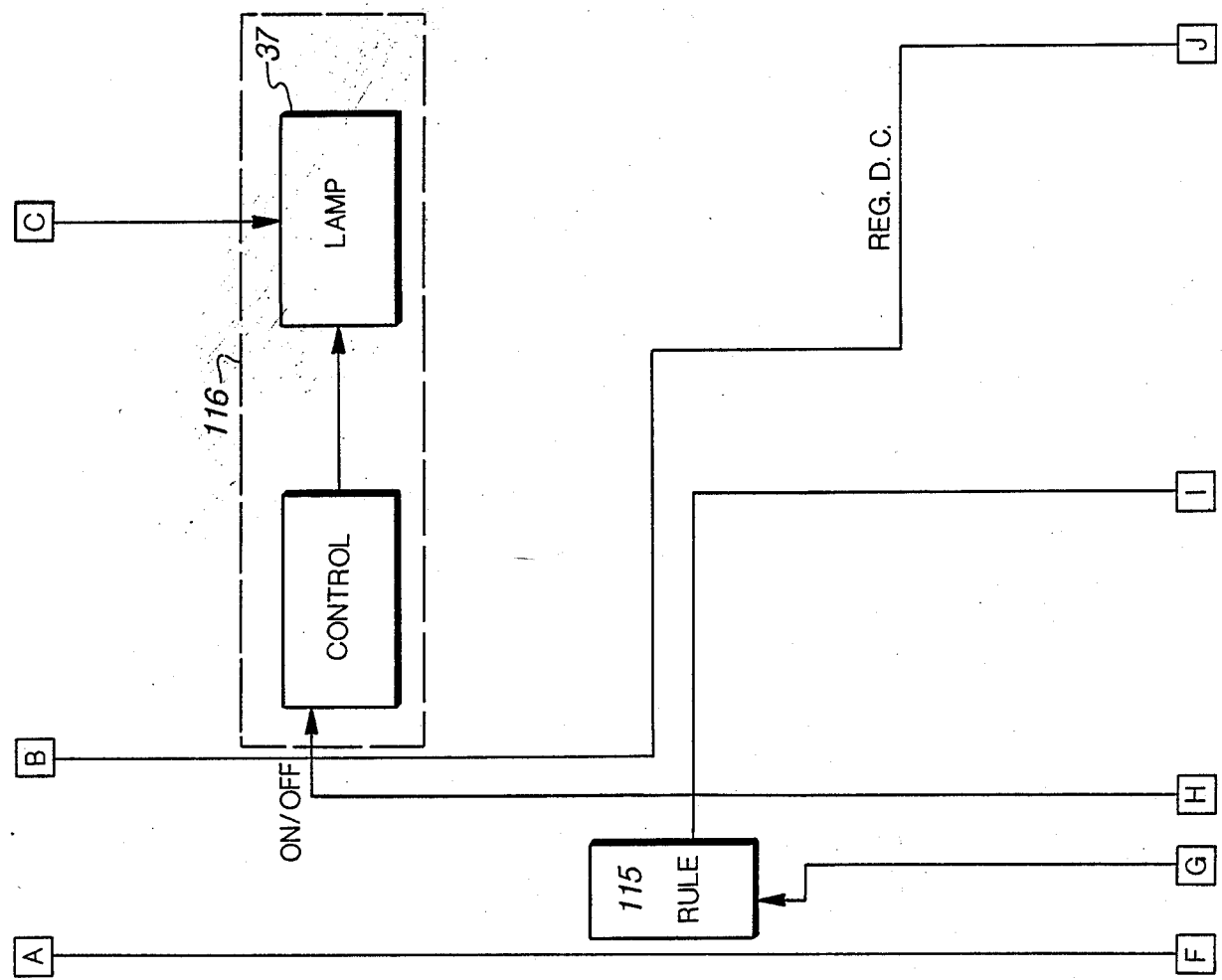
Fig. 4b

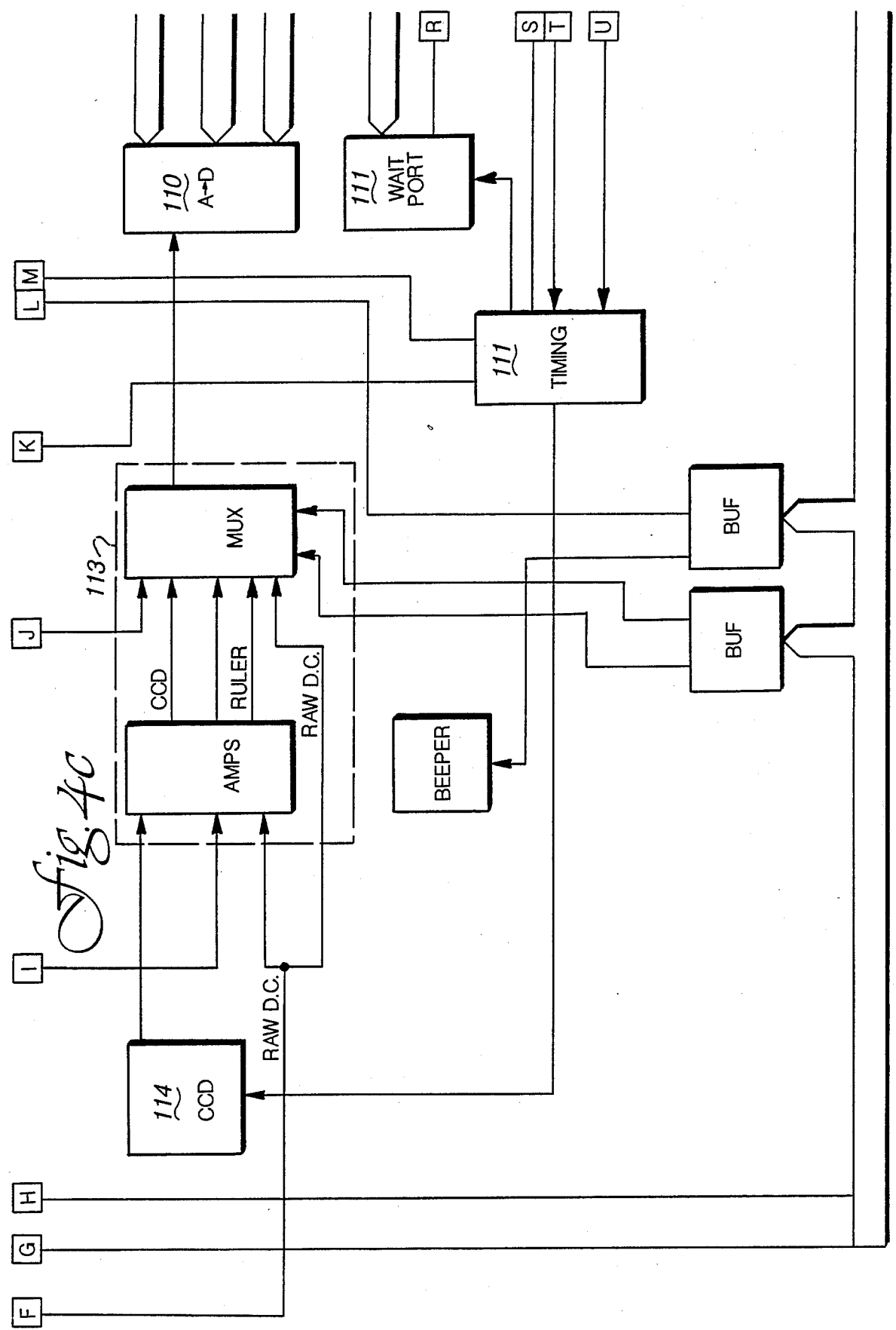

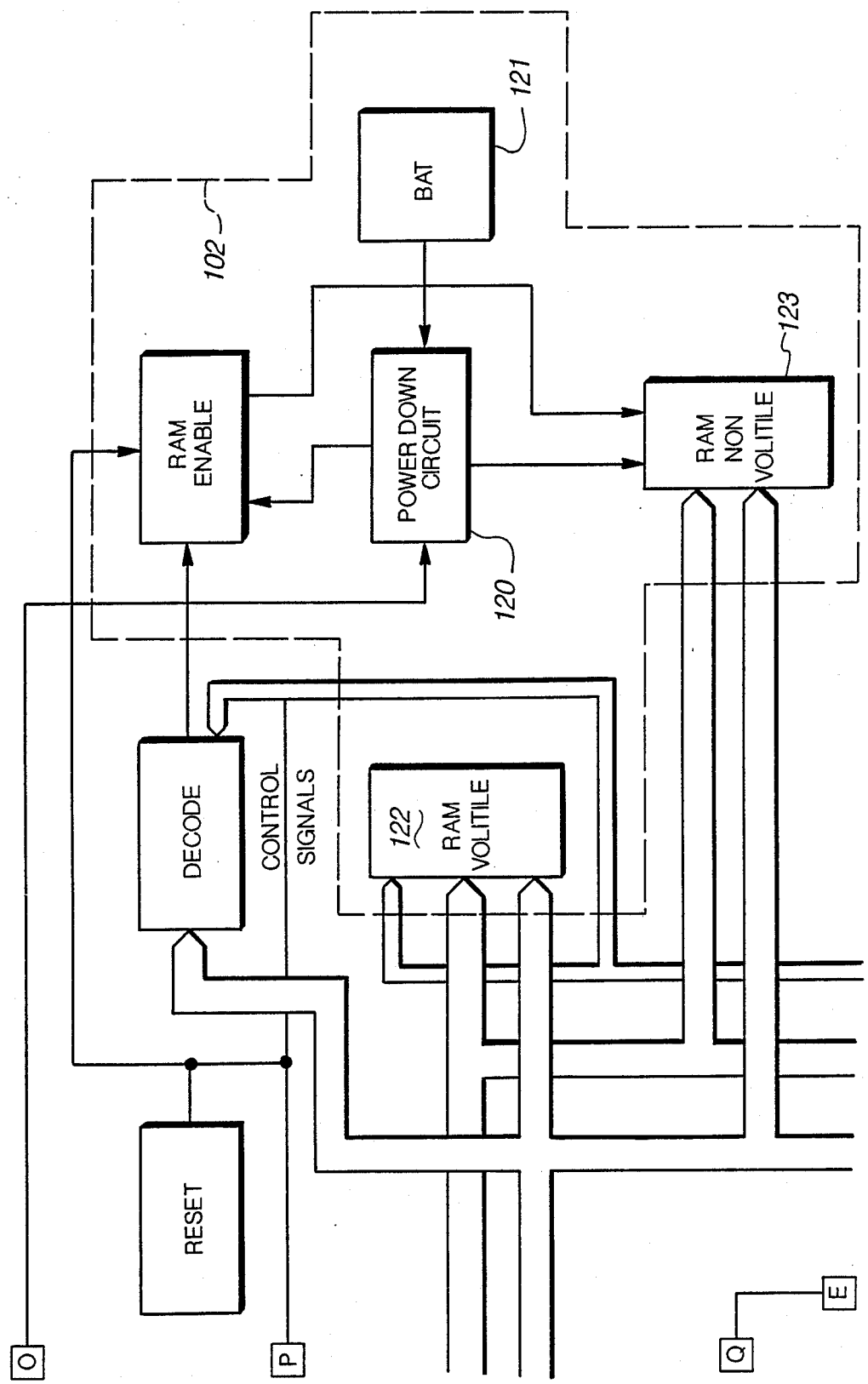

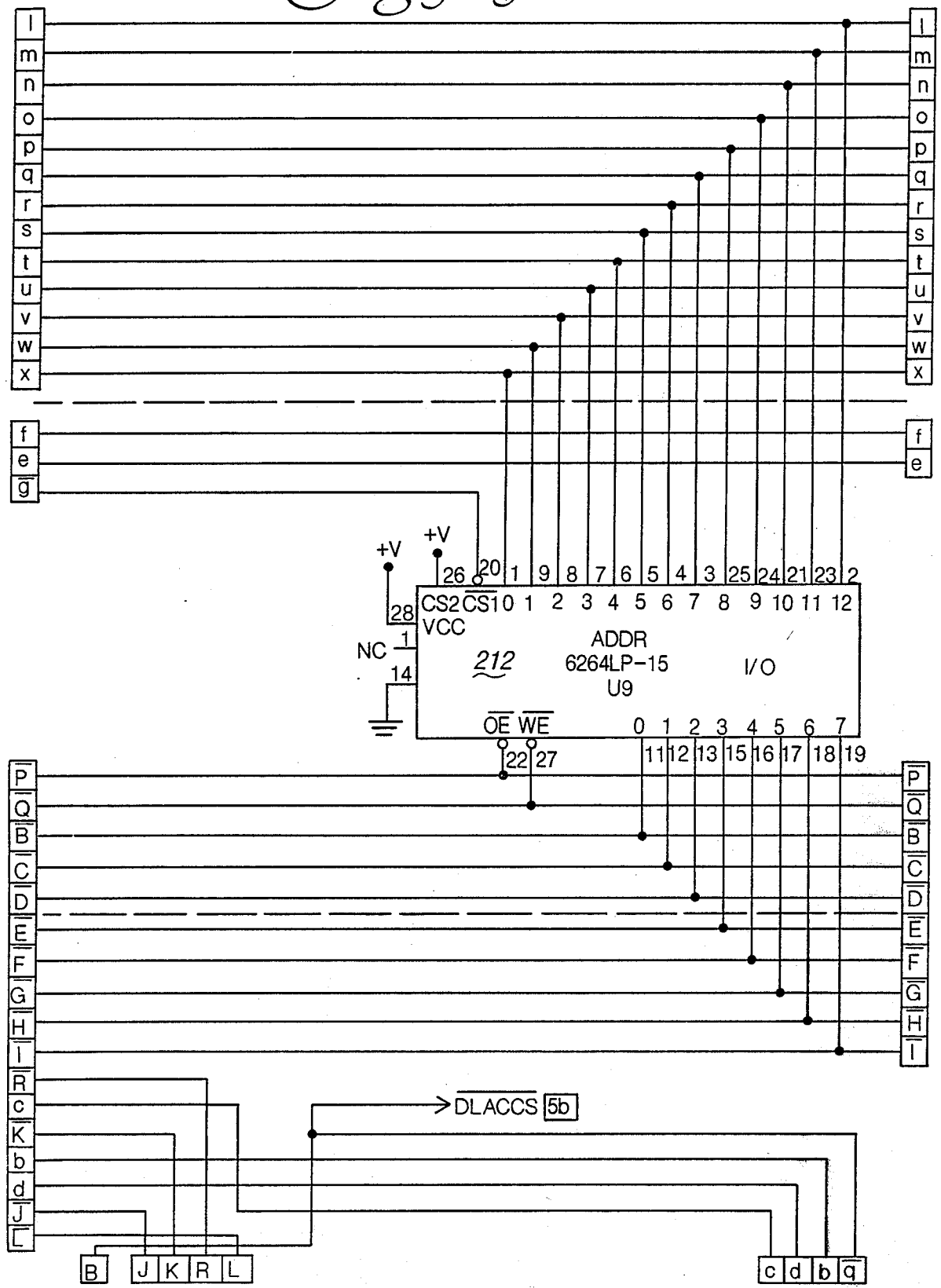

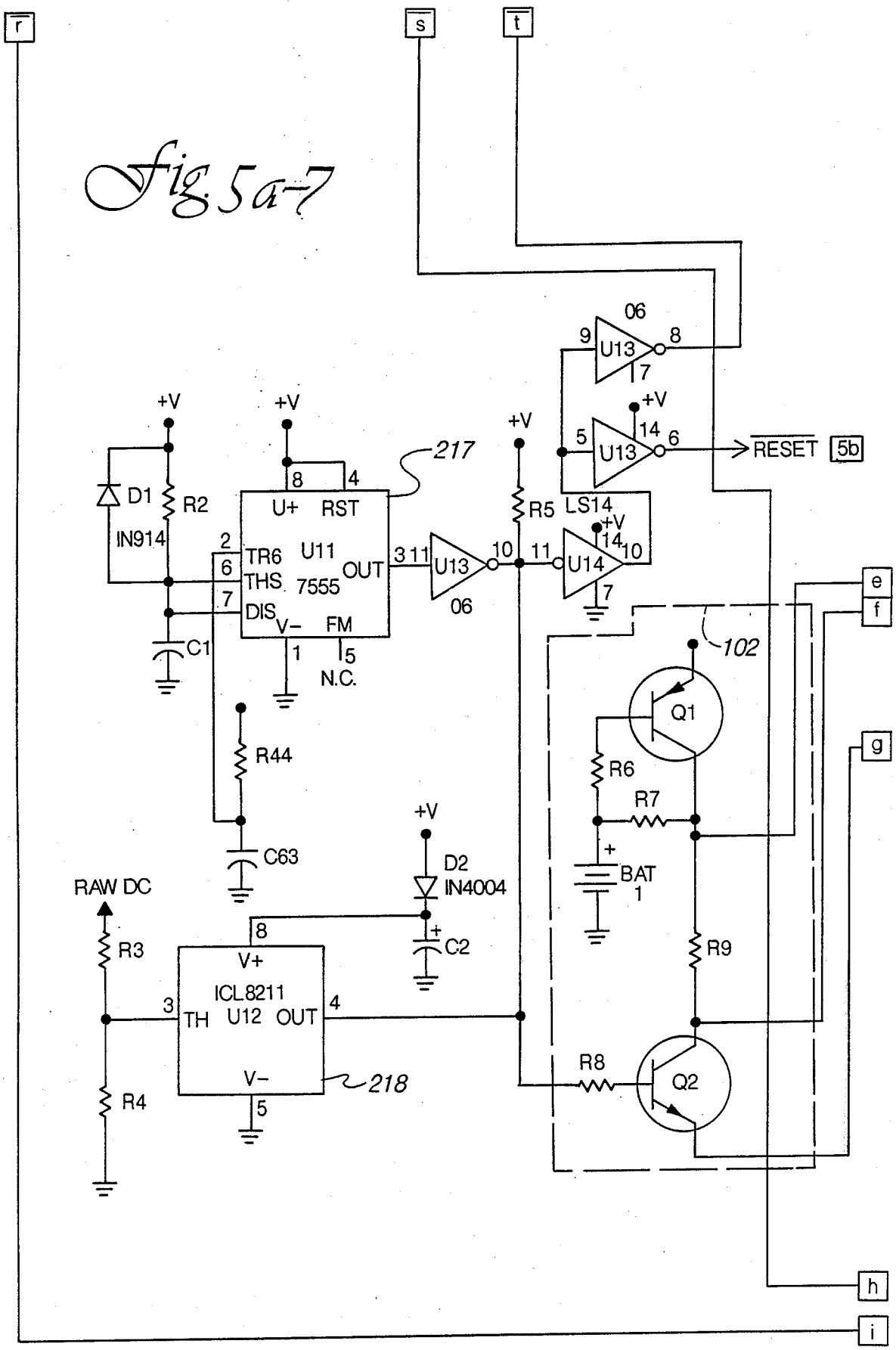

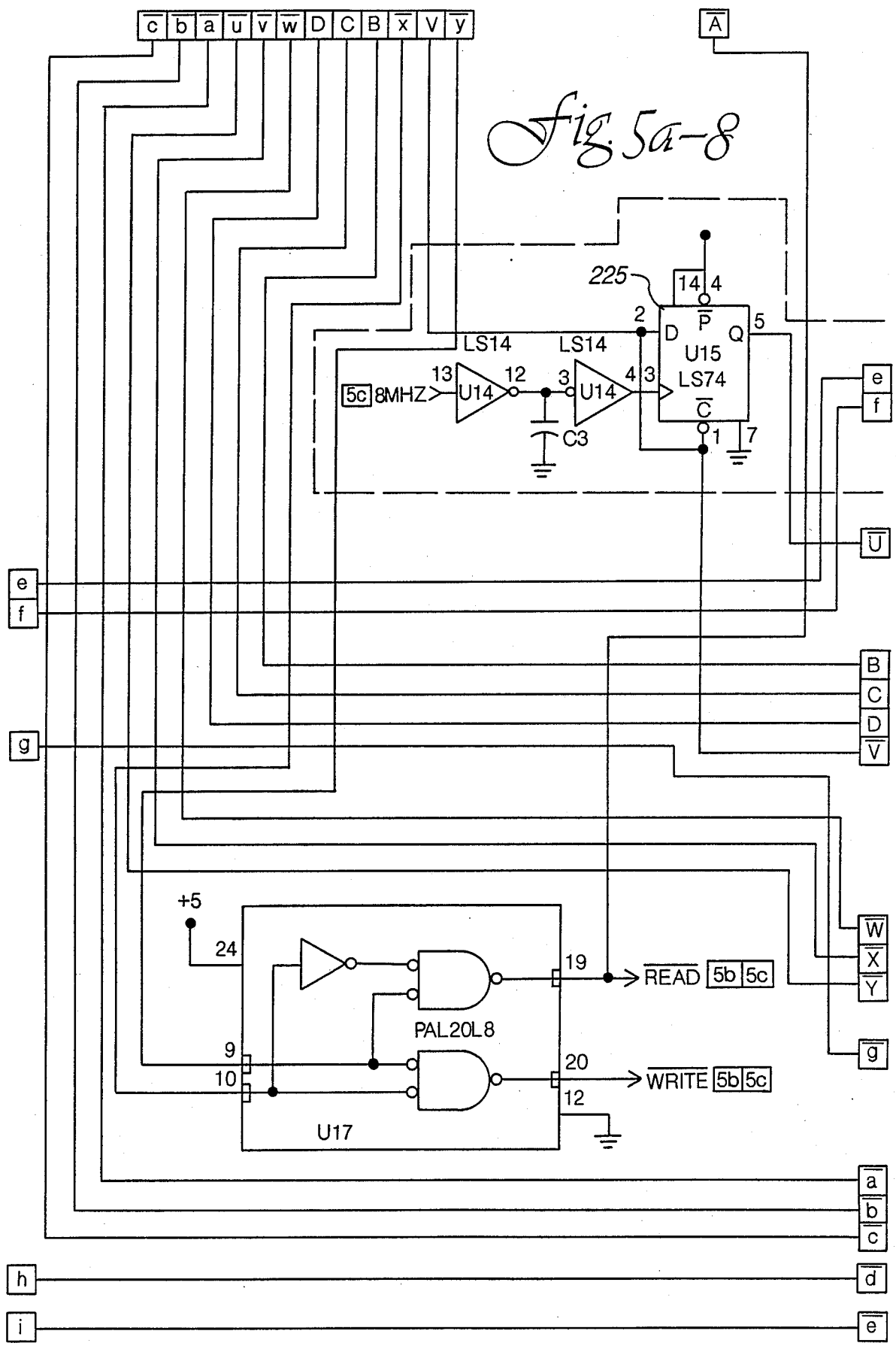

fig. 5b

| FIG.5b-1 | FIG.5b-2 | FIG.5b-3 |
|---|---|---|
| FIG.5b-4 | FIG.5b-5 | FIG.5b-6 |
| FIG.5b-7 | FIG.5b-8 | FIG.5b-9 | fig. 5d

| FIG.5d-1 | FIG.5d-2 | FIG.5d-3 | FIG.5d-4 |
|---|---|---|---|
| FIG.5d-5 | FIG.5d-6 | FIG.5d-7 | FIG.5d-8 | fig. 5e

| FIG.5e-1 | FIG.5e-2 | FIG.5e-3 | FIG.5e-4 |
|---|---|---|---|

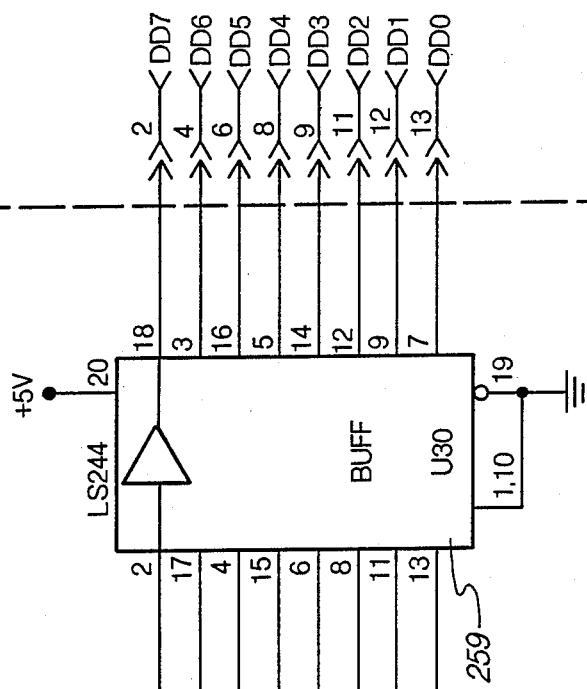
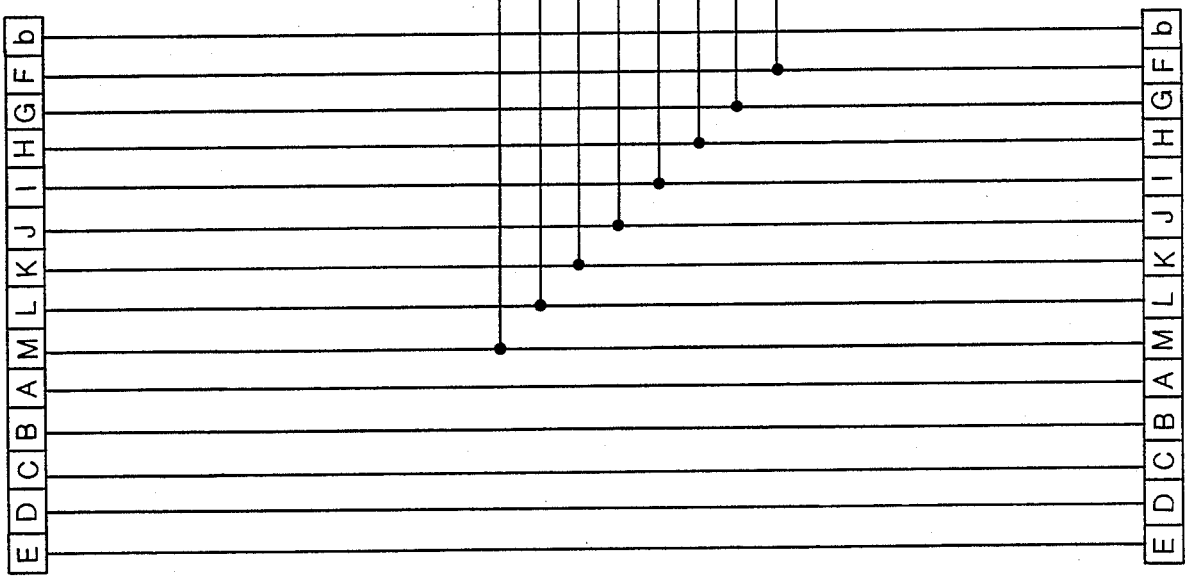
Fig 5b-6

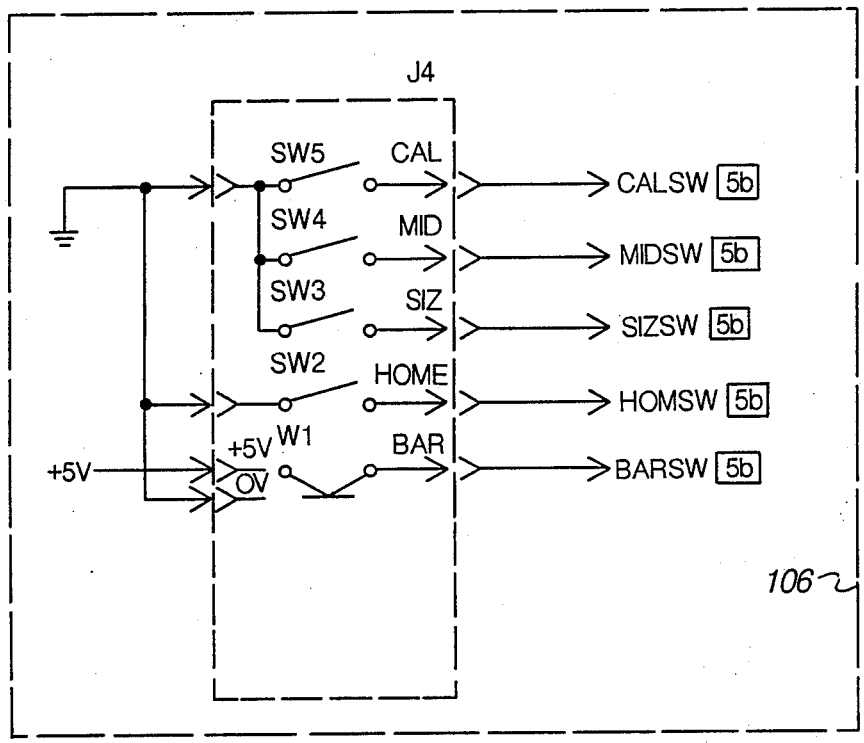
fig. 5d-5
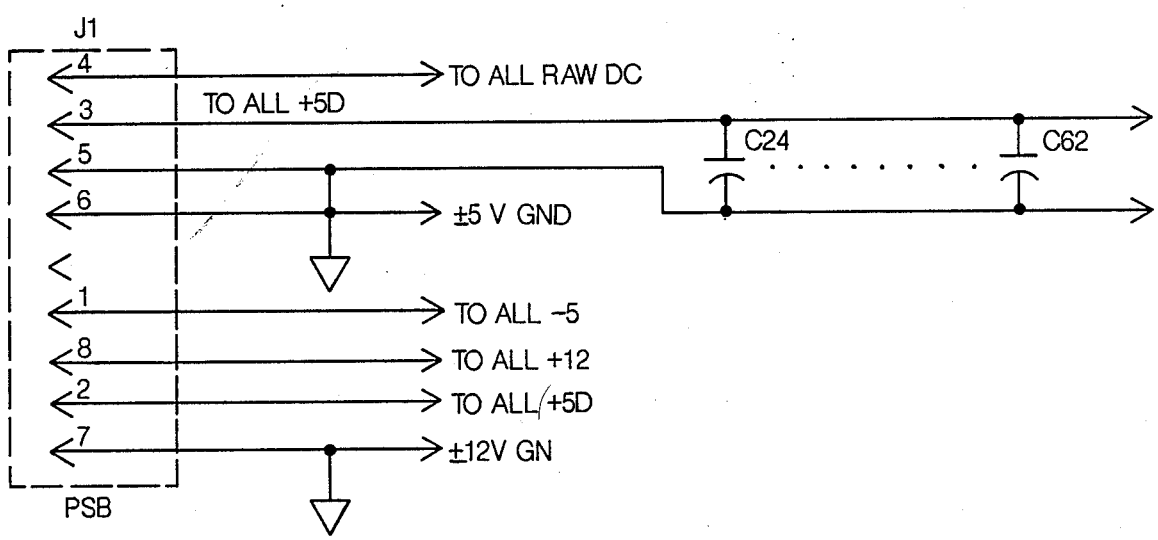

| | |
|---|---|
| UR1 | 7905 |
| UR2 | 7812 |
| UR3 | 7912 |
| U1 | SAA1027 |
| U2 | ULN2003 |
| UR4 & UR5 | 78H051 |

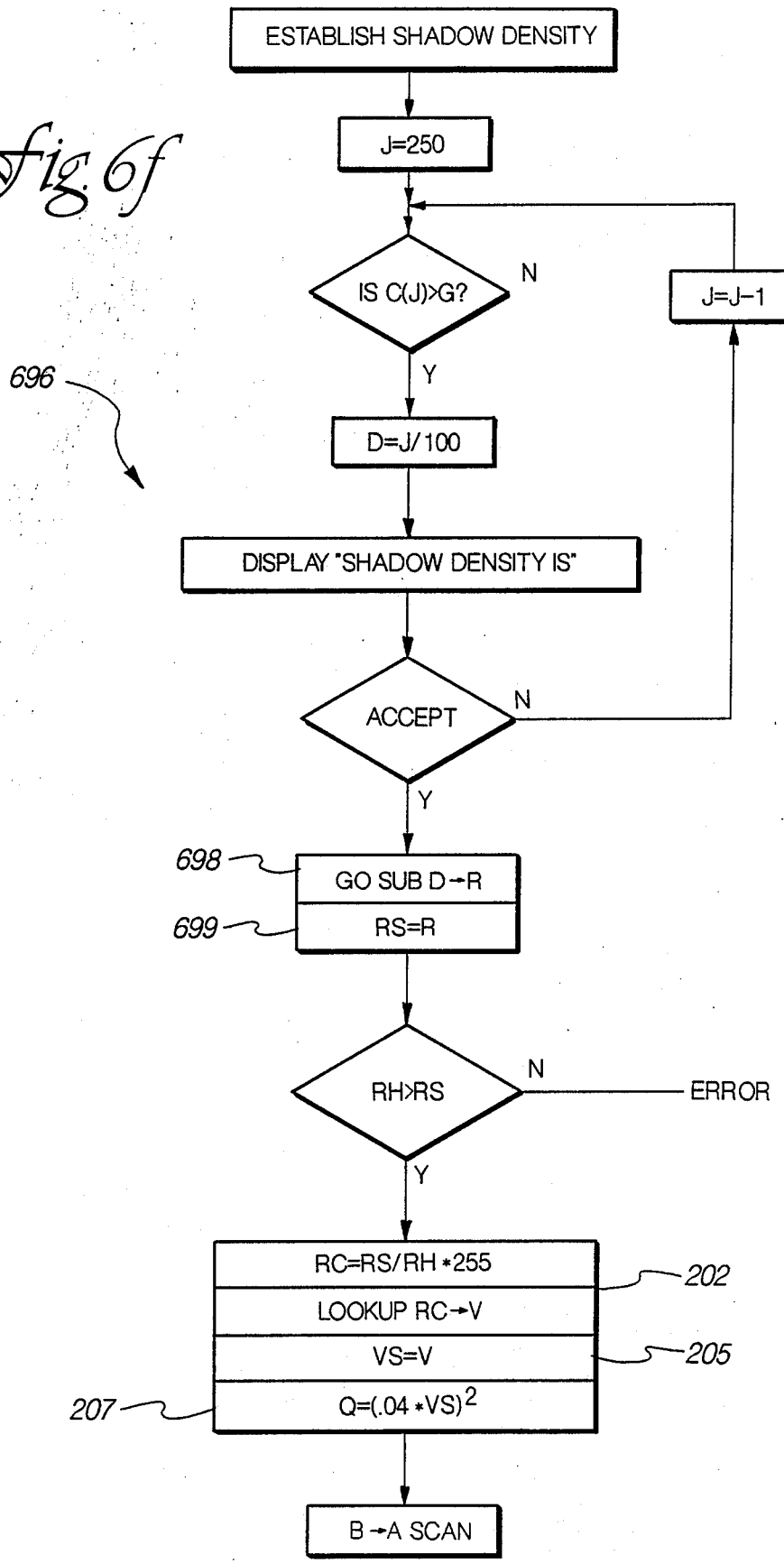

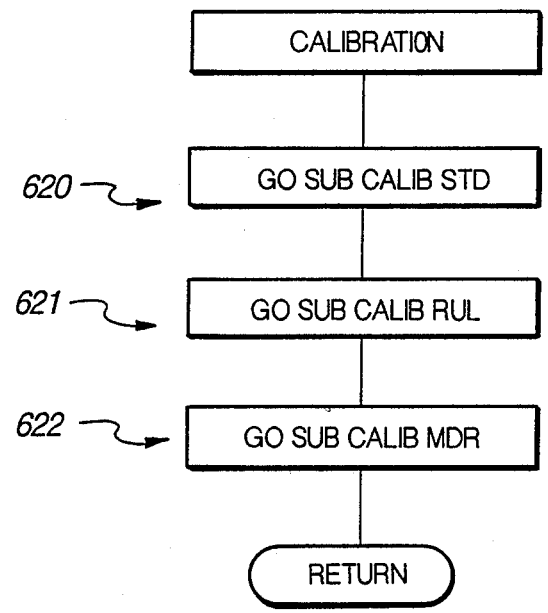
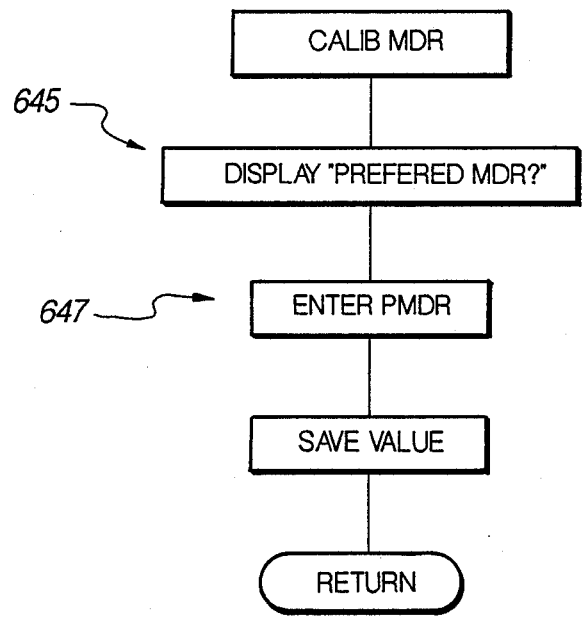
fig. 61

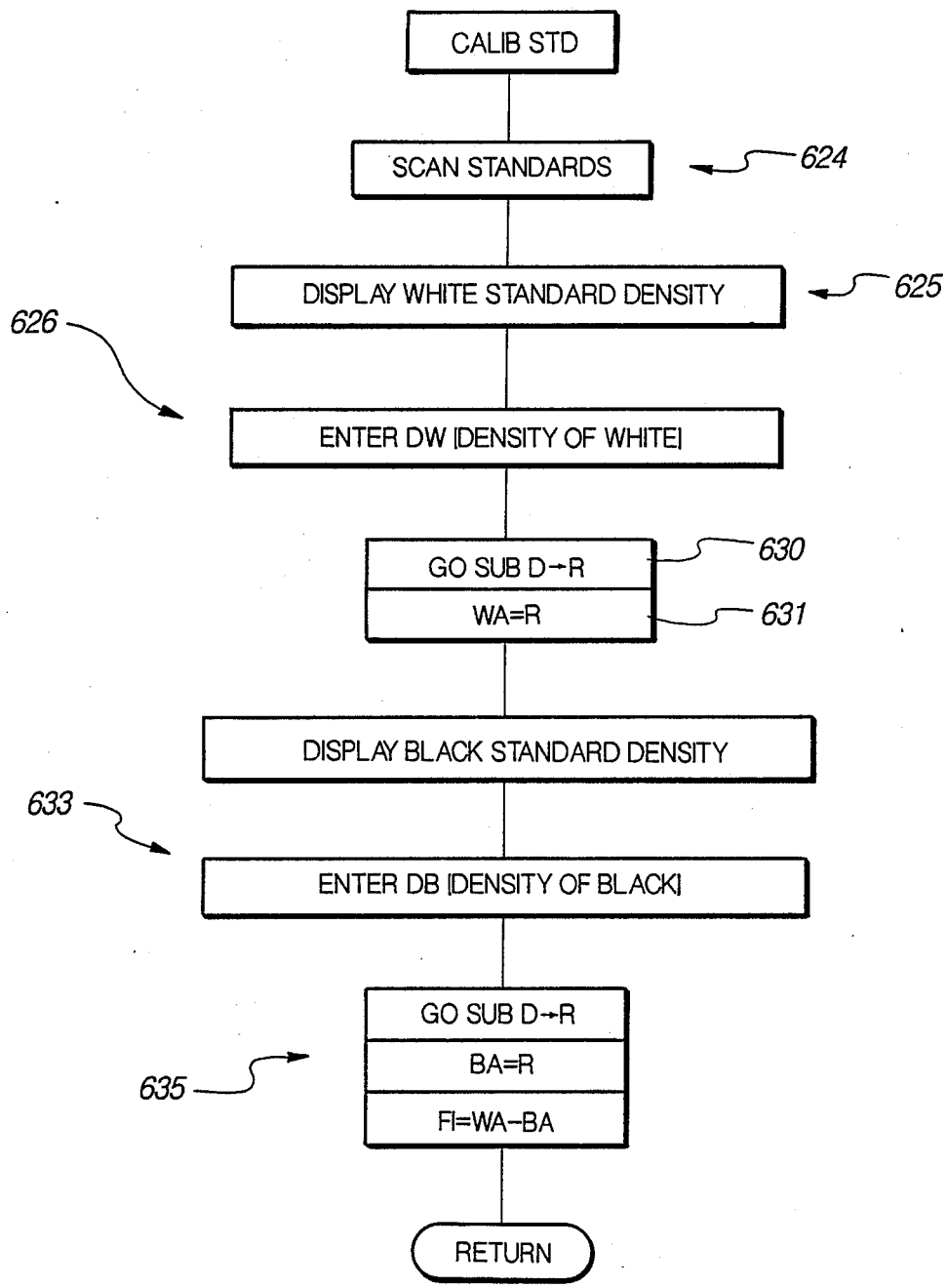

APPARATUS FOR AUTOMATICALLY DETERMINING THE DENSITIES OF A GRAPHIC IMAGE

RELATED APPLICATIONS

This application is a continuation-in-part of application Ser. No. 51,270, filed May 4, 1987, now abandoned which was a continuation of application Serial No. 722,907, filed April 12, 1985.

BACKGROUND OF THE INVENTION

The invention relates to densitometers used in graphic arts to determine highlight, shadow and midtone densities necessary to reproduce photographs and similar graphic images with printing presses.

Procedures used in the past have been very labor intensive with painstaking attention being required to determine the criteria for reproduction of a graphic image. In the past, an individual technician knowledgeable in the art had to make a subjective determination of the brightest portion of a graphic image to be reproduced and of the darkest portion of a graphic image to be reproduced and, with a hand held densitometer, measure as precisely as he could position the densitometer the highlight density and the shadow density of the brightest and darkest portion of the graphic image. The determination of the tonal distribution, where to place the midtone dots, was even more subjective, variable from individual to individual.

Limited attempts at automating the Graphic Arts processes have been proposed. For example, gross measurements of the amount of light passed through a transparency has been proposed to determine the amount of ink required, on a per column basis, for offset printing. Using an appertured scanning bar, having discrete devices fixed in the apertures, data was obtained on a per column basis to determine how much of the image was dark or clear. This data was then used to supply the correct amount of ink which corresponded to the amount of image which was to be printed. The necessary alignment of the discrete devices through the apertures with targeted highlight and shadow densities, and other problems inherent in such a design, suggests that such a system would not be practical to make the density determinations which are achieved with the present invention.

Current technology lends itself to automation of the prior art processes. However, non-uniformity of light sensitive or light measuring devices and the problems of calibration and drift of such devices has been an obstacle to such automation. In addition, with hand held instruments positioned for a period of time the intensity of light could be regarded as uniform. At microprocessor based speeds, however, the fluctuating line voltage and cyclical nature of light becomes a problem which had to be overcome to automate densitometry. Finally, with a high resolution system, with measurement accuracy in the one to three millimeter range, methods had to be devised to accumulate and evaluate the volume of raw data that is obtained with an automated procedure.

Because of the magnitude of the problems involved in automating densitometry the manual method of locating the tonal distribution from highlight densities to shadow densities is the method that is in common use today.

SUMMARY OF THE INVENTION

The scanning densitometer of the present invention effectively, precisely and automatically scans and measures an entire graphic image in one millimeter portions; accurately converting the measurements into densities in the range of zero to 2.7 for reflection densitometry; and can accommodate a density range of zero to four for transmission densitometry. The invention evaluates the data obtained to indicate the highlight density and shadow density of the graphic image, rejecting noise in the process. In addition, the system effectively ignores redundant densities signifying background and accurately accumulates midtone densities to indicate the tonal distribution of the actual subject of the graphic image. With an input based on the printing presses used in the plant in which the graphic image is going to be reproduced, a near perfect reproduction can be obtained.

The scanning densitometer is designed to use a monolithic gate shifted charge coupled device (CCD) array or charge coupled photodiode (CPD) array of approximately 256, 512 or 1024 diodes, integrated on a single chip, past which the graphic image can be scanned in both directions. Using a known white bar and a known black bar each cell in the array is calibrated for each scan. The scanning output of each cell is then corrected with the data obtained during the calibration to assure uniformity of measurement between cells and between different scans of different images.

Measurements are synchronized with the line frequency which drives the light to assure accuracy of results.

In a first high resolution scan highlight and shadow densities are accumulated and, after a preselected number of highlight (brightness) readings and shadow (darkness) readings are obtained, the highlight and shadow density of the copy is calculated.

On a return low resolution scan midtones are identified and, with the use of a memory device, are accumulated in a pixel map of the graphic image. It is preferred that an analysis of the pixel map be done automatically in which redundant pixels having approximately the same density are ignored as background and a tonal distribution of the subject matter of the graphic image without the background is produced. The tonal distribution can then accommodate the particular condition of the printing presses that are to run the reproduction, lighter copy for newsprint, darker copy for more heavily coated media, to produce a near perfect reproduction.

It is an object of the invention to automatically scan an entire graphic image for purposes of reproduction.

It is an object of the invention to use a monolithic sensing element so that the densities and tonal distribution of the entire image can be measured and analyzed in detail.

It is an object of the invention to automatically determine highlight and shadow densities of an image to be reproduced.

It is an object of the invention to automatically determine the tonal distribution of the midtones of a graphic image.

It is an object of the invention to automatically determine the criteria of reproduction of the graphic image.

These and other objects and advantages of the invention will be apparent to those skilled in the art upon a review of the following description of the preferred embodiment and the accompanying drawings and claims.

DESCRIPTION OF THE DRAWINGS

FIG. 1a is a perspective view of the invention, with the frame removed, showing the scanning table or platen upon which the copy is placed with the light sensitive array and scanning head overlying the platen. FIG. 1b is a perspective view of the electronic ruler used to measure the width of the window into which the graphic image is to be reproduced. FIG. 1c is a schematic elevational diagram of the light source lens and diode array when used as a reflection densitometer.

DESCRIPTION OF THE PREFERRED EMBODIMENT

Figures 1, 5A:
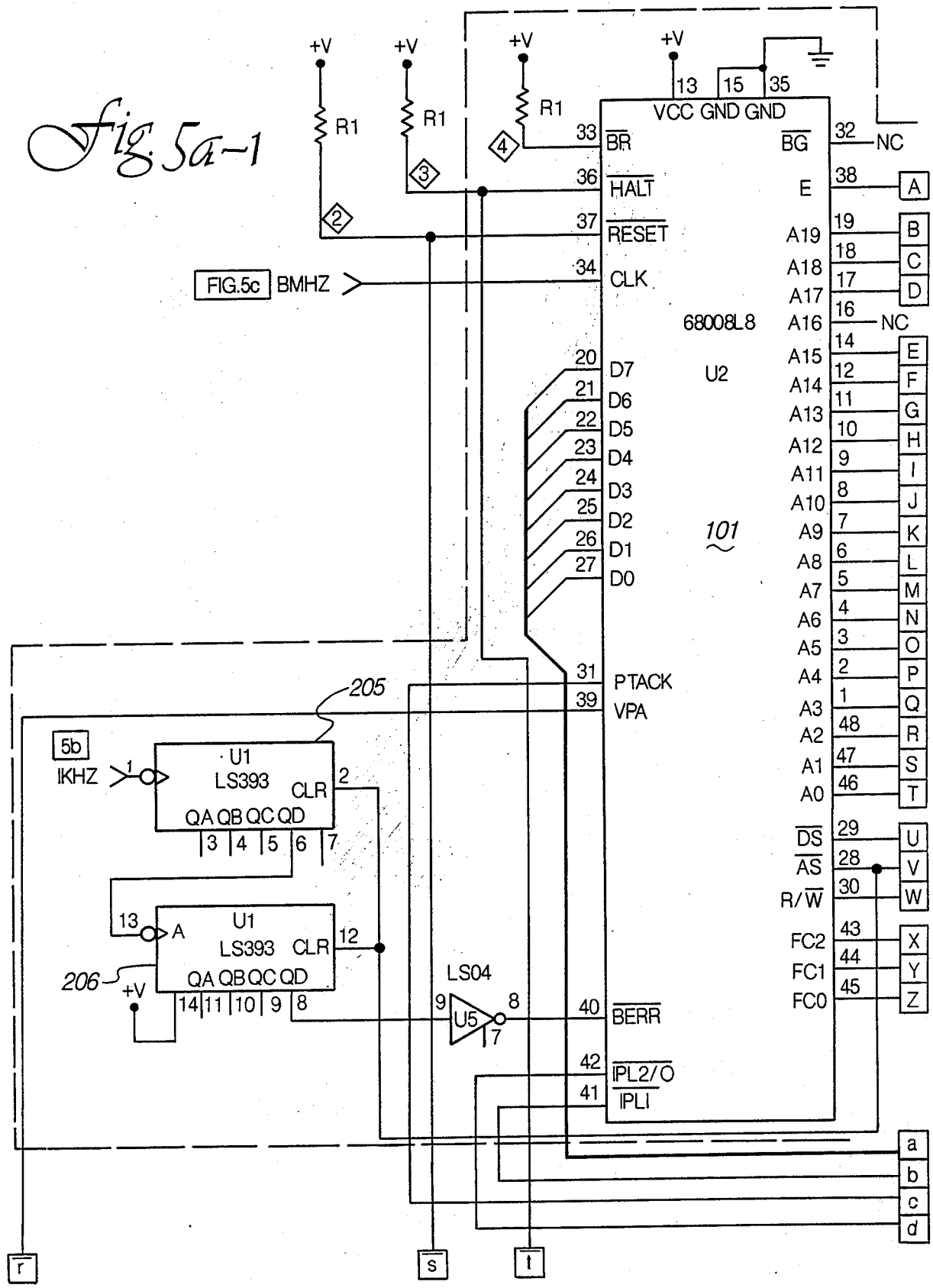
FIG. 1 shows a perspective view of the physical layout of the invention.
Figures 2, 5A:
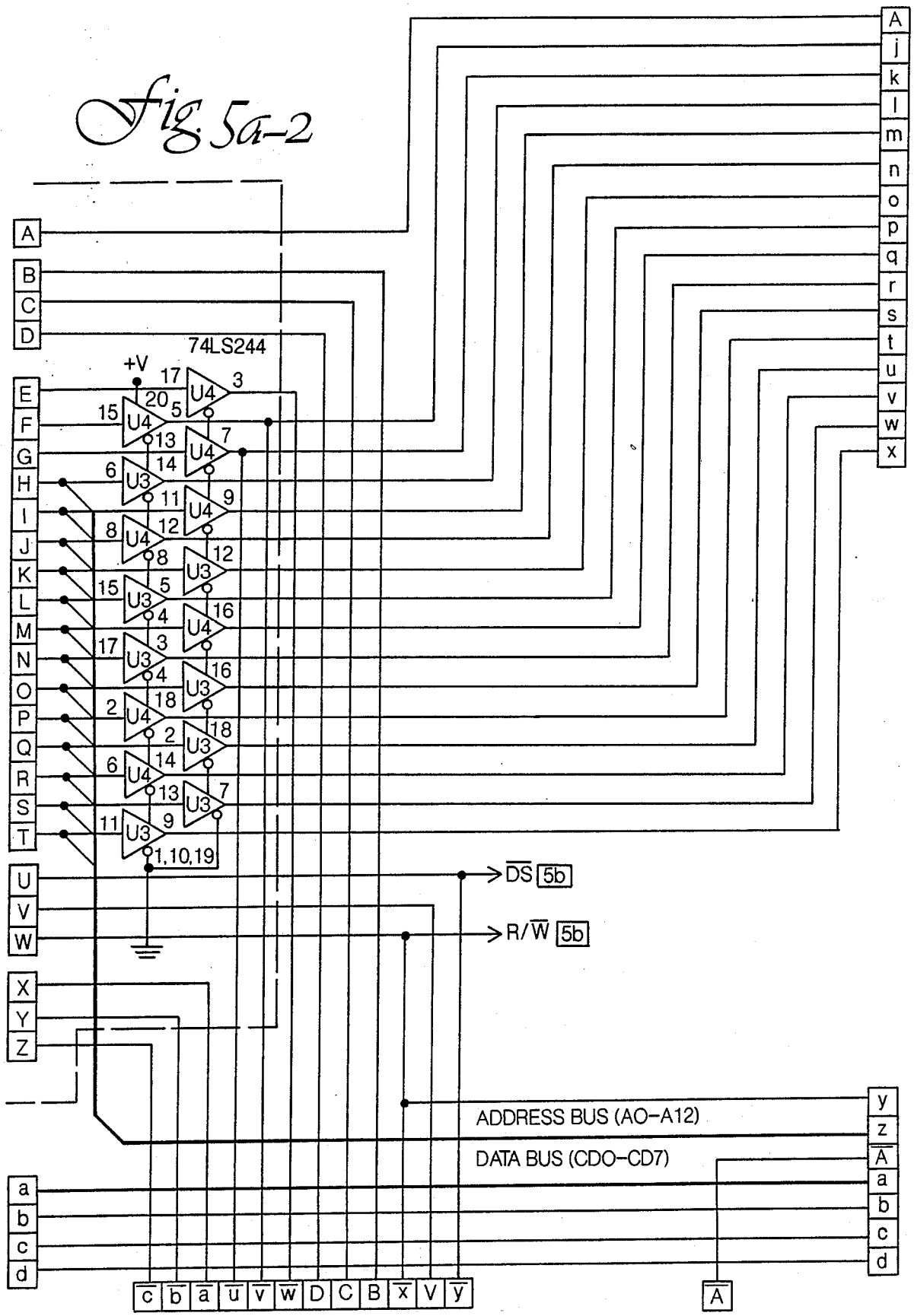
FIG. 5, consisting of FIGS. 5a-5e, together with either 2b or 3, a schematic diagram of the electronics of the invention.
Figures 3, 5A:
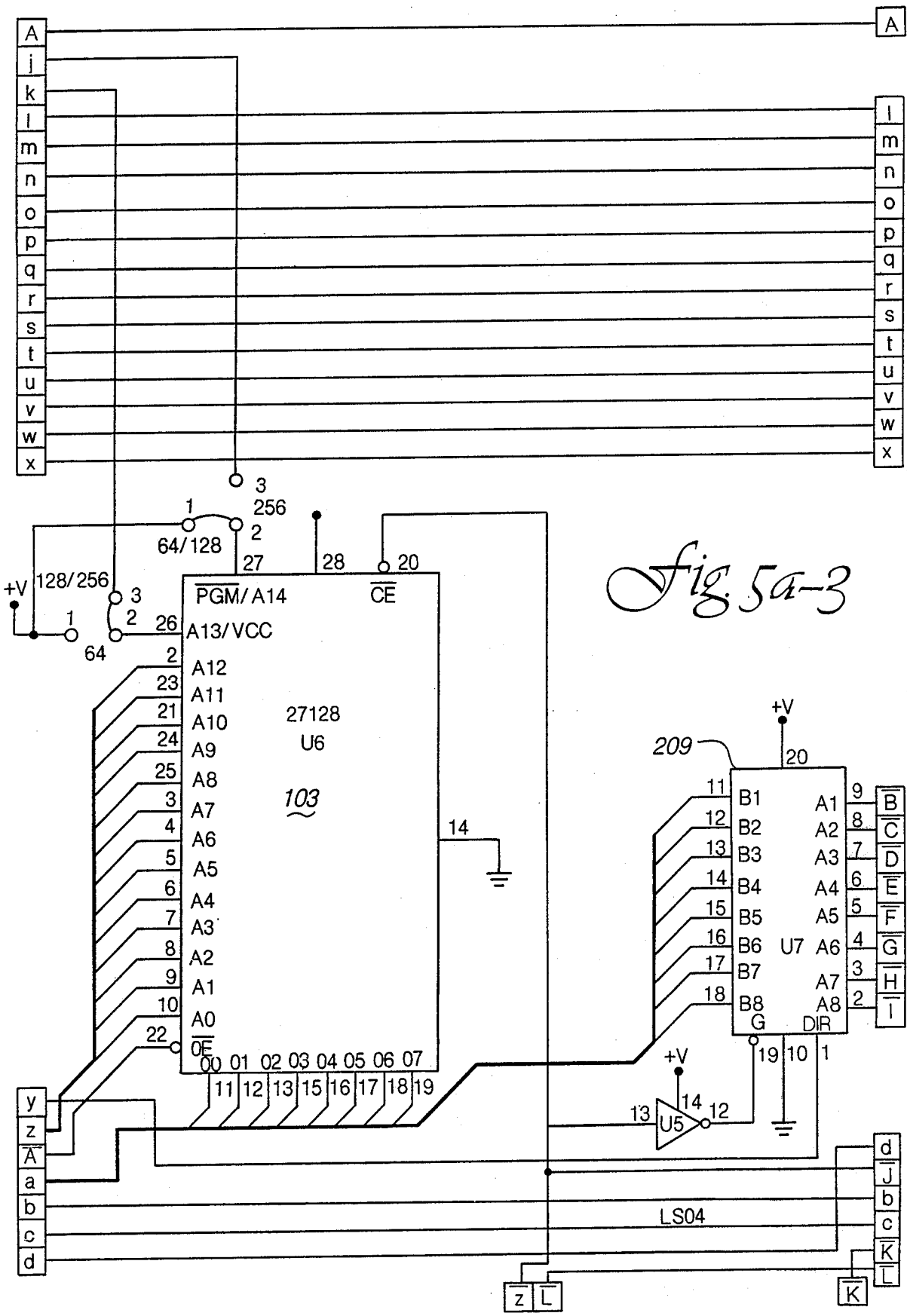

Shown in FIG. 1 is a representation of a reflection densitometer 12 employing the invention. The graphic image 14 to be evaluated, shown partly broken away, is placed on the work table or platen 16 and framed with two reflective bars 19 and 20 which are cropping bars and two sliding reflective tabs 22, 23 which can be detected by the densitometer to determine the size of the work 14 to be reproduced. The work table 14 is advanced under the scanning head 25 by a tractor feed 27 consisting of a belt 29, with a belt idler 31 and a belt 32 to bed connector 32 which is advanced by a stepper motor 34, the speed of which is controlled by the densitometer microprocessor 101. The scanning head 25, a diagramatic sketch of which is included as FIG. c, consists of one or more mercury argon 4000 volt cold cathode lamps 37 which are directed toward the copy 14 and reflect off of the copy 14 through a slit 39. With the use of a four millimeter C-mount lens 41 and a reflective mirror 42 the light is focused on a monolithic array 44, a layout of which and associated circuitry for a charge coupled device array (CCD) is shown in FIG. 2. A similar circuit with temperature compensation for a charged coupled photodiode array (CPD) is shown in FIG. 3.

A monolithic array, all light sensitive elements integrated on a single chip, is utilized to get complete coverage and analysis of the image. This maximizes the information retrieved and enables the accuracy of the invention to be achieved. The graphic image 14 being scanned can be scanned twice upon each operation of the scanning densitometer 12. An A to B scan when the graphic image 14 is first passed under the scanning head 12 can be a high resolution scan which accumulates the detected densities and the frequency of occurrence of each density. From this data the highlight density (brighest portion of the graphic image) and the shadow density (darkest portion of the graphic image) can be determined. A measured highlight density or shadow density should occur a preselected number of times before it is considered valid data. In this way, imperfections of the image 14, noise or other errant operation of the densitometer can be rejected and will not create false data.

During a reverse scan, B to A, which can be at twice the speed of the initial scan or at the same speed, the output of adjacent cells 44 can be averaged to produce a low resolution pixel map of the graphic image 14. This pixel map can be stored in memory 102 and analyzed by software, to be discussed in conjunction with FIG. 6, to create a tonal distribution of the subject of the graphic image 14. This evaluation rejects redundant densities, signifying background portions of the image 14, and accumulates only those midtone densities which form the subject of the graphic image 14. In this way an accurate reproduction of the graphic image 14 can be reproduced.

Prior to each scan the densitometer 12 is calibrated to compensate for non-uniformity of the individual diodes in the array 44 and to compensate for drift. This is accomplished with a black bar 47 and a white bar 46 which underlie the scanning head 25, each having a known reflectance which creates an initial standard. The calibrated white and calibrated black for each cell is stored in memory 102 and the measured white and measured black from each cell when scanning the image is corrected by the calibration standard to provide uniformity of data.

Accumulation of densities, the frequency of occurrence of each midtone density, as determined from the pixel map can be compared with the plant operating condition, that is, the type of presses upon which the reproduction is to be run and the type of paper upon which the reproduction is to be run. For example, for a plant running newsprint a typical plant condition would run the reproduction at approximately 0.7 MDR. The intersection of this value with the tonal distribution curve of any given image produces the operating specification for the exposure computer (not shown) which is to create the half tone reproduction for the presses.

As shown in FIG. 1b, an electronic ruler 115 can also be used to measure the window 51 in the copy 53 for which the reproduction is to be run. The electronic ruler 115 consists of a variable potentiometer 54, which is used to detect the position of a movable pointer 55 on one side of the window 51, and a read button 55 which, when depressed, creates an interrupt to the microprocessor processor 101 to indicate that the automatic ruler 115 is ready to be read for an automated determination of the distance between the movable pointer 55 and a fixed pointer 57.

Figures 4, 5A:
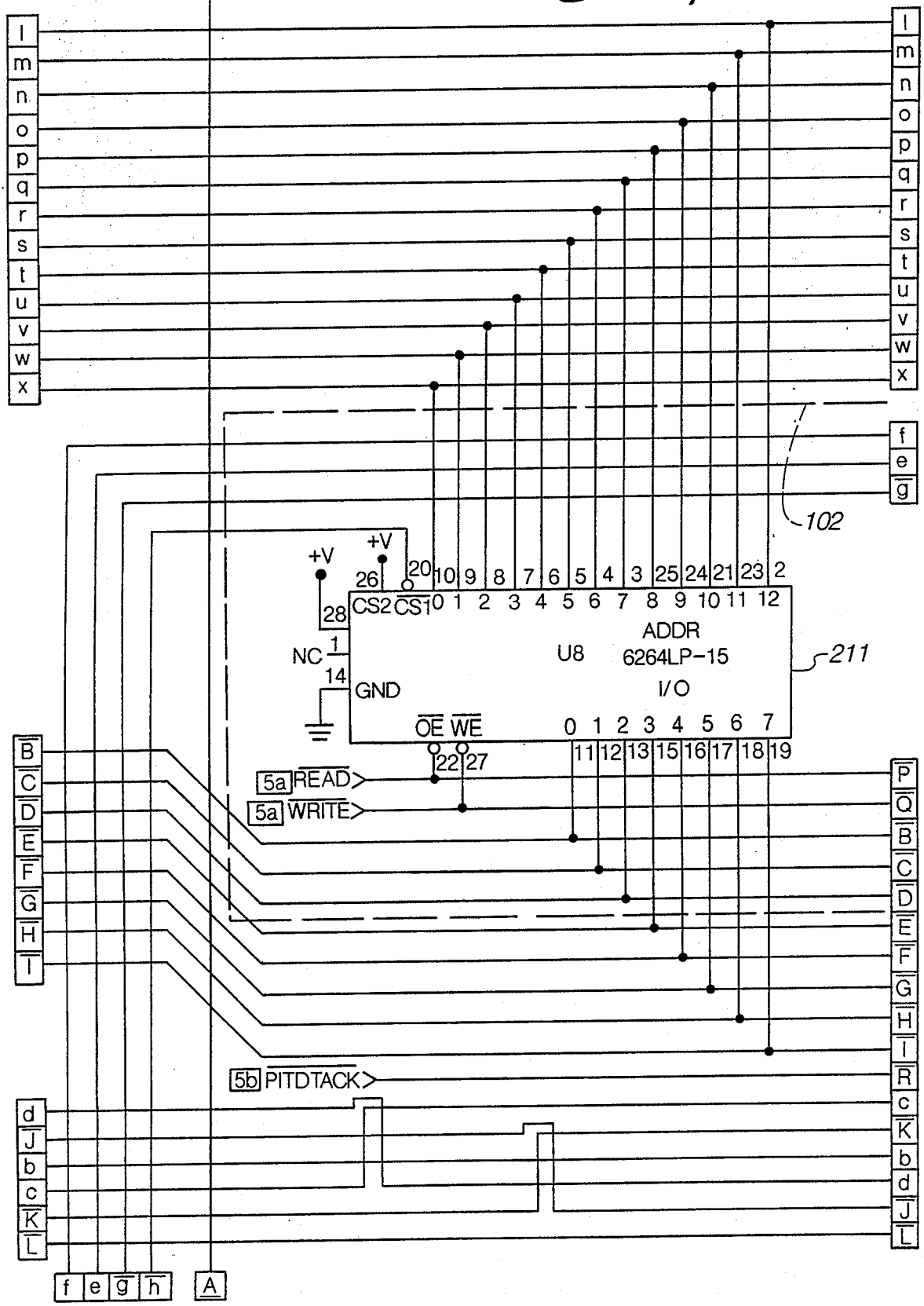

An overview of the invention can be gained by referring to FIG. 4 which is a block diagram of the invention. A plurality of inputs are provided each of which are accommodated and synchronized by the invention and are used to process the scanning data provided by the capacitive cell array 44.

These inputs include the array and associated circuitry 114 which is connected through amplifier and multiplexer section 113 to an analog to digital (A to D) converter 110 which converts the analog signals into digital signals for purposes of processing. Also connected to the multiplexer circuit 113 is the power supply 117 and a hand held densitometer probe which the operator can use to check a specific density and with a button read the specific density selected. Also connected through the amplifier and multiplexer section 113 to the A to D converter 110 is the electronic ruler 115 which measures the width of the window 51 into which the copy 14 is to be reproduced.

The power supply 117 is also connected to power down circuitry 120 which has a battery backup circuit 121 connected to a non-volatile ram 123. It is in this memory device 123 that the pixel information is stored. The power down circuit 120 and battery 121 assure that memory 123 is not lost in the event of failure of the power supply 117 or if the device is unintentionally or inadvertently turned off.

A communications interface 107 is provided to transfer data directly to or to receive data from exposure computers which can be automatically set by the invention to create the lithographic plates for purposes of making the copy. A printer and printer interface 105 is also provided, connected through input/output ports 125, to the microprocessor 101 and memory devices 102 for purposes of printing out the determined densities and other specifications of the copy to be reproduced.

An input terminal 104 which includes an input keyboard, a key decoder and displays 108 enables the operator to change operating conditions and also to observe the measured densities on visual displays. Toggle switches and other switches 106 are also provided connected through the input/output ports 125 to the microprocessor 101 which can be selectively utilized to, for example, skip the sizing functions which involves a comparison of the width of the copy 14 to the width of the window 51 determined by the ruler 115. Another toggle switch enables a calibration of the diode array 114 to take place. A similar toggle switch can be used to initialize the automatic ruler 115. Other similar functions can be utilized with external switching to the microprocessor 101.

The power supply 117 is also connected to a high power circuit 116 which provides the voltage for the cold cathode lamp 37 used for a light source. The power supply 117 is also connected to the drivers 112 for the stepper motor 34 which is used to drive the platen or copy table 16. The direction and stepping pulse is provided through buffers from the input/output ports 125 and is controlled by the microprocessor 101.

Timing and synchronization circuits 111 are provided to provide the various clock pulses needed by the array 44, the read pulses, the transfer pulses and the transport pulses. A second timing circuit 111 is provided which monitors the line frequency and through interrupt circuitry initiates the timing clocks for the CCD or CPD 114 operation. Volatile RAM 122 memory is provided to store picture data relating to the frequency of occurrence of densities and a nonvolitile RAM 123 stores the specifications for the copy after it has been analyzed. Similarly, a ROM 103 is provided for storing the software shown in FIG. 5. RS 232 and RS 422 interfaces 107 are usable in conjunction with the invention.

The basic microprocessor components 101, 103, 122, 123, etc. are interconnected by an eight bit data bus and an address bus as well as a control and decoder bus, even though the digital data consists of a byte and a nibble or twelve bits of data for each analog data reading. Consequently, each read cycle of the microprocessor 101 from the analog to digital converter 110 is a two read process wherein the first byte is read followed by the four bit nibble, enabling the resolution to be two to the twelfth power or a digital signal range of zero to 4096. This is necessary to handle a 2.7 density range for reflection densitometry and up to 4.0 clarity for transmission densitometry.

Referring now to the layout of the CCD as shown in FIG. 2, and the detailed schematic diagrams shown in FIG. 3, the identification and interconnection of the components can be shown and understood.

As shown in FIG. 2 a conventional CCD array 44 can be utilized for purposes of scanning. Charge time for the CCD is synchronized with line voltage and is preferably a multiple of cycles of the line frequency. A twenty-five millisecond charge time, one and half cycle of the sixty hertz power, has been found satisfactory.

A transfer clock transfers the accumulated data (the charge on the CCD's) into odd and even shift registers 130, 131 which are adjacent the CCD's 133 and a transport clock shifts the data through a multiplexer 135 to provide a serial analog output for each pixel location. The transport time to shift the data out of the CCD array is approximately 18 milliseconds. Consequently, as a first line of information is being shifted out of the shift registers 130, 131 the CCD's are charging to accumulate the second line of information.

Using a conventional CCD array 44 the noise level reduces the range to approximately 2000 to 1. This provides sufficient differentiation to create a density range from zero to 2.4 density, which is normally adequate for reflective copying.

The physical dimension of each CCD 133 is approximately 13 micrometers. With the reduction provided by the four millimeter lens 41, each CCD 133 detects approximately fifty thousandths of an inch of the graphic image 14. While this would normally provide an aperture of one millimeter, the standardized scan does not concentrate on any particular portion of the graphic image 14. Consequently, at least three pixels are necessary to assure that a highlight or shadow is accurately measured producing an aperture of three millimeters. A zoom lens 41 can be used to vary the pixel size.

Figure 2A:
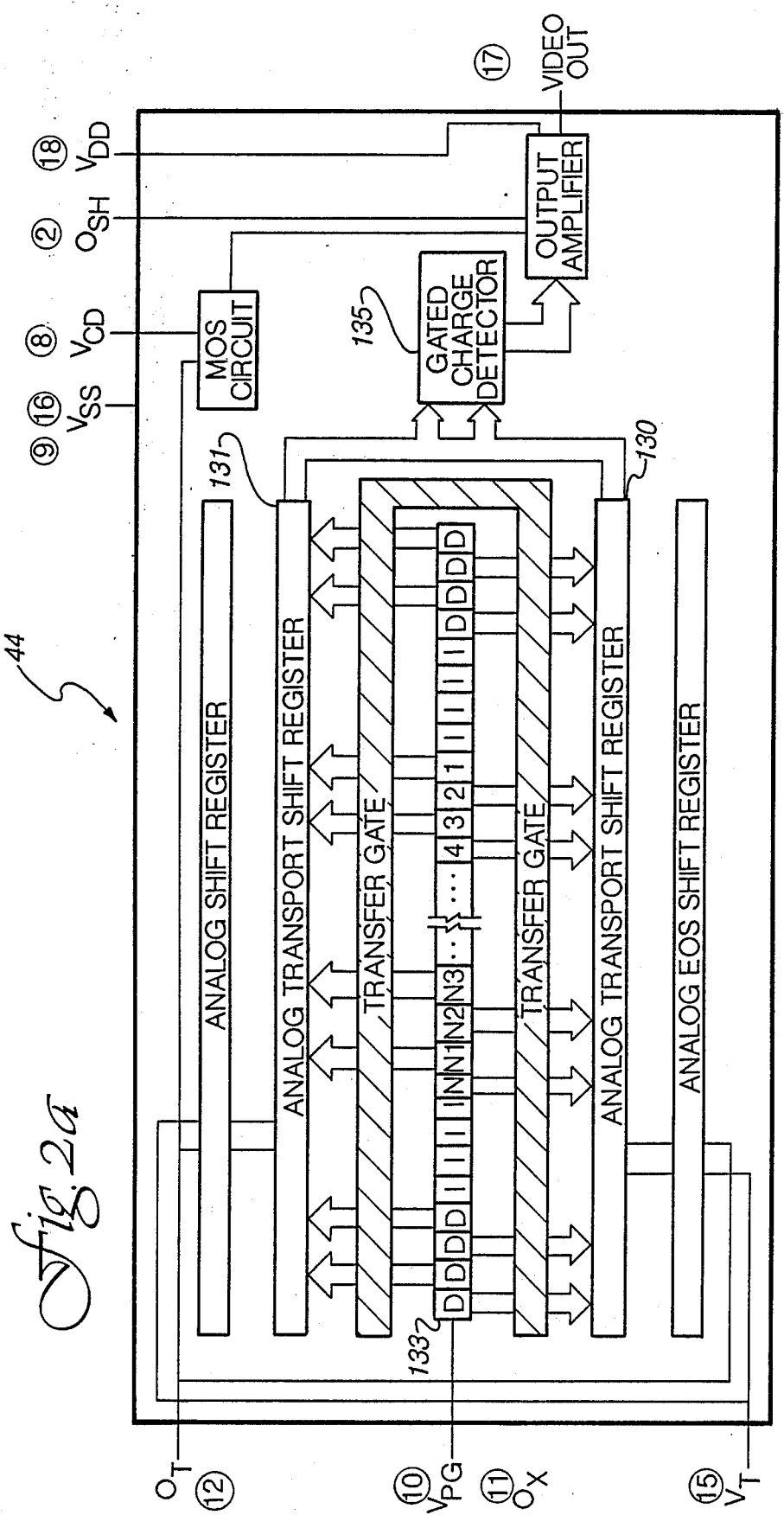
FIG. 2a is a standard representation of a monolithic charge coupled device (CCD) array including transport gates, output shift registers and a multiplexer which serially outputs the analog values detected by the CCD's.
Figure 2B:
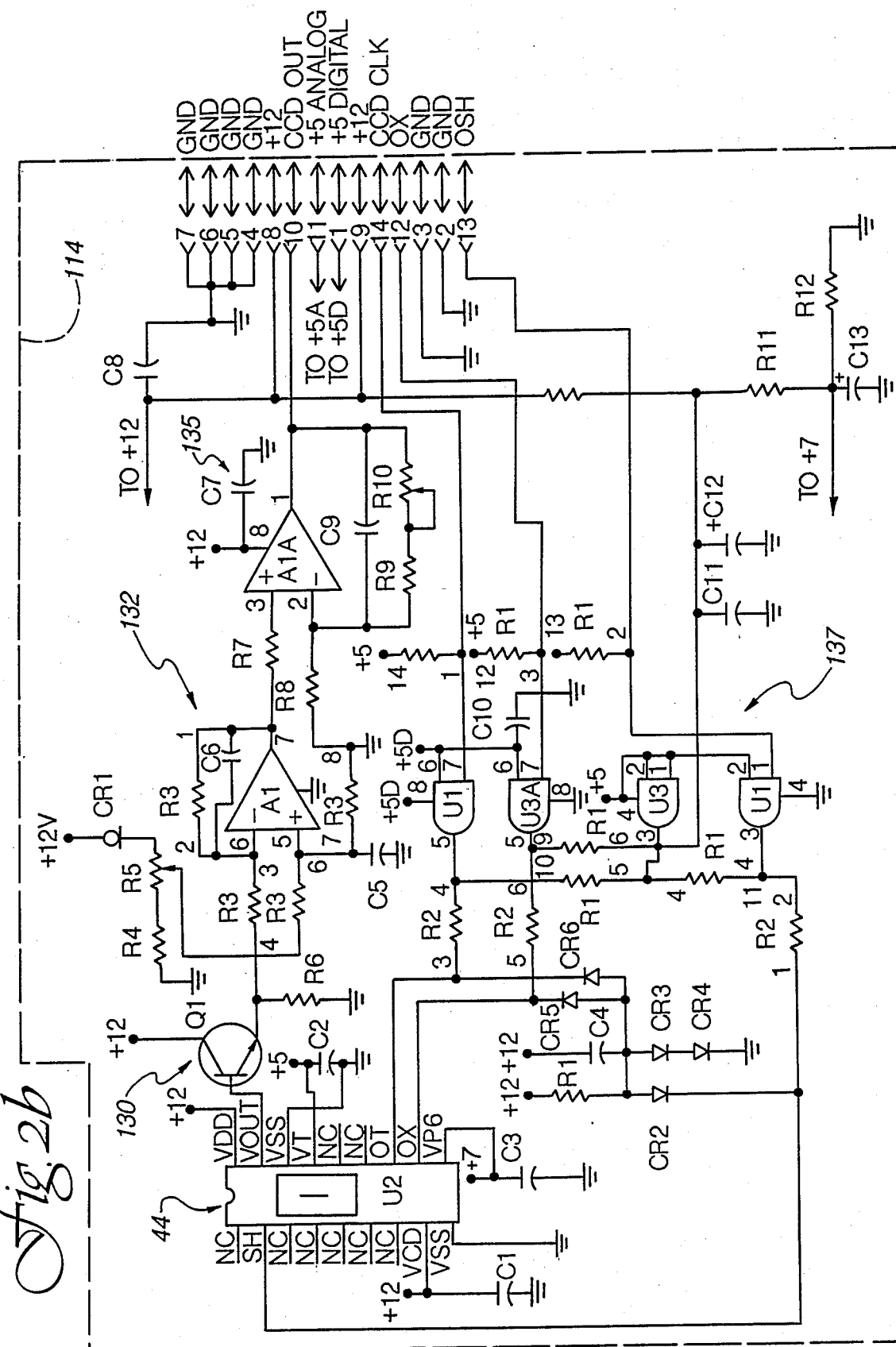
FIG. 2b is the cell array circuit used to obtain data readings from the CCD.
Figure 3A:
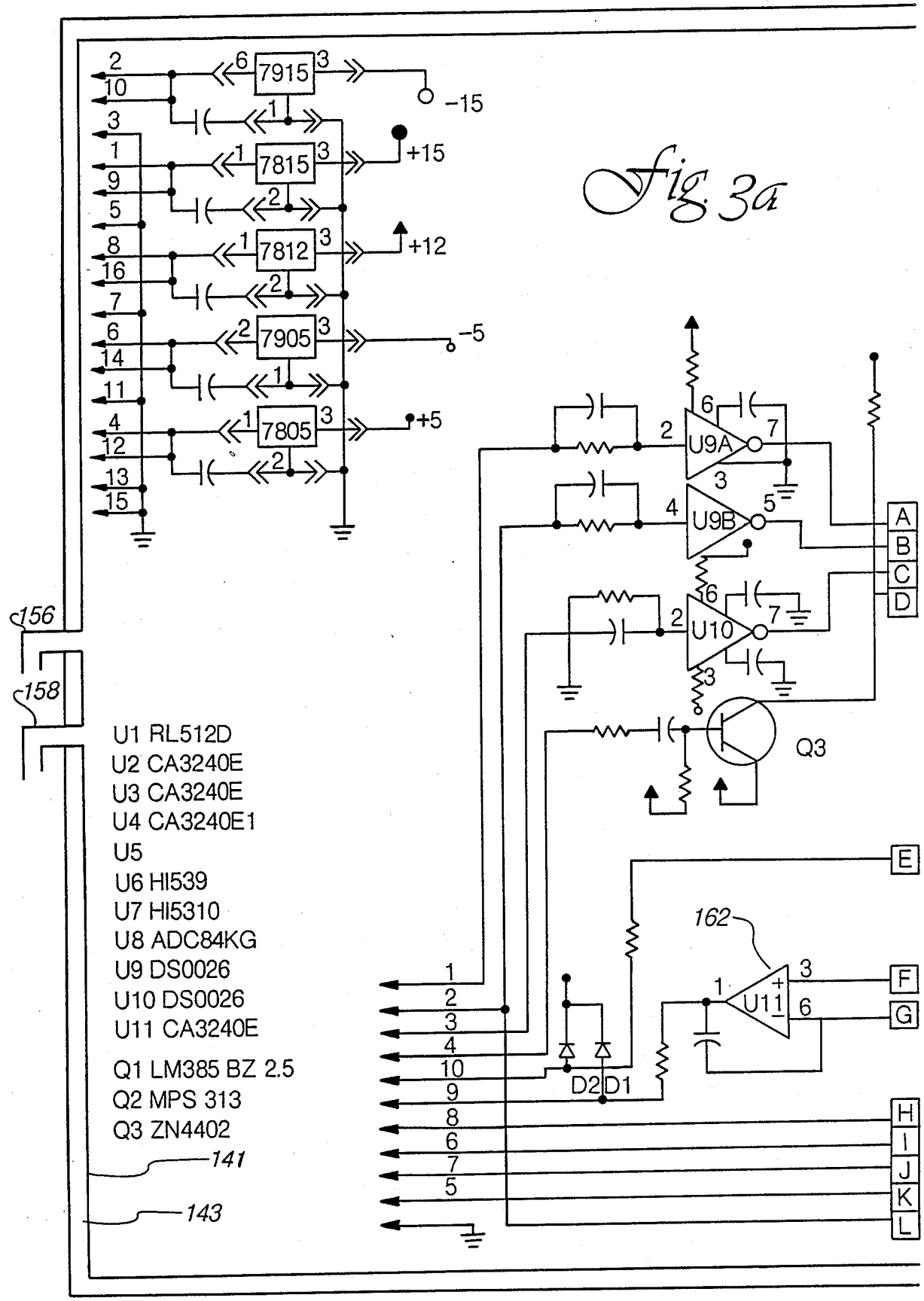
FIG. 3, consisting of FIGS. 3a1-3b, is an alternative embodiment for the diode array using charge coupled photodiodes (CPD) with temperature compensation circuits for the device to reduce the affect of noise or dark current on the readings.
Figure 3C:
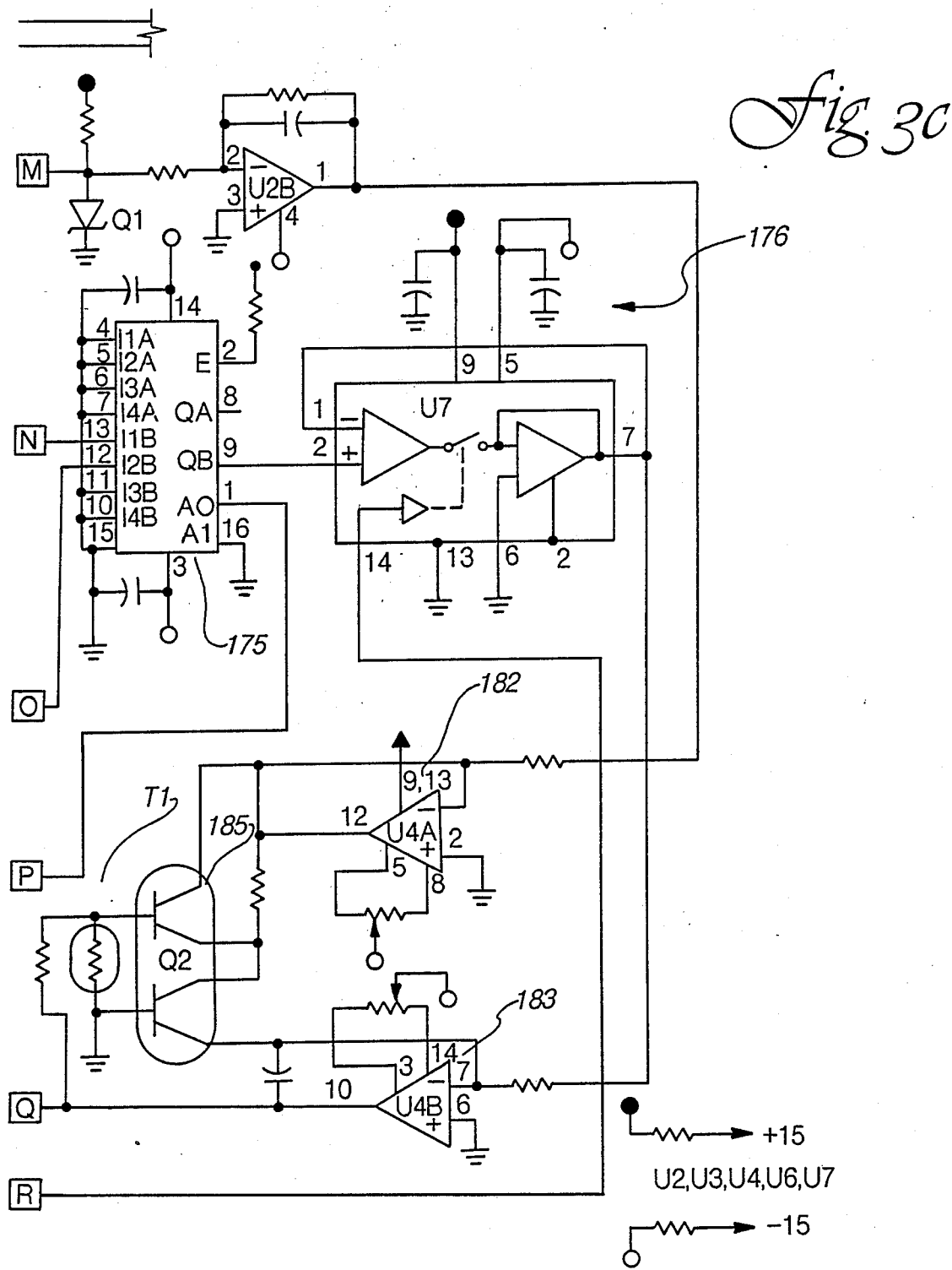
Figure 4A:
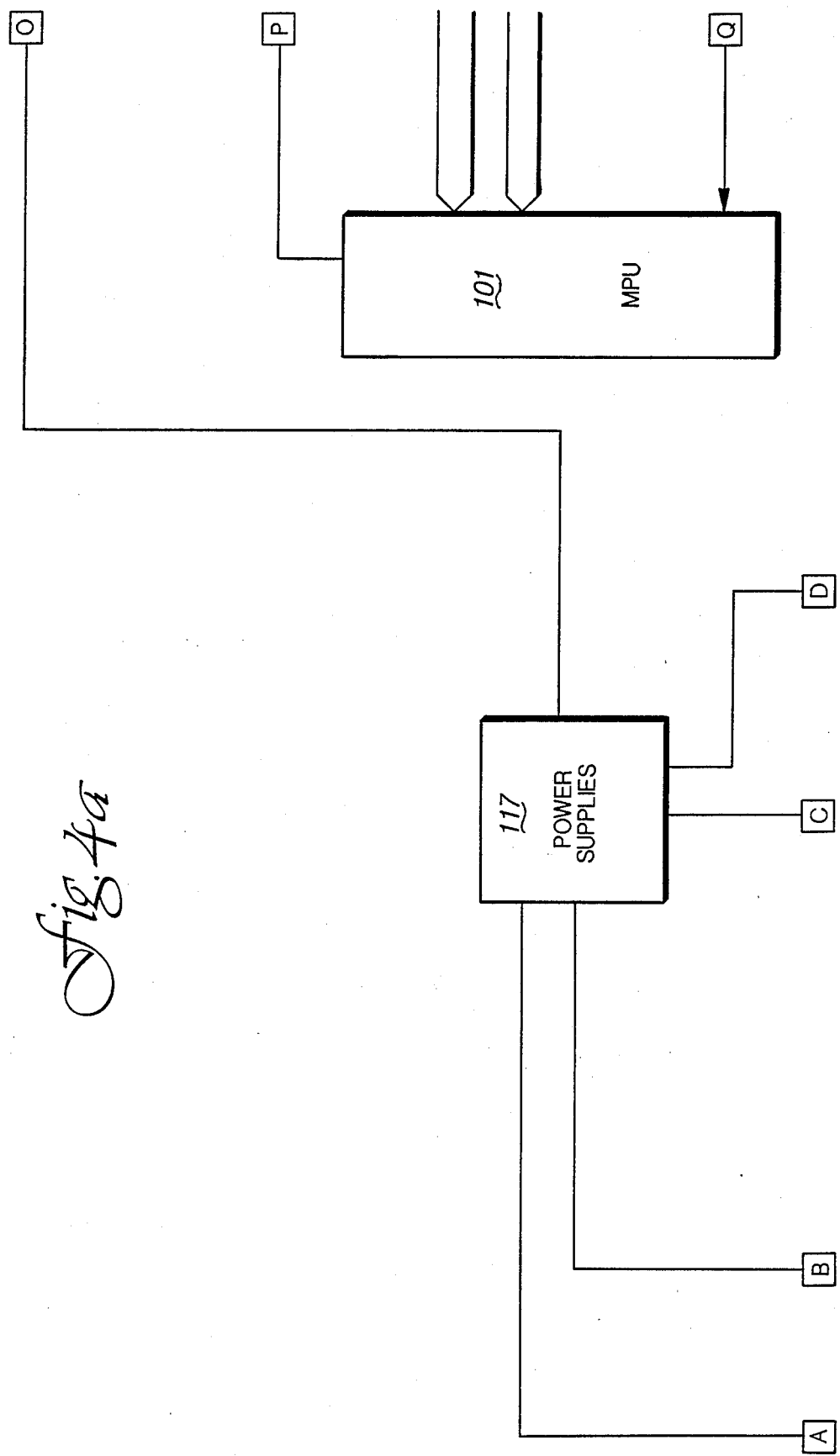
FIG. 4, consisting of FIGS. 4a-4f, is a block diagram of the electronic components of the invention.
Figure 4E:
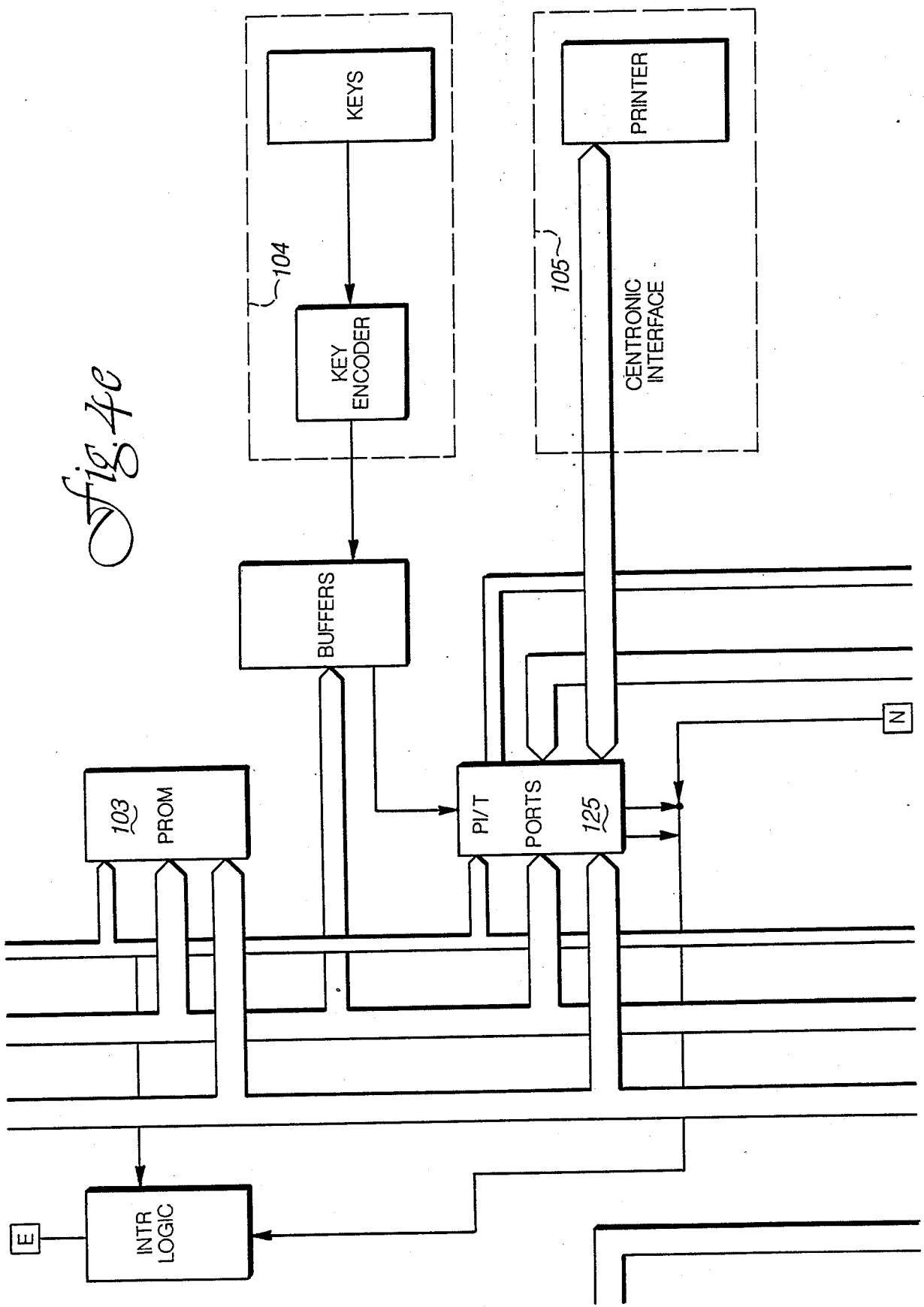
Figure 4F:
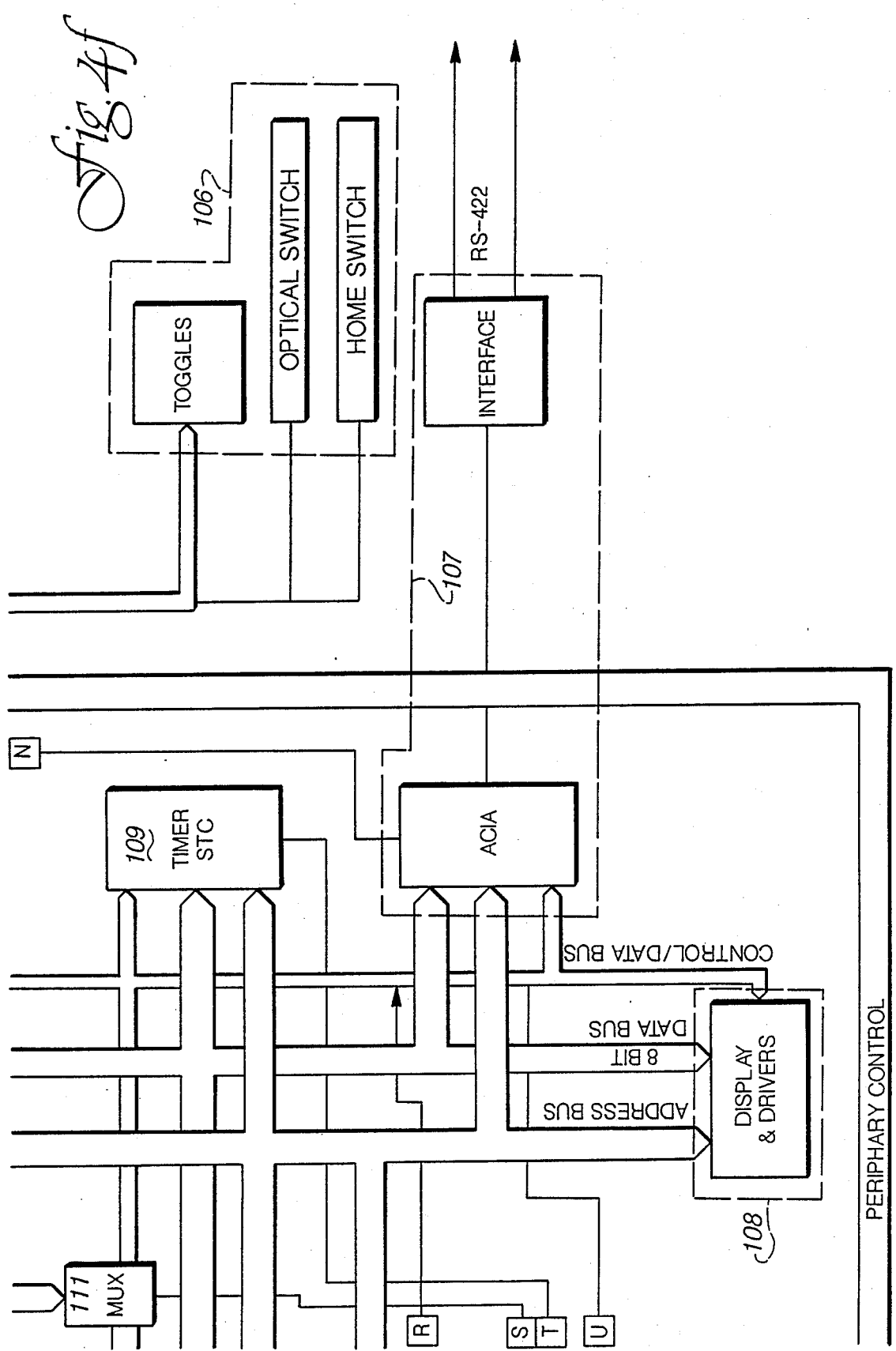

Referring to FIG. 2b the output of the CCD array 44 is passed through an NPN transistor 130 for impedance matching and is then is passed through an operational amplifier circuit 132 which inverts the signal so that white or brightness is most positive and black is least positive. The operational amplifier 132 also provides DC restoration. The output of the first operational amplifier 132 is connected to a second operational amplifier circuit 135 which increases the voltage output from zero to two volts to approximately zero to ten volts for processing. The AND gates shown and associated circuitry 137 are level shifters for control of the cell array 44 by microprocessor 101 level signals.

Shown in FIG. 3 is an alternative embodiment for the cell array 114 to obtain reflection densities to the range of 2.7 or transmission densities to the range of 3.5. A full and complete description of how the circuit of FIG. 3 is used in conjunction with the invention is more fully described in United States Patent Application Serial No. 101,359, filed Sept. 25, 1987 entitled DARK SIGNAL COMPENSATION FOR DIODE ARRAYS, the disclosure from which is incorporated herein by reference.

Referring to FIG. 3, for temperature compensated and highly accurate readings, dark signal or thermal noise, which is inherently generated in diode arrays and the associated shift registers 130, 131, must be minimized. In a preferred embodiment of the alternate embodiment the diode array 44 utilized is monolithic array consisting of charged coupled photodiodes (CDP's). The photodiode array 44 is located in a camera housing 141 which is insulated 143. A first means or method of minimizing thermal noise is provided by maintaining internal temperature of the camera, and therefore the temperature of the diode array 44, as close to ten degress centigrade as possible. This is achieved with a refrigeration unit including a heat exchanger which cools the diode array as necessary, depending on variations of the internal temperature surrounding the photodiode array. The cold air from the heat exchanger is blown through an inlet duct 156 into the camera housing 141. A return air duct 158 is also provided to return air to the heat exchanger for cooling. The camera housing 141 is insulated with foam or insulation 143 to maintain the internal temperature of the CPD array 44 as constant as possible.

To maintain the temperature at ten degress centigrade, plus or one-half degree, a small bead thermistor T3 with a very fast temperature response is physically located immediately adjacent the CPD array 44. The thermistor T3 is connected to a first constant current source D4. The output is connected to a comparator 162. The second input to the comparator 162 is connected to a second current source D3 and an adjustable resistance 160. As the output of the buffer 162 goes high or low, the signal is used to control solenoid valves (not shown) which are connected to the refrigeration unit which supplies cold air through the inlet 156.

The outputs from the CPD array 44 are connected to two buffer circuits 171, 172 where they are inverted and referenced to ground to provide a zero to ten volt output. The outputs are connected to a multiplexer 175 to consolidate the odd/even readings into a single train of data. The output of the multiplexer 175 is connected to a sample and hold circuit 179 to convert the data readings to voltage levels. Two operational amplifiers 182, 183 and a dual NPN transistor 185, with an associated thermistor T1 is used for a logarithmic conversion circuit. The logarithmic output of the transistor 185 is connected to an analog-to-digital converter 110, the output of which is connected to the microprocessor 101 for processing.

Additional temperature compensation within the small deviation of plus or minus one-half degree includes a third thermistor T2 which, with operational amplifier 198, is connected to the positive inputs of operational amplifiers 171 and 172 to put out a voltage which is reversely proportional to the small temperature deviation determined by transistor T2 not compensated for the refrigeration. The output of the temperature compensation circuit is sufficient to compensate for the plus or minus one-half degree swing of the internal temperature of the camera housing 141.

To further compensate for any residual charge which may be present, each of the cells of the diode array 133 can be calibrated using one of two methods. A rotary paddle may be rotated over the diode array 44 and a first set of readings taken. This first set of readings addresses the nonuniformity of the various cells and each reading may then be subtracted from actual readings to obtain the highest accuracy of results. Alternatively, the leading cells of such diode arrays 133 are normally masked. Calibration readings can be taken from these masked cells which, in most instances, adequately compensates for the minimal residual charge which may be present after the refrigeration and temperature compensation corrections discussed above.

Shown in FIG. 5a, are the components for the microprocessor unit including the microprocessor 101, a RAM section 102, a PROM section 103, decoding logic 201 and interrupt logic 203 used with the invention. The microprocessor 101 shown is a 68008, manufactured by Motorola Corporation, a 16 bit microprocessor with an 8 bit data bus. The microprocessor 101 handles all of the system control, user interaction and data communications. All scanning and motion control are done under the microprocessor 101 supervision. Interpretation of image data is performed by the microprocessor 101 under control of the programming shown in FIG. 6. The programmable read only memory (PROM) 103 holds the program which the microprocessor 101 uses to process all of the control functions. Input buffers are used for data bits connected to the microprocessor and corresponding output buffers are used for signals from the microprocessor. Also connected to the microprocessor 101 are two LS393 devices, 205, 206, which function as a timeout generator circuit. If any device connected to the microprocessor 101 does not respond within the time the LS393 counters 205, 206 count to timeout, the timeout generator circuitry generates a bus error.

The programming for the microprocessor 101 is contained in a sixteen kilobyte programmable read only memory chip 103. Also attached to the data bus is a bidirectional bus driver 209 which handles all communications between the processor 101 and the system other than programming instructions from the PROM 103. Preferably the PROM 103 is an eraseable programmable read only memory (EPROM) so that revisions to improve performance can be done readily. Connected to the processor 101 and the power driver 209 is random access memory 211–213 used to store the variable data including highlight, shadow and midtone densities and the like. The three RAM chips 211–213 provide a twenty-four kilobyte memory which stores the density image maps. From these maps the program determines the overall best choice for density values and prompts the user for his or her selection. Up to ninety-nine copies of data can be stored which contain the highlight, shadow, midtone and sizing information for copy to be reproduced. This is stored in RAM 213 which is nonvolatile storage so that no loss of data will occur if a power loss takes place. As shown in FIG. 5a, the memory devices 211–213 are conventionally connected to the address bus for memory location and the data bus, with read and write signals provided to read into and read out of memory.

The nonvolatile RAM 213 is backed up by a battery 121 (shown in FIG. 4) so that when the system is turned off, all the information that has been scanned and copied, as well as all the calibrated data, will be retained and will be usable when the instrument is returned to operation. It also operates to preserve the data in the event that a power loss occurs during operation of the device.

A reset circuit 27, manufacturer's designation 7555, allows the power to stabilize before the nonvolatile RAM 213 can be accessed. A power down chip 218, manufacturer's designation ICL8211, disables the nonvolatile RAM 213 from being selected in the event the power down circuit 218 detects a failure of power through the diode D2. The two circuits, 217 and 218, form a power up, power down detection circuit. When power is initially applied, when the system is turned on, the reset circuit 217, will generate a reset to all systems to make sure that everything is in the right state to start operation. In the event power is lost or the instrument is turned off, the power down chip 218 detects the low voltage, clamps everything in the off state and resets the processor 101.

Two transistors Q1 and Q2 are utilized. Transistor Q1 allows the battery 121 to be charged when normal power is applied. When power is removed from the circuit, the battery 121 supplies power to the VCC input of the nonvolatile RAM chip 213 through resistor R7.

Transistor Q2 normally allows the RAM chip 213 to be selected with the emitter connected to the chip select port of the RAM 213. However, if the power detect chip 218 detects a power failure or termination of power, the gate of the transistor Q2, which is connected to the output port of the power detect circuit 218, will cause the transistor Q2 to be turned off so that the nonvolatile RAM chip 213 cannot be selected.

Figures 5, 5A, 6:
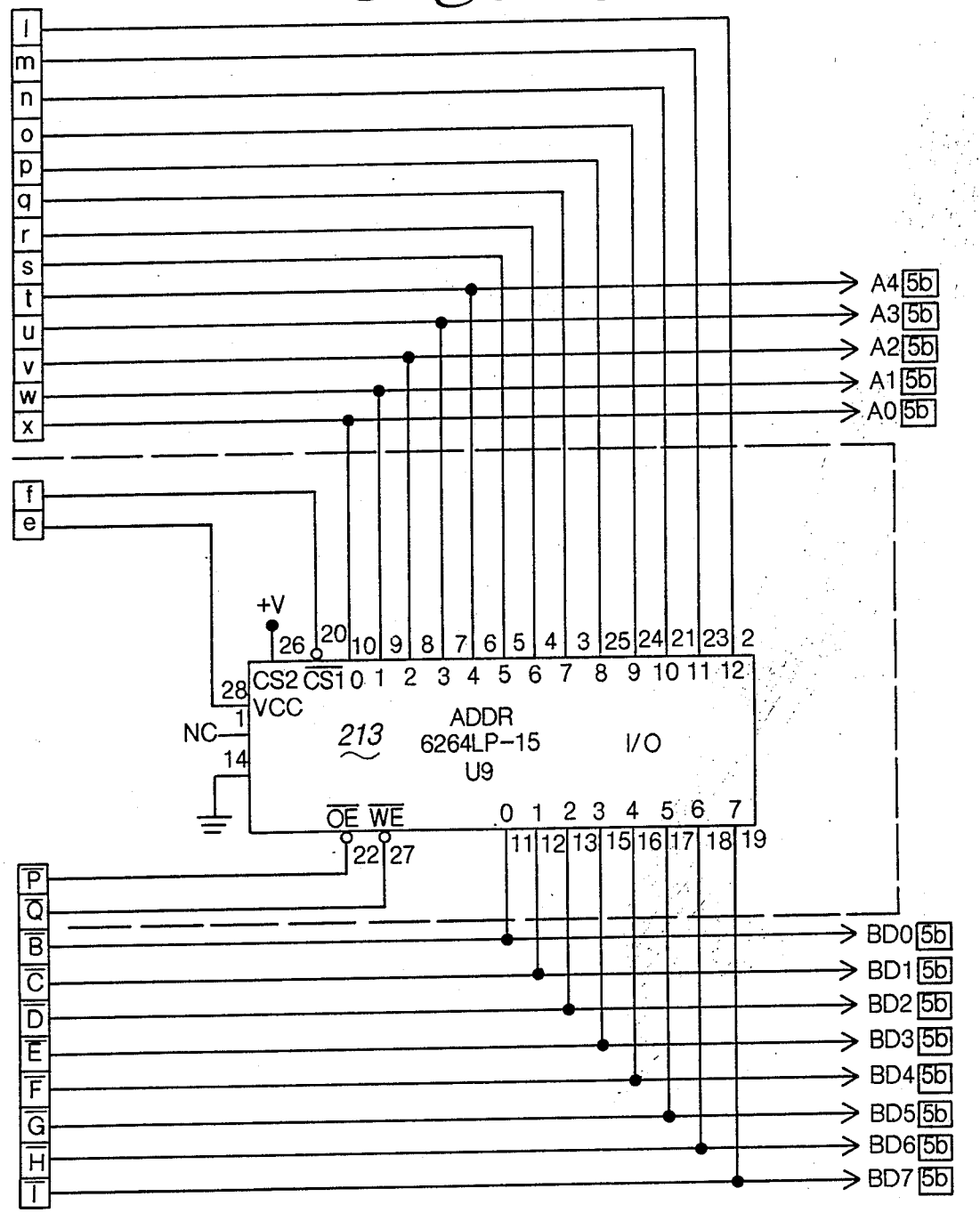
FIG. 6, consisting of FIGS. 6a-6p is a flow chart of the software which forms an integral part of the invention.
Figures 5, 5A, 6, 7, 8, 9:
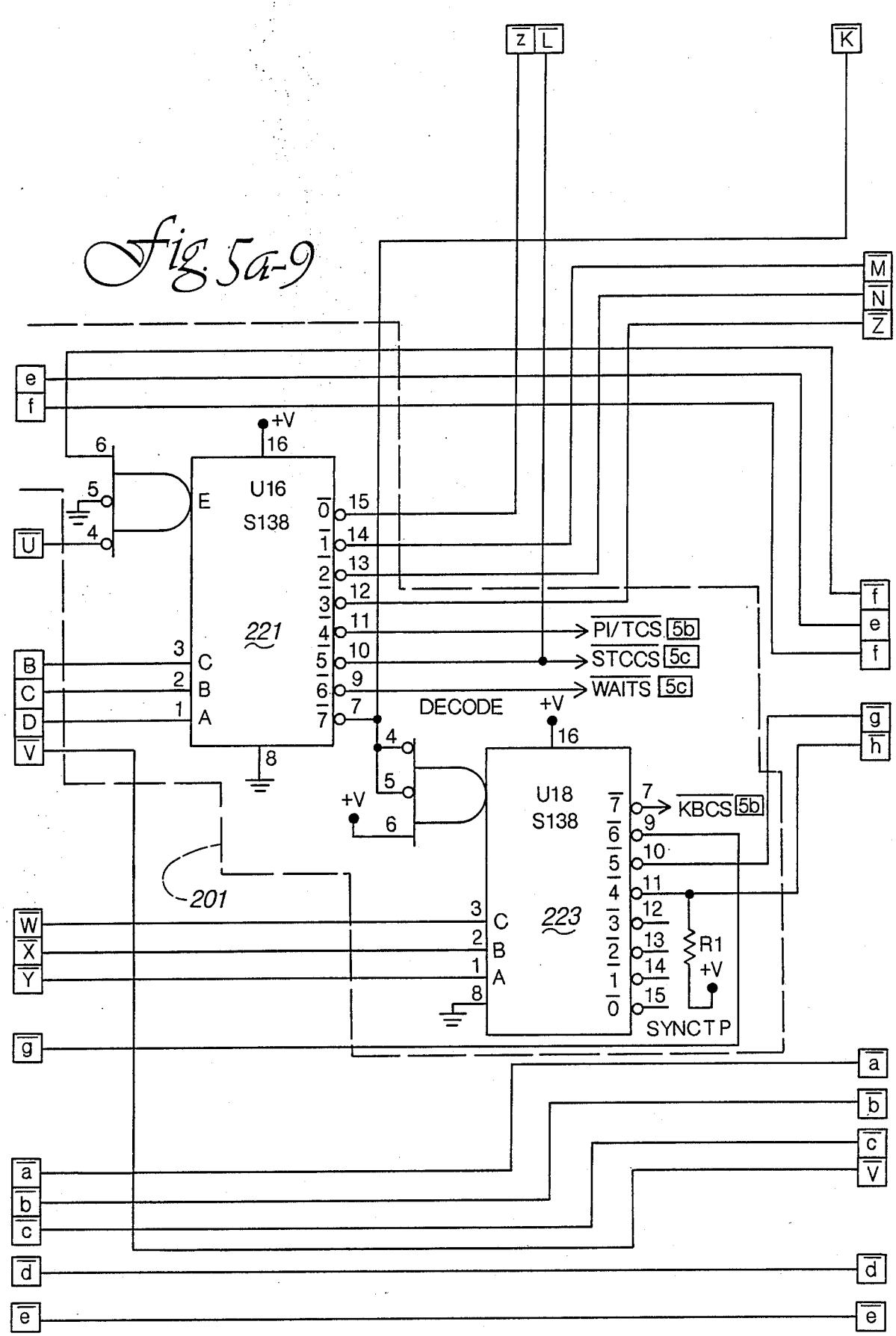
Figures 5, 5A, 6, 7, 8, 9, 10:
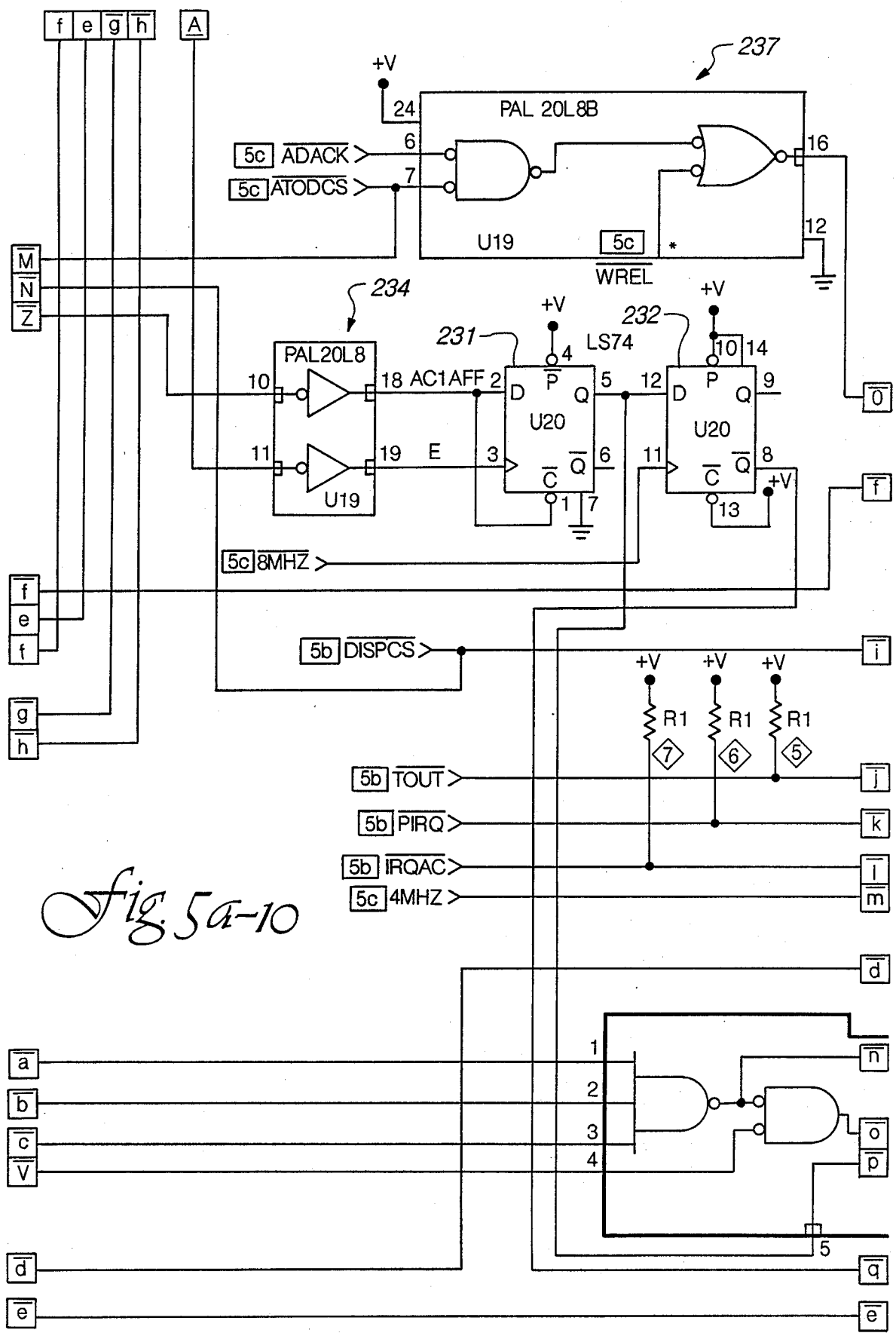
Figures 5, 5A, 6, 7, 8, 9, 10, 11:
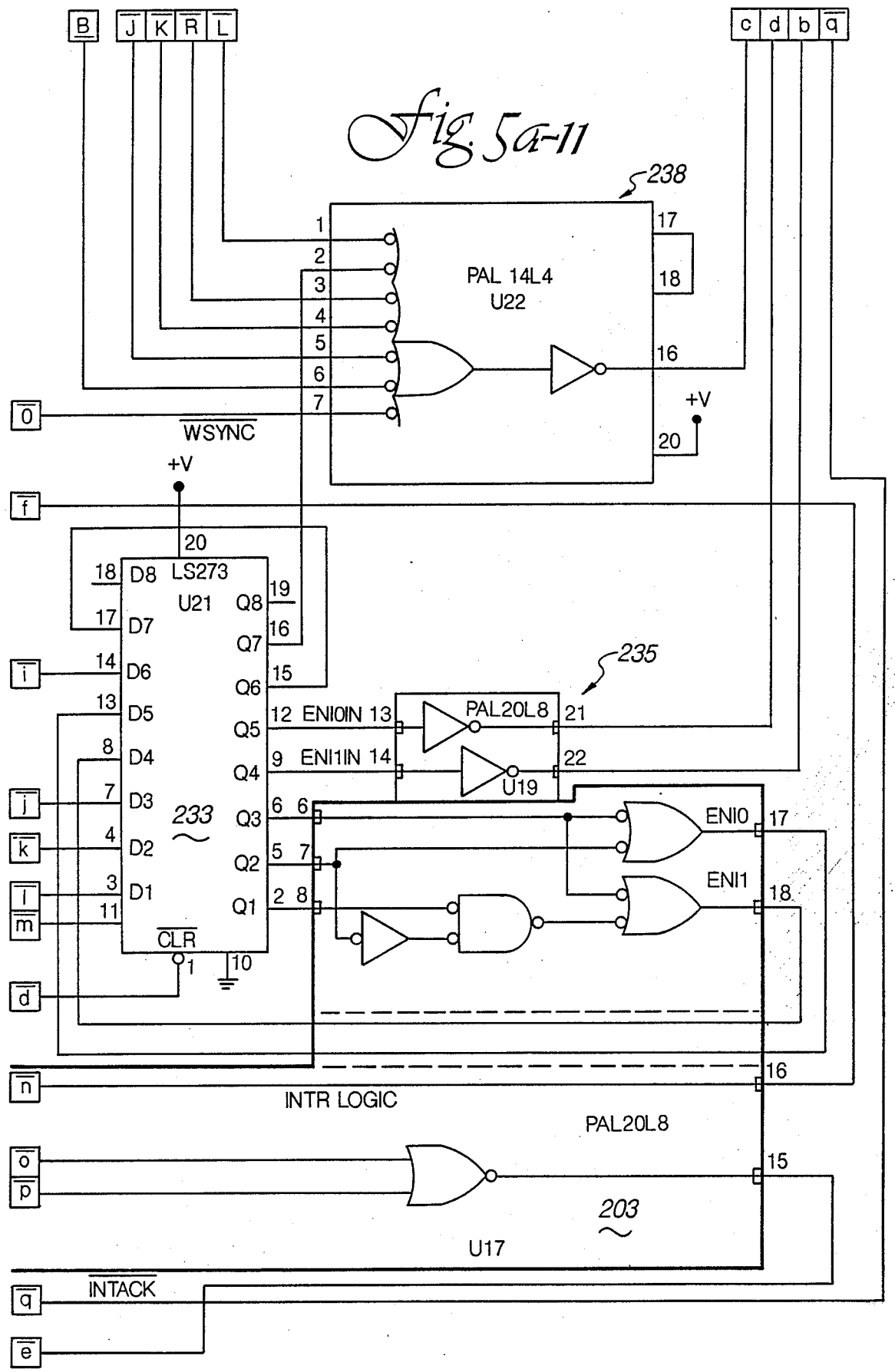
Figures 1, 5B:
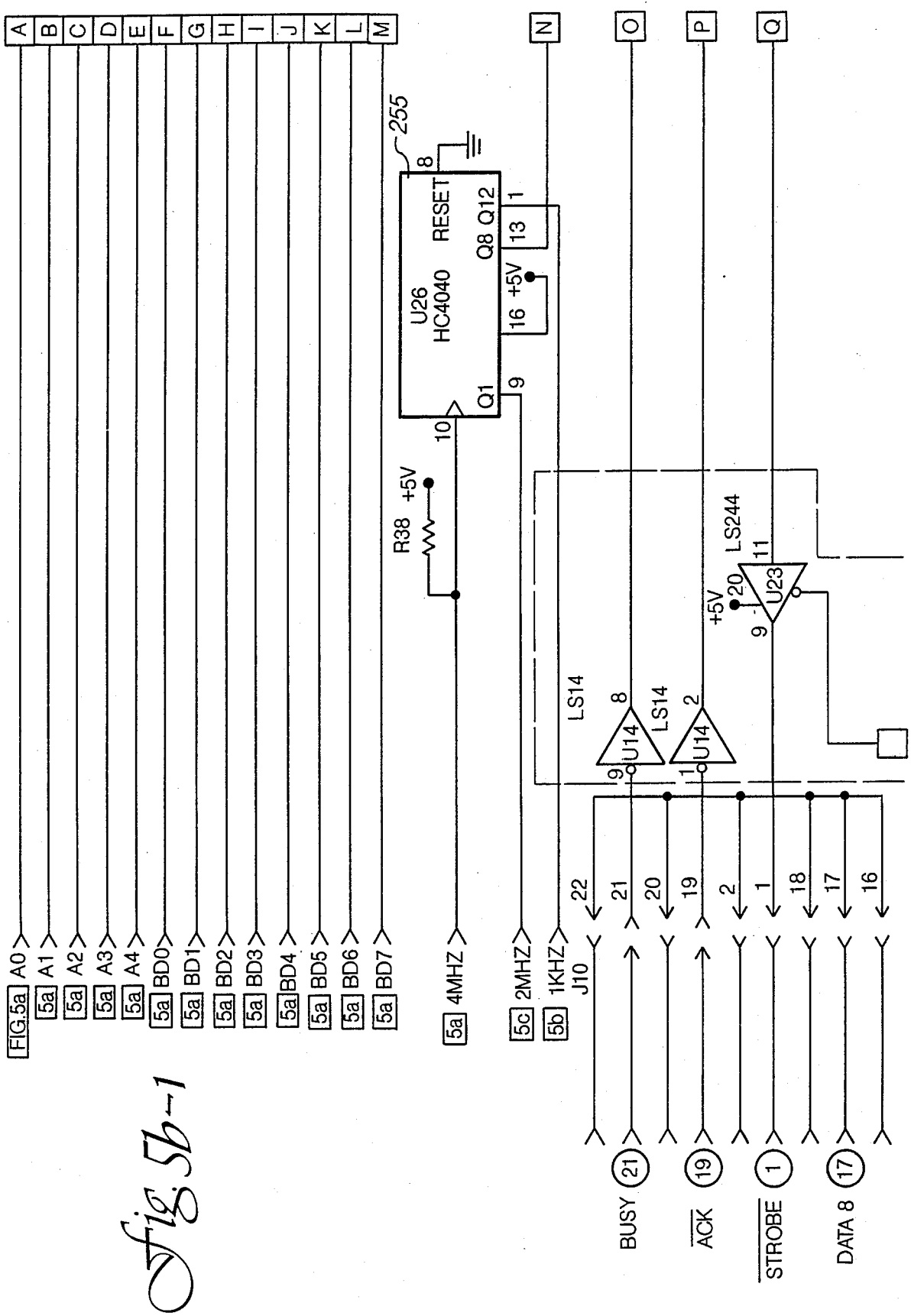
Figures 2, 5B:
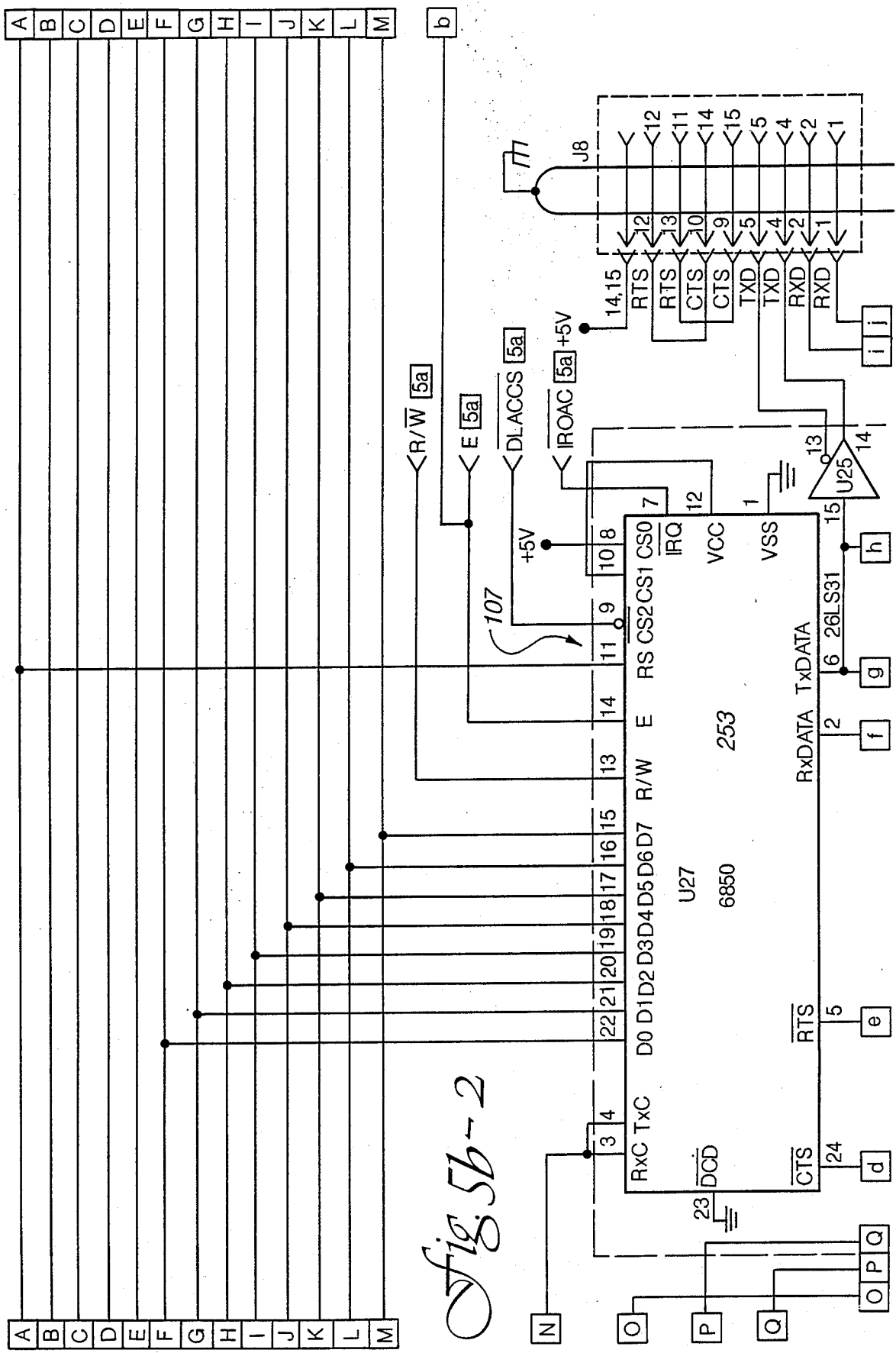
Figures 3, 5B:
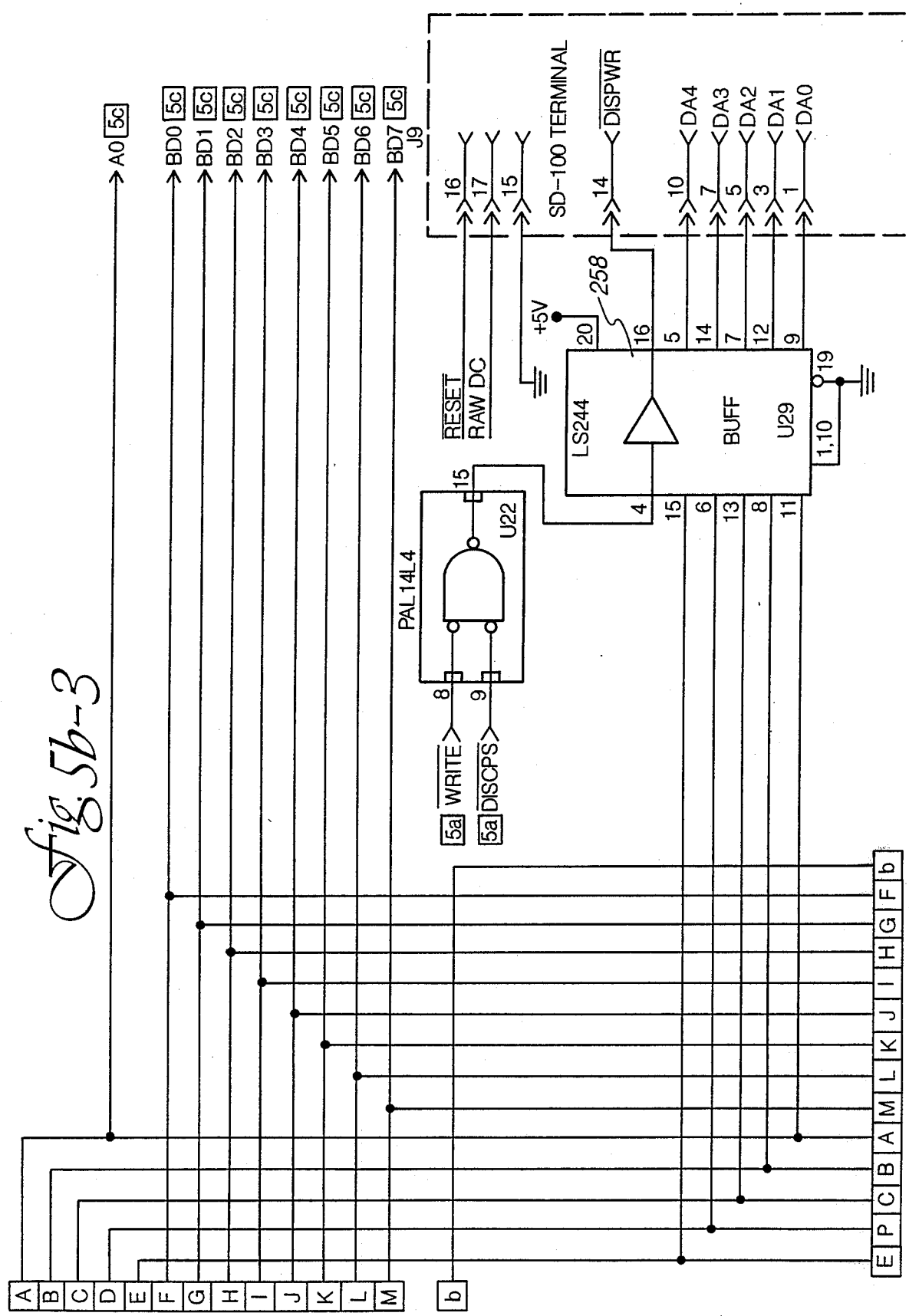
Figures 4, 5B:
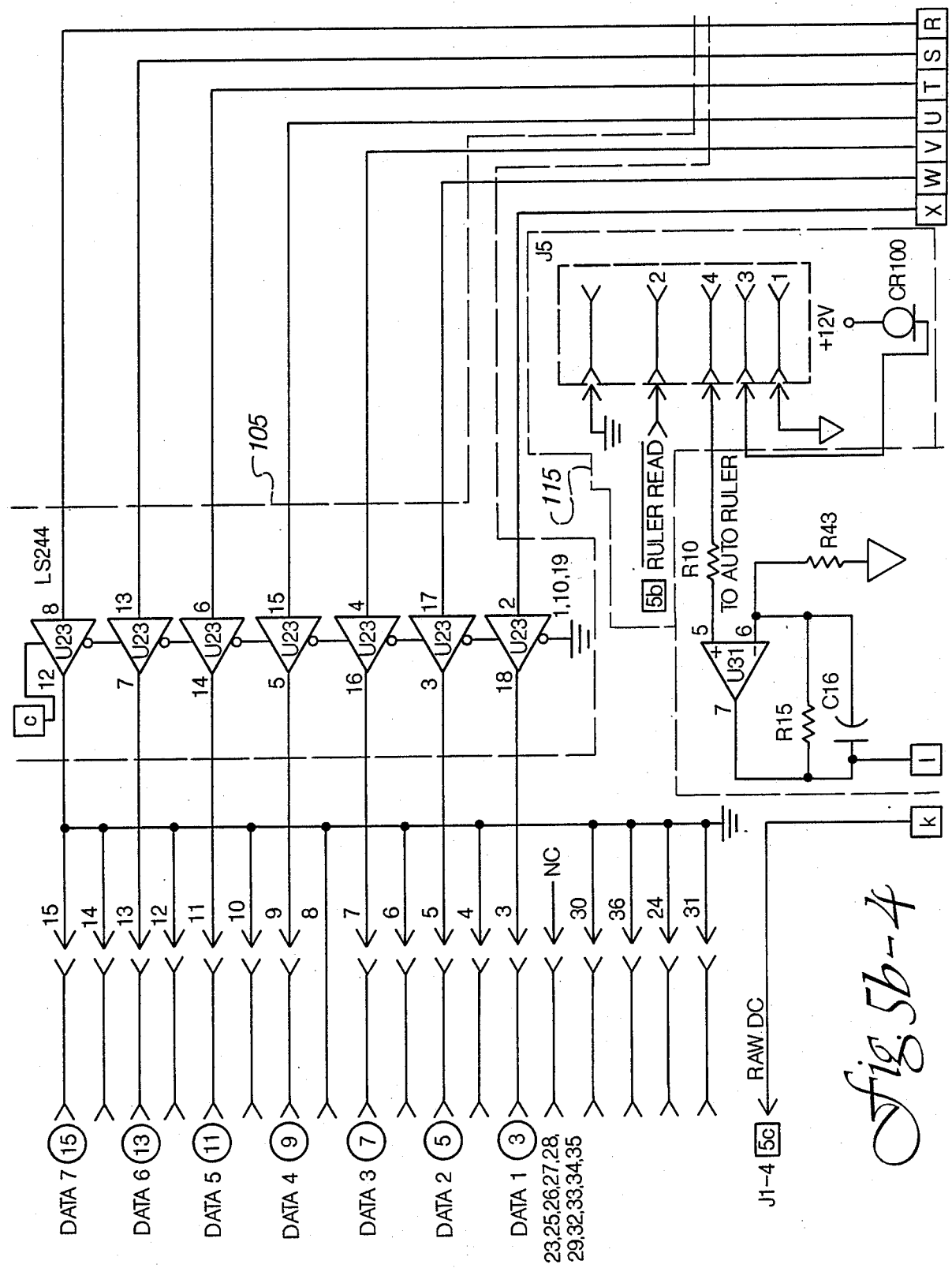
Figures 5, 5B:
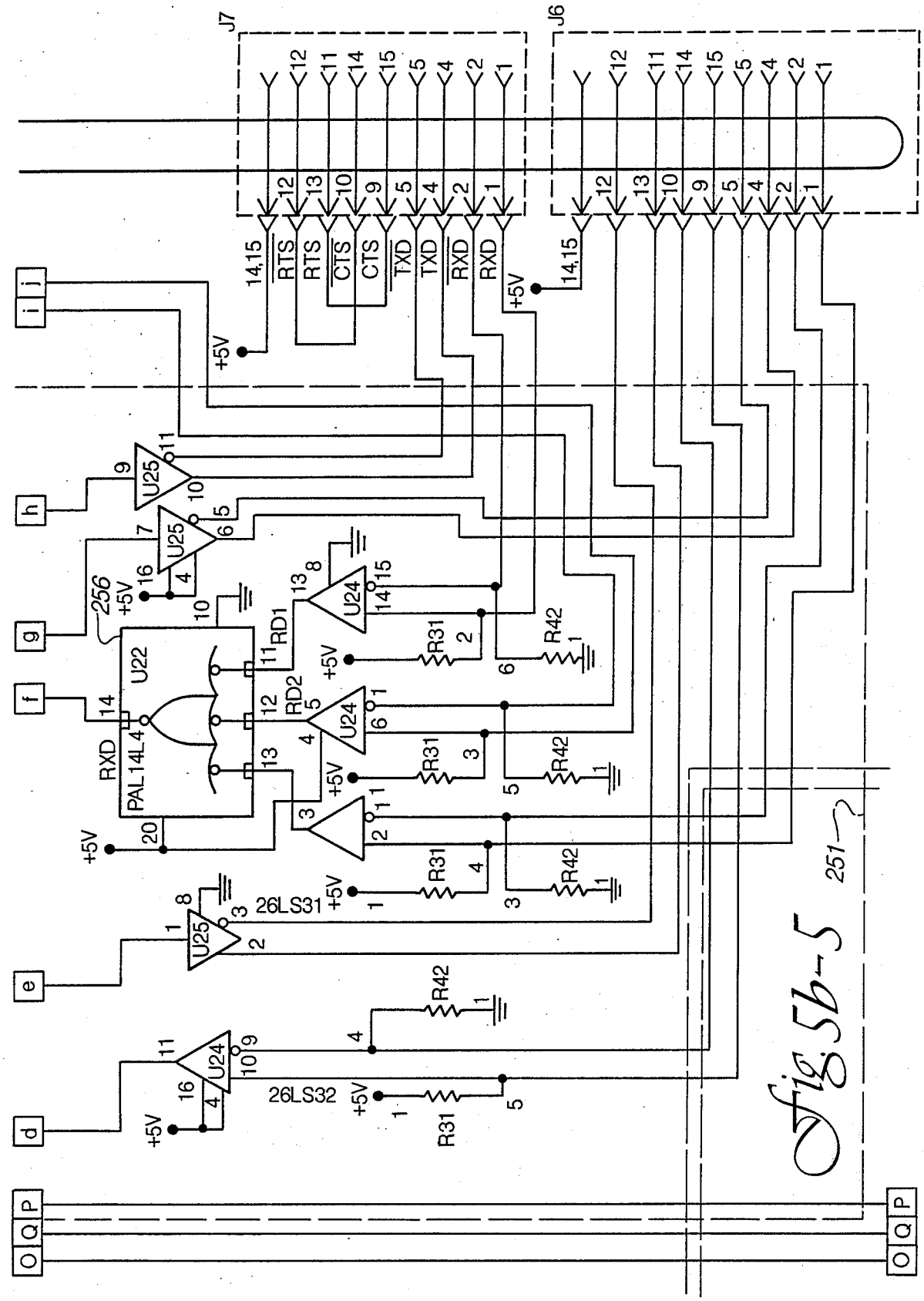
Figures 5, 5B, 6, 7:
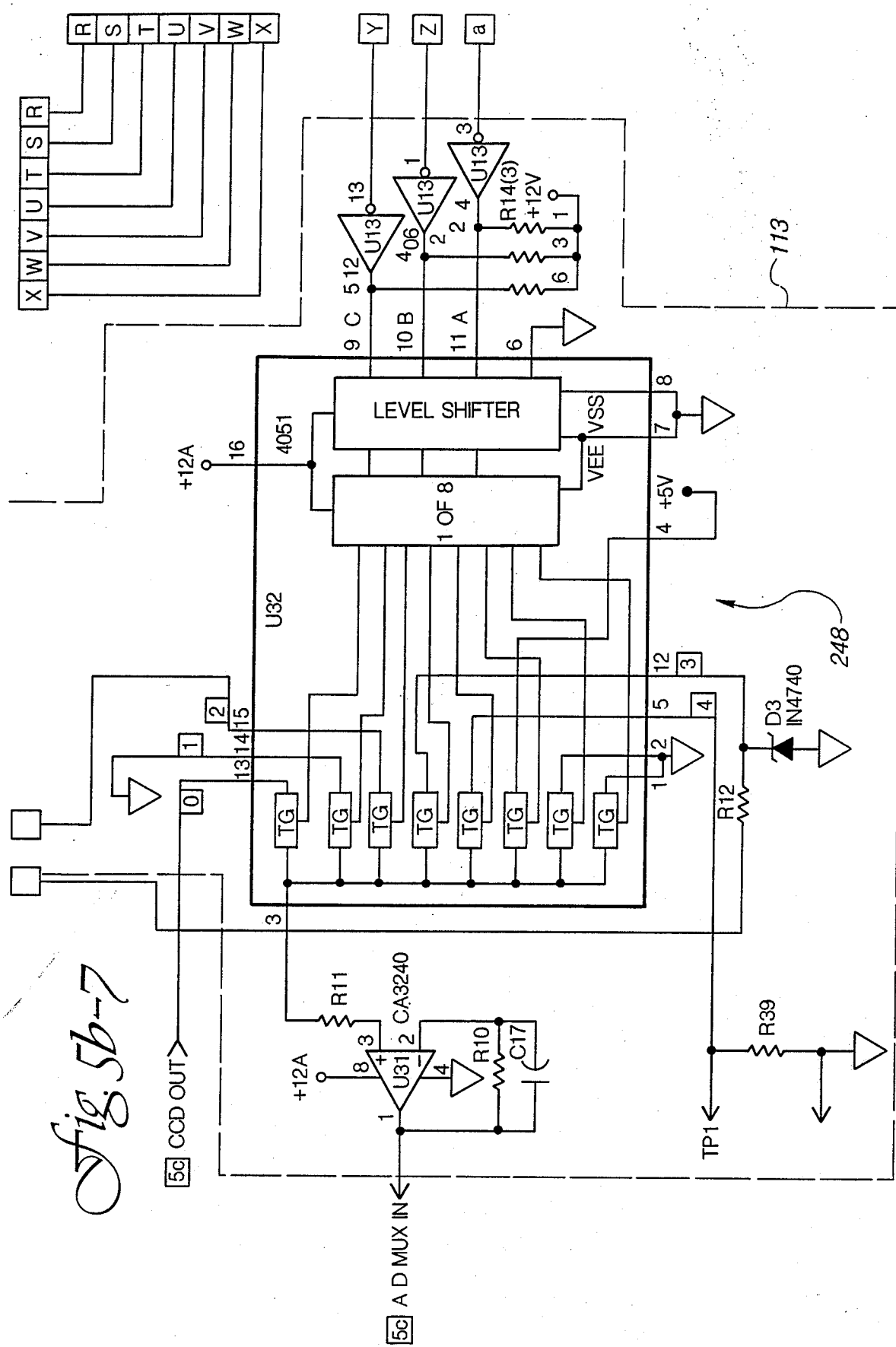
Figures 5, 5B, 6, 7, 8:
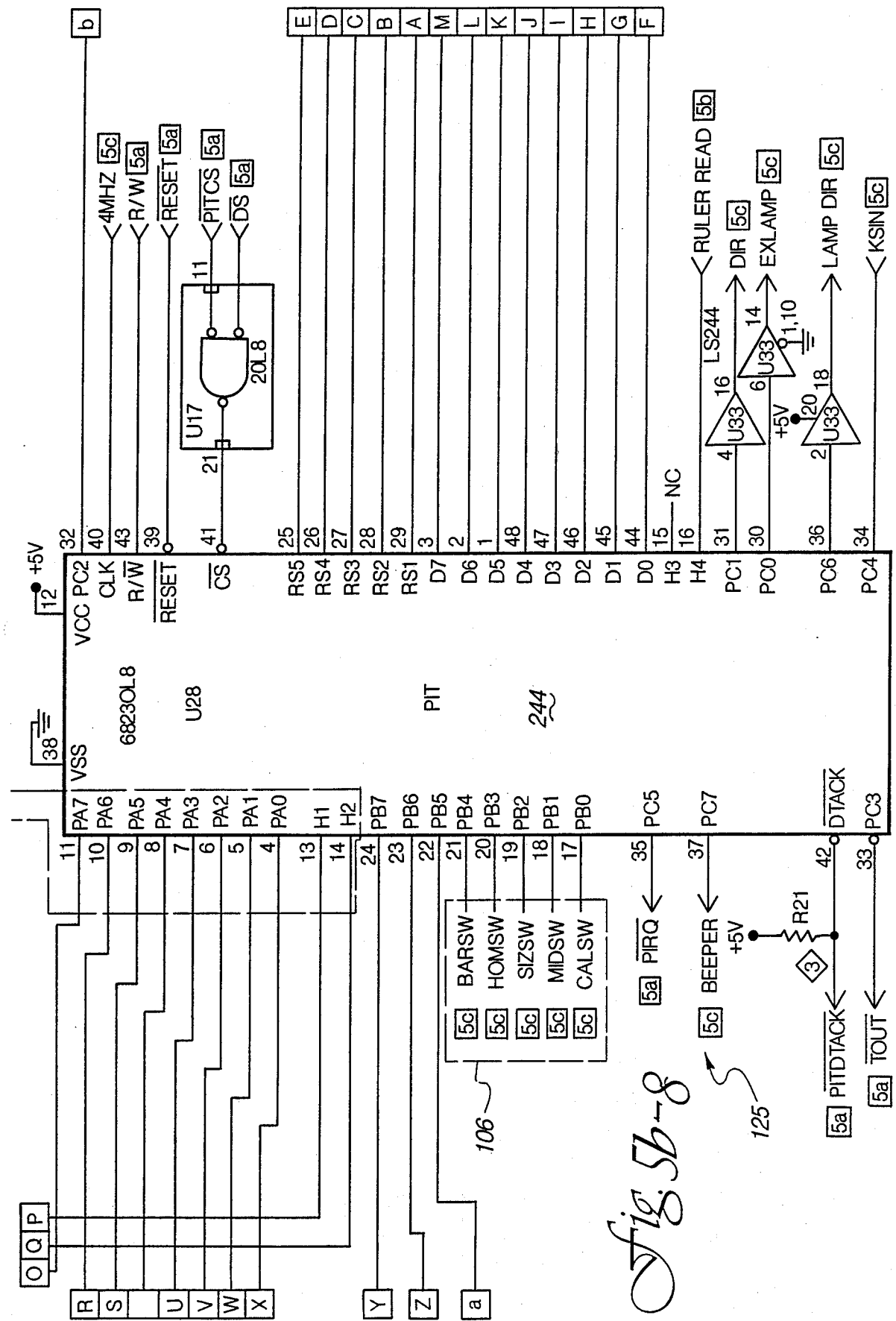
Figures 5, 5B, 6, 7, 8, 9:
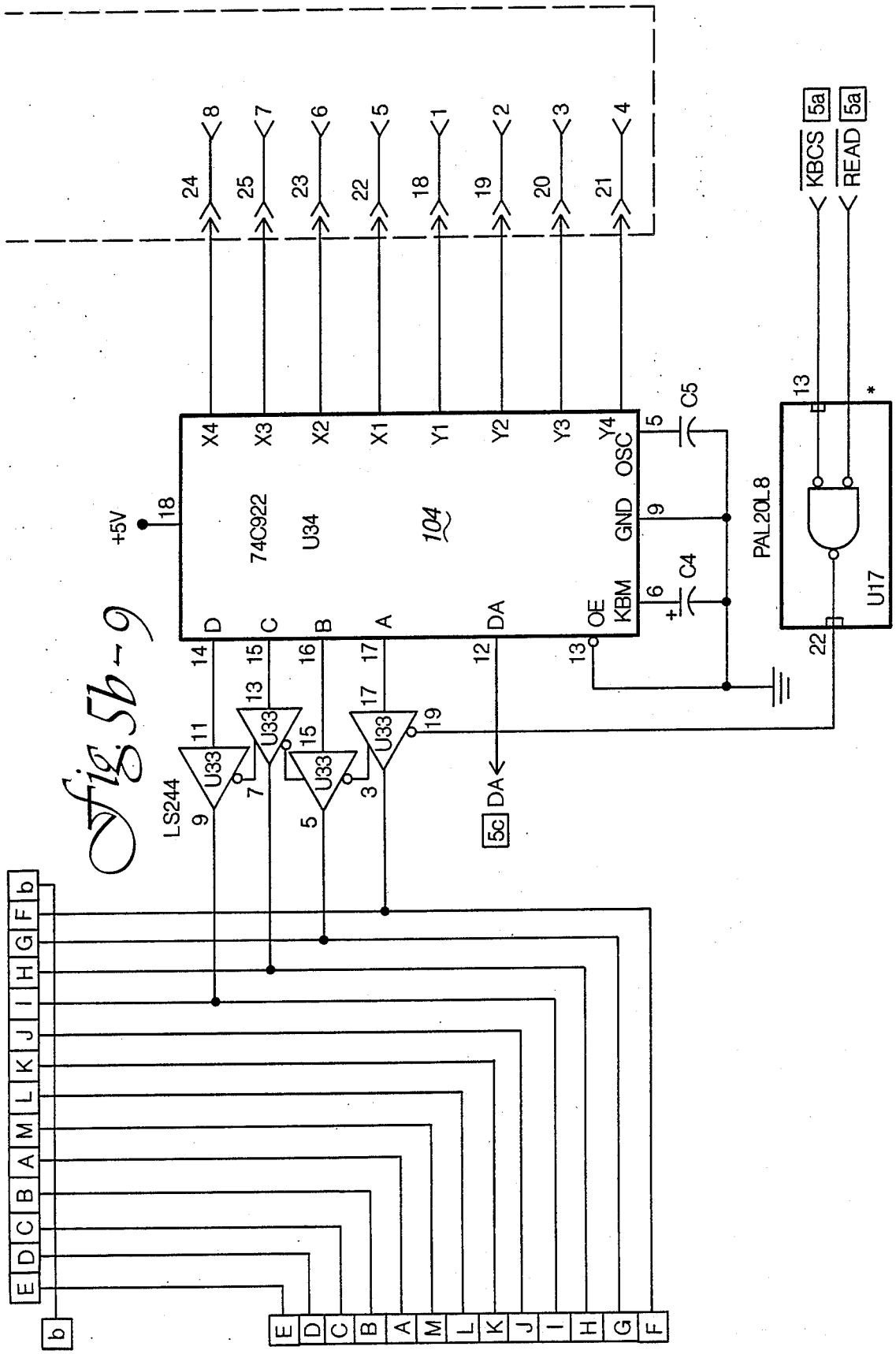

Referring now to FIG. 5b, the input/output functions are shown and can be understood.

A standard Centronics interface 105 is provided which allows most printers to be mated with the system. This interface 105 allows easy loading of data to the printer port with handshaking to allow the printer to accept data at the printer's rate. The interface 105 provides buffering and shaping for the lines coming in. The interface 105 is connected to a parallel interface timer 241, manufacturer's designation 68230,which handles all input/output for the printer and for switched options through an analog multiplexer 113 and for the keyboard 104,108.

A switch section is provided to the parallel interface timer which senses the position of toggle switches for midtone, sizing, and calibration, and also senses the optical bar sensing switch and the home position switch. The first three switches affect the options given to the user, while the last two are used for platen motion control. The platen 16 motion control switches serve as a detection of where the platen 16 is in the process. The home switch indicates when the platen 16 is in the home position ready to start a scan. The other switch is an optical switch that indicates when a cropping bar is being detected. The option switches include a calibration cycle on pin 17, which the operator can select when power is applied to the system. A sizing switch is provided on pin 19 that allows the operator to either select the original size, 100 percent reproduction, or use the ruler to vary the size of the reproduction. Finally, the midtone switch, on pin 18, allows the operator to either select midtones from an attached exposure computer or default to internal values entered by the operator of the switch.

Figures 1, 5C:
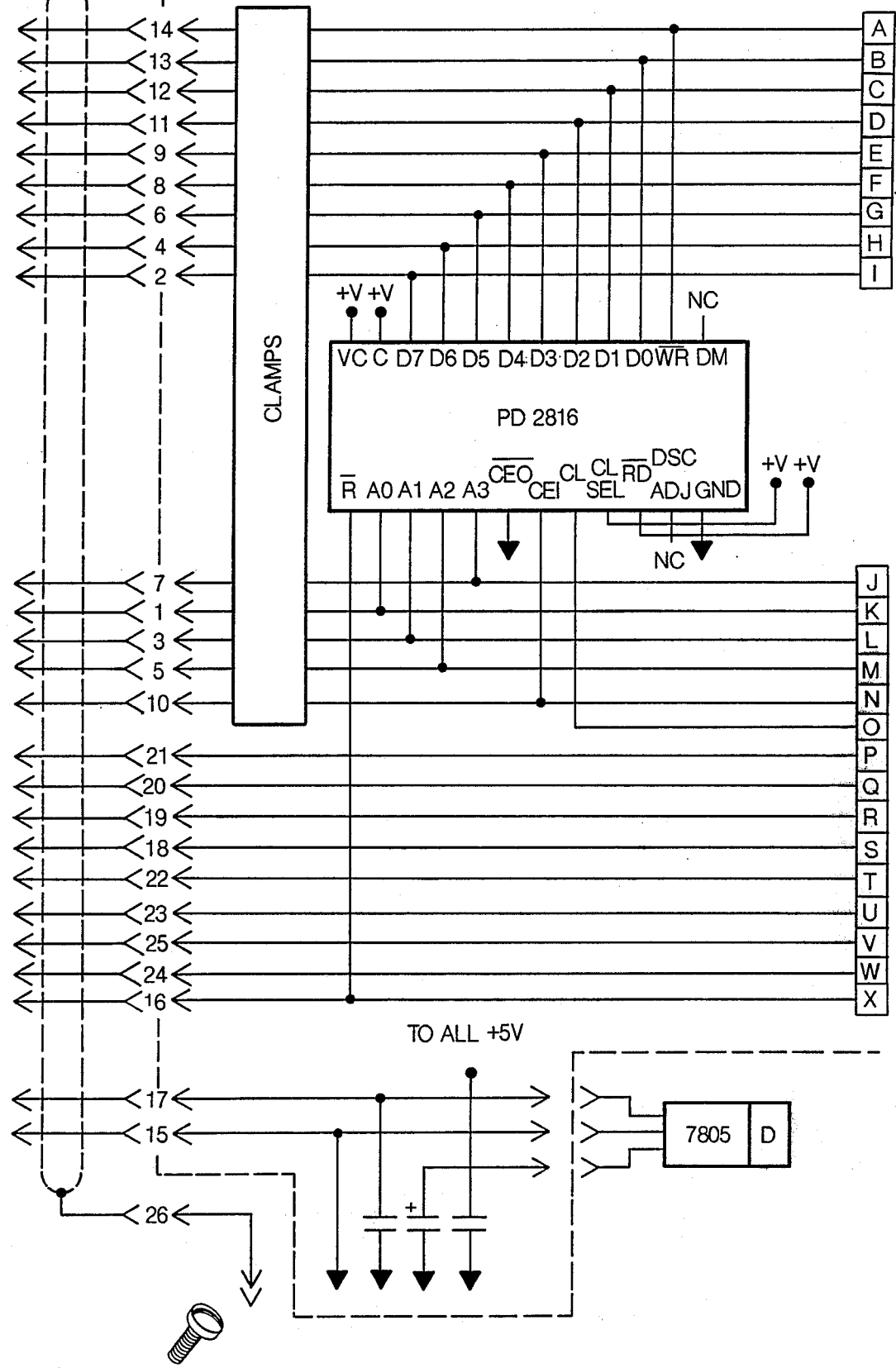
Figures 2, 5C:
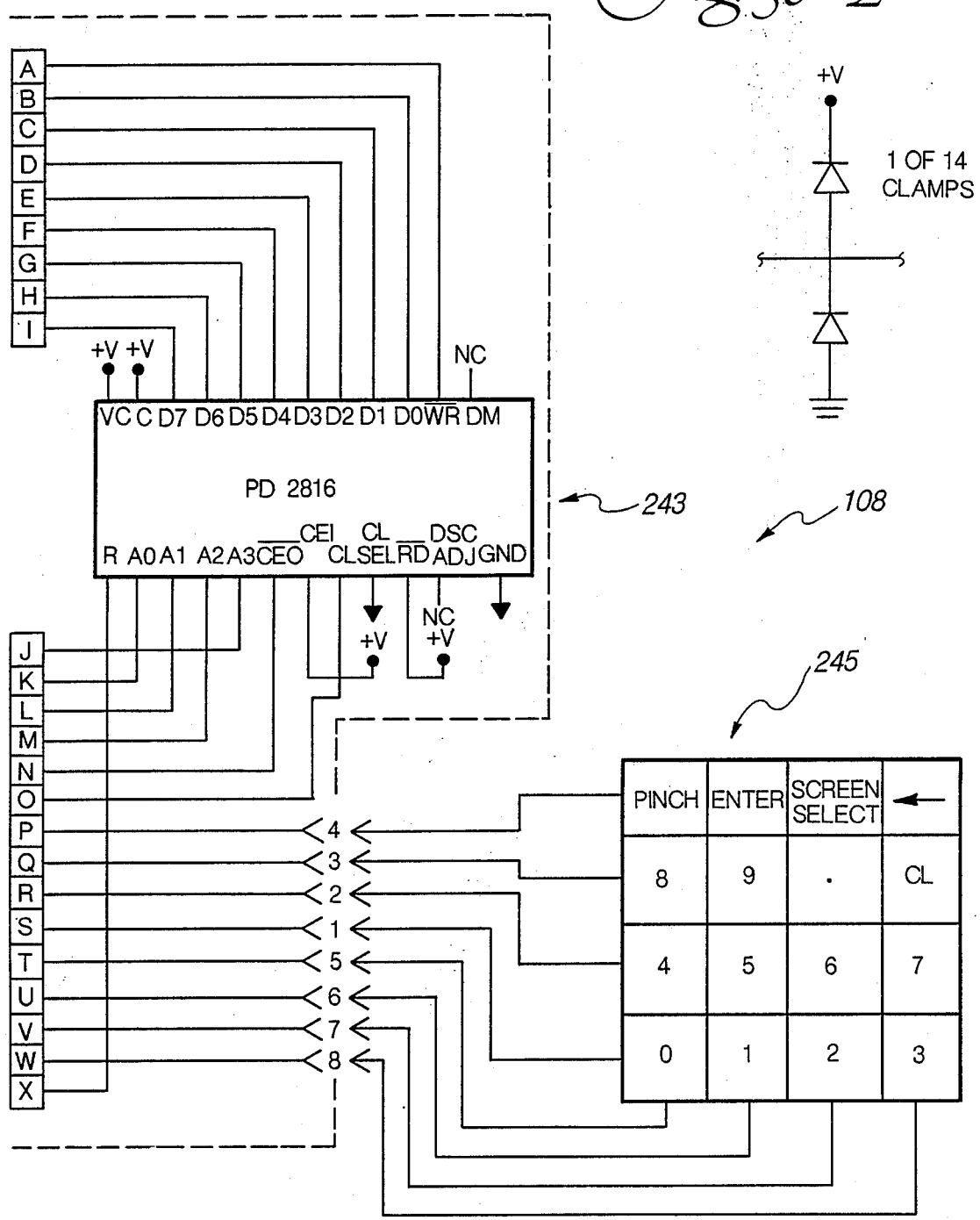

Also connected to the parallel interface timer 241 is a keyboard encoder for use to scan a sixteen key membrane keypad located on a separate display/key terminal 108 shown on FIG. 5c. The encoder 104 encodes a one-of-sixteen key into a four bit code which can then be interpreted by the microprocessor 101. The display section 243 is a sixteen position alphanumeric display used to inform the user of present scanning steps, results, and any error connections. This display also shows all data keyed in on the keypad 245 when user interaction is required.

Additional lines 246 are provided from and to the parallel interface timer 241 to control the direction of the platen 16 travel so it can go towards a home position or away from a home position. Line frequency is monitored. An internal timer keeps track of line frequency so that the scanning is synchronous with the sixty cycle frequency that is providing power to the lamps 37. As explained above, this ensures that the same amount of light is obtained for each scan. Similarly, a printer interrupt request is provided as well as a beeper line, on pin 37.

An amplifier and multiplexer section 113 is provided connected to the parallel interface timer. The amplifiers are used for buffering and conditioning the input signals. These signals are channeled through the multiplexer 248 so that, under software control, the microprocessor 101 can select which signal to monitor, i.e. data from the diode array 44 when scanning, ruler 115 when sizing input is required, and the like. The multiplexer 248 selects one of the possible eight input signals that go into the analog-to-digital converter 110. In addition to the cell array 44 data readings and ruler 115 readings, a densitometer can be used to override values determined from scanning with the cell array. A voltage check is provided to check for accurate voltages and power failure. Test points can be monitored and a voltage can be provided to the analog-to-digital converter 110 for calibration.

The ruler 115, capable of readings of up to eighteen inches, is available for reproduction sizing. The system takes in the desired reproduction width and automatically calculates the percent sizing from the original copy being scanned. A preferred range is from ten percent to five hundred percent of the original copy size 14.

Three RS-422 interfaces 251 are used to communicate between an asynchronous communications interface adapter 253, manufacturer's designation 6850, and external exposure computers. Preferred midtone density ranges as well as copy information are passed via this interface. A frequency divider 255, manufacturer's designation HC4040, divides the four megahertz system clock down to approximately four kilohertz for the communications device 253. The preferred frequency is chosen to be compatible with the device with which the communications device 253 is communicating. The communications controller 253 can read or write to the microprocessor 101 and handles all communications that take place with the exposure computers. The RS-422 interfaces 251 can drive up to 4000 feet of cable with no noise problems. It will be obvious to those skilled in the art that more or less devices can be connected with a similar circuit.

The three input gate 256 is used to select one of the devices to communicate with, in a conventional manner.

Two drivers 258, 259, manufacturer's designation LS244 are utilized as buffers to the display keyboard 108 to run the display of information to be displayed from the processor 101.

The keyboard 245, shown in FIG. 5c, utilizes, in addition to the numeric values and a decimal point, a backup key to return to the last value, an enter key to enter data keyed into the keyboard 245, a screen select key, a clear key and a pinch key, which will be discussed in more detail in conjunction with the software.

Figures 1, 5D:
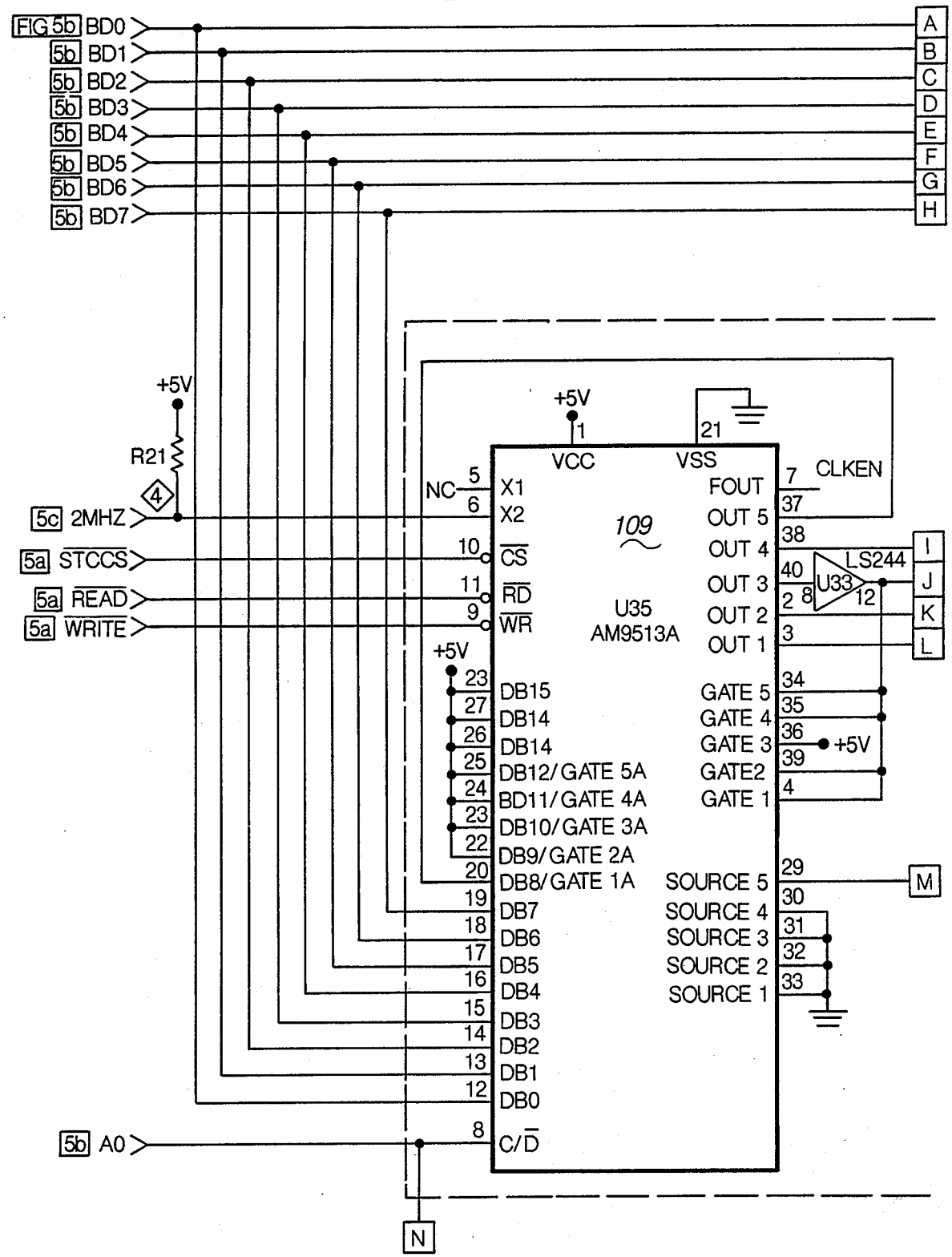
Figures 2, 5D:
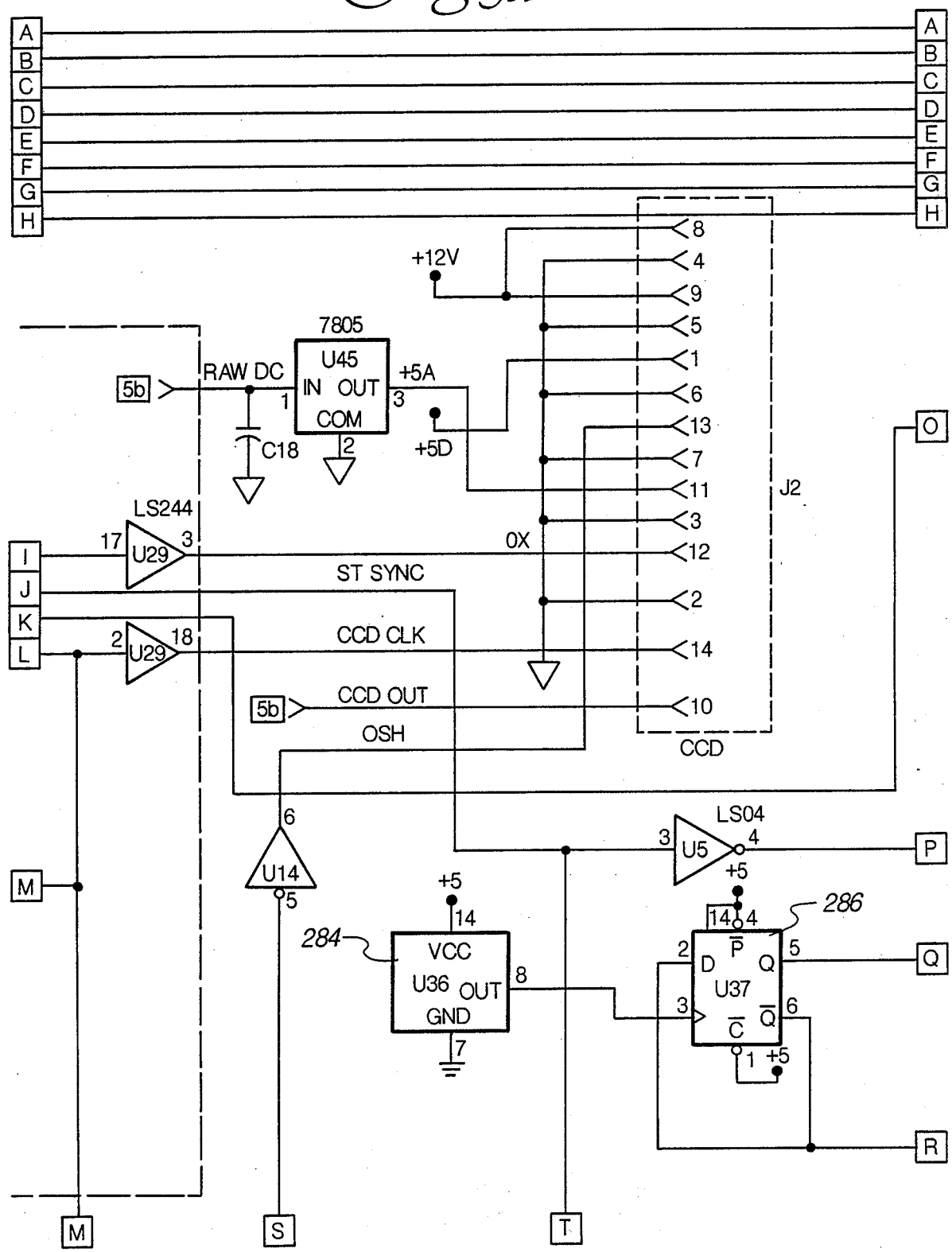
Figures 3, 5D:
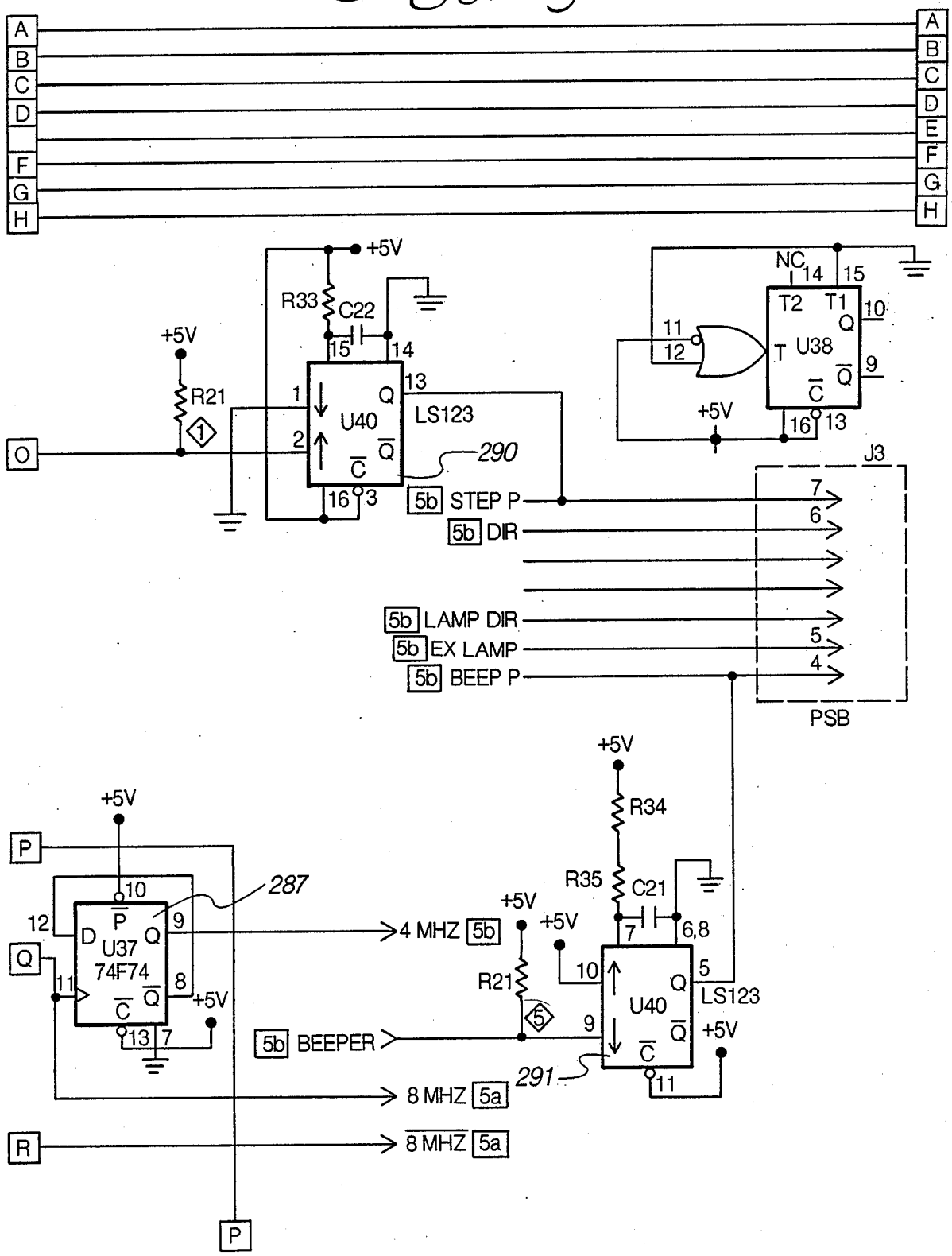
Figures 4, 5D:
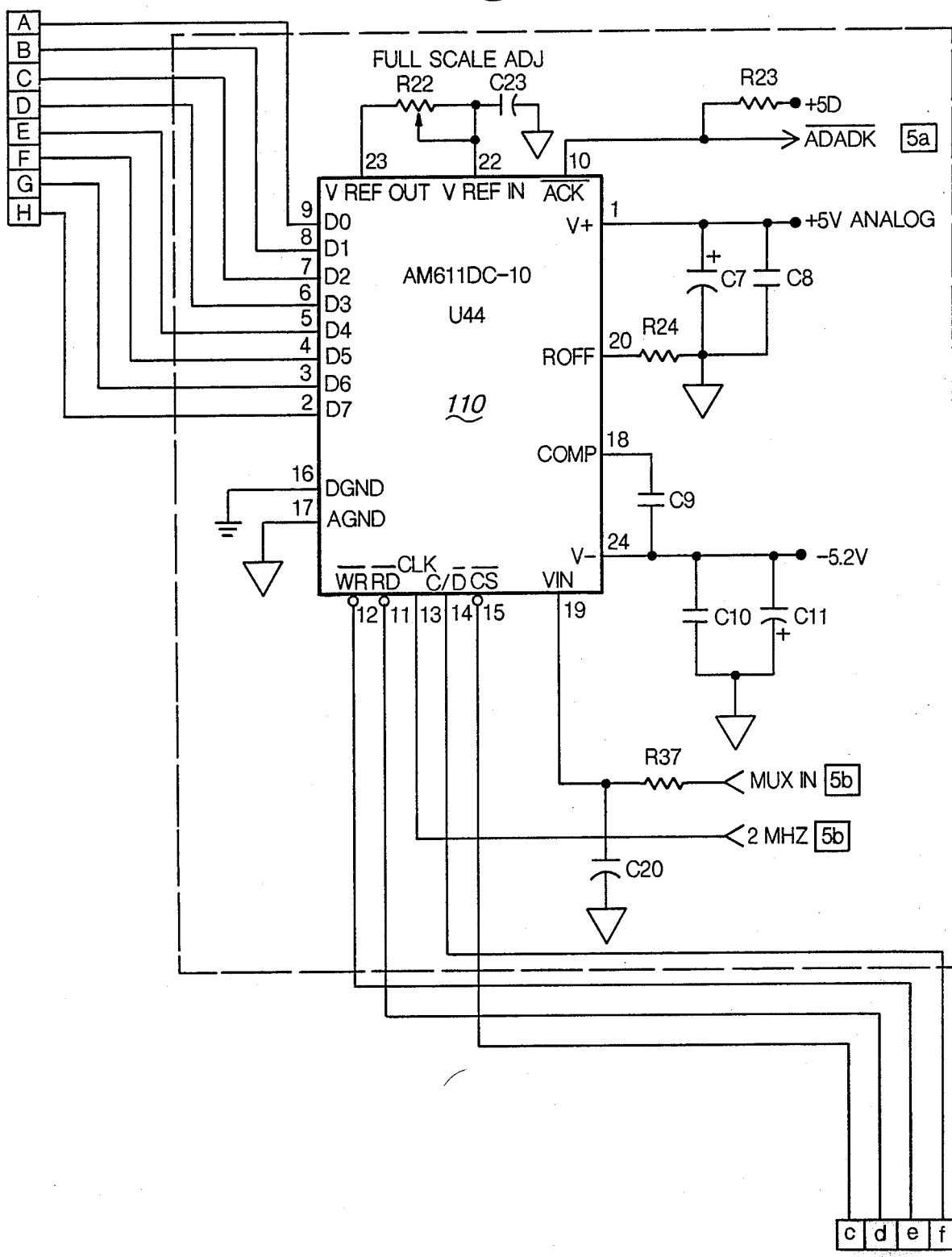
Figures 5, 5D, 6:
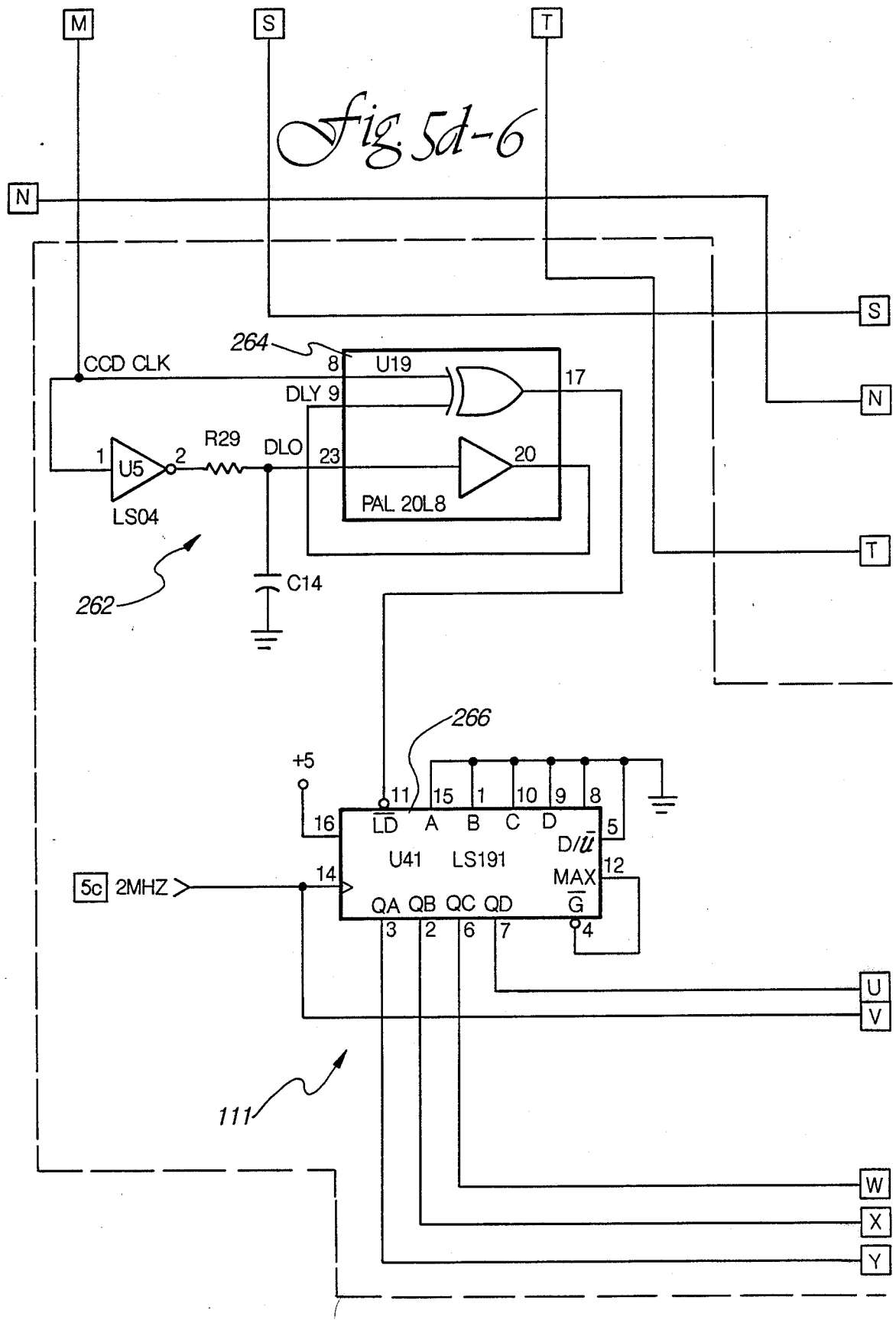
Figures 5, 5D, 6, 7:
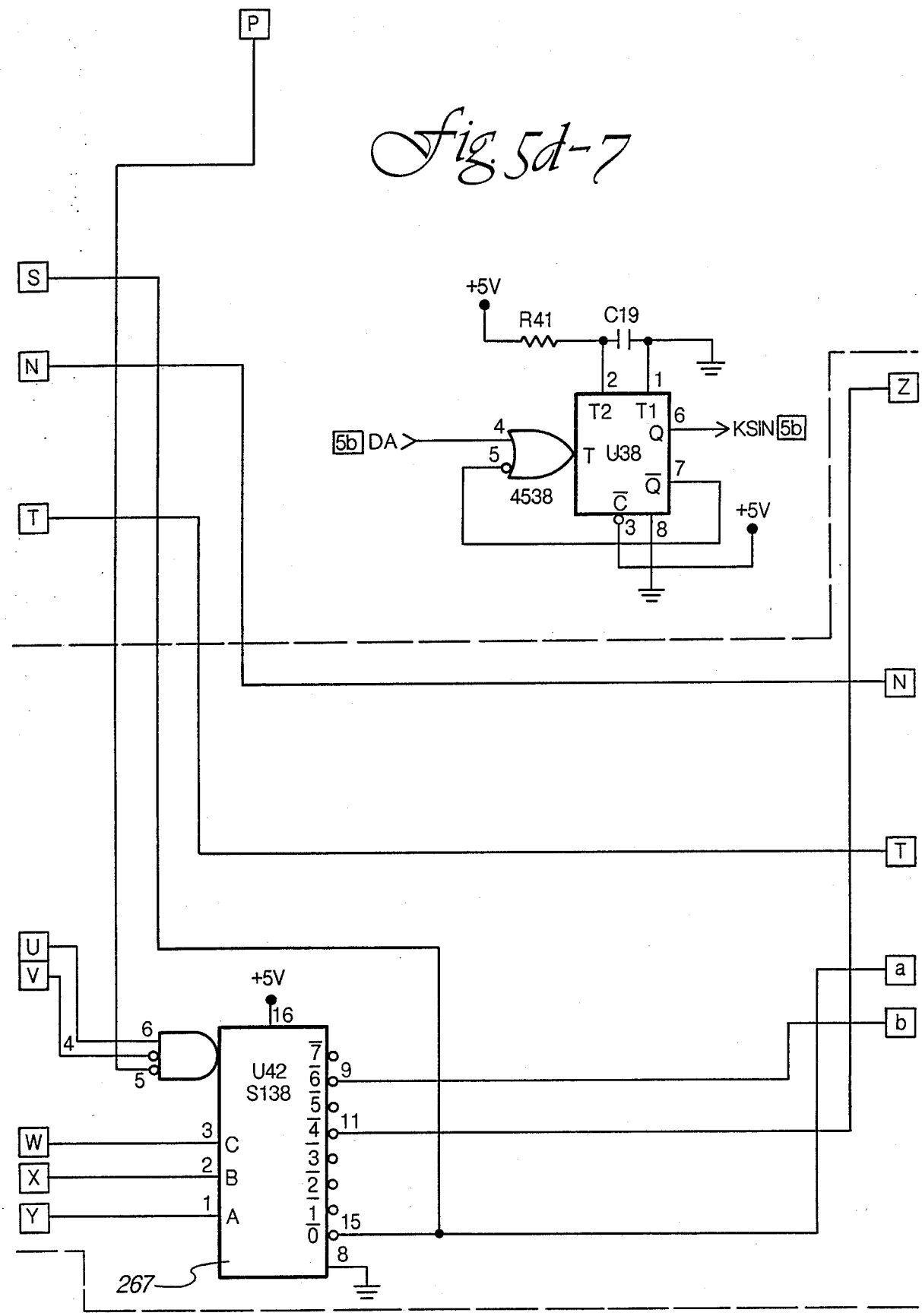
Figures 5, 5D, 6, 7, 8:
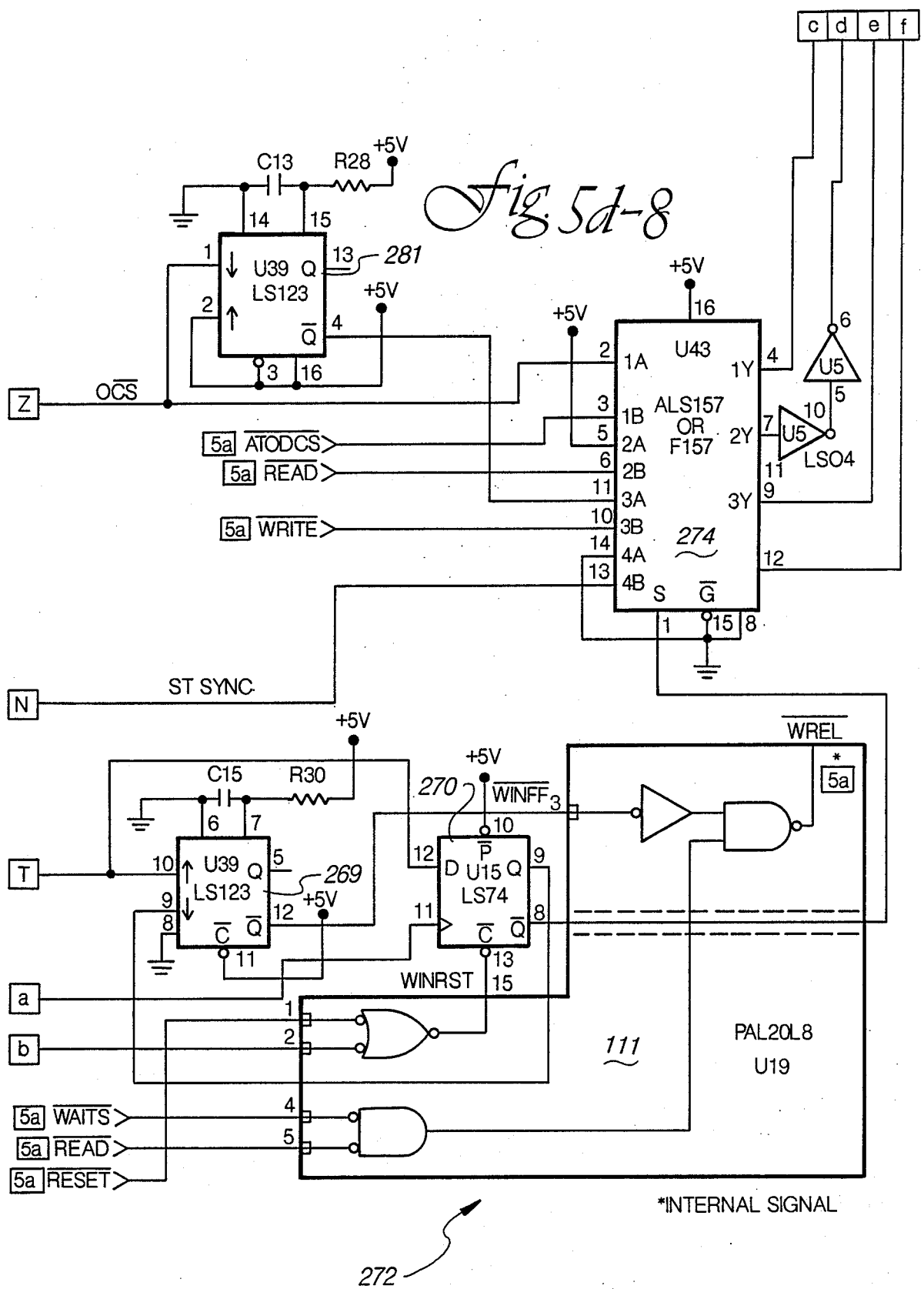

Referring now to FIG. 5d the switch inputs 106 to the parallel interface timer 241 are shown which operate in the manner discussed above.

A system timer controller 109, manufacturer's designation AM9513A, generates the clock timing needed by the cell array 44 to operate properly. It 109 also controls the steps of the stepping motor 34 which is used to move the graphic image 14 under the optical lensing system 25. The clock signal for the cell array 44, from pin 3 of the system timer controller, is connected to provide a conversion sequencer 111. This circuitry 111 is used for automatic analog-to-digital conversion for the diode array 44 voltages which is keyed off the clock signal. The operation is done in such a way that the microprocessor 101 syncs up to each conversion using the wait port. This greatly simplifies handshaking normally associated with data transfer between two devices.

As shown in FIG. 5d, the clock signal is not only connected to the cell array 44, but is also connected to a logic circuit 262 including an exclusive OR gate 264 which generates a pulse for each edge that is detected, high or low. The pulses are connected to a synchronous up/down modulo sixteen binary counter 266, manufacturer's designation LS191, a one of eight decoder/demultiplexer 267, manufacturer's designation LS138, a retriggerable monostable multivibrator 269, manufacturer's designation LS123, and a dual D-type positive edge trigger flip-flop 270, manufacturer's designation LS74 and associated logic 272. The counter 266 generates sequence control from counts 8, 12 and 14. State 8 is used to start the analog-to-digital conversion through the D-edge flip-flop 270 and through 269 generates the start signal that is connected to the analog-to-digital converter 110. When the counter 266 reaches the count of 12, it generates the timing for the analog-to-digital converter 110. When the output reaches count 14, the flip-flop 270 is cleared which releases the wait port and is connected to the microprocessor 101 so that the processor 101 can read the converted digital data. Connections to the analog-to-digital converter circuit 110 are through a quad two input multiplexer, 274, manufacturer's designation ALS157 or F157.

All analog signals that are to be sensed by the microprocessor 101 undergo conversion by the analog-to-digital circuit 110. This includes: raw dc voltage, five volt system voltage, ruler 115 input, and the output of the diode array 44. A test point is also provided where a voltage can be injected for checkout of proper operation of the analog-to-digital converter 110. The two cycles of the analog-to-digital converter 110 is the auto conversion cycle and the normal read or write cycle which takes place with the processor 101. The auto conversion is achieved with the timing discussed previously and the multiplexer 274. At the count of eight from counter 266 which is connected through the one of eight decoder 267, flip-flop 270 is set which generates a signal to the multiplexer 274 indicating that the cycle is a conversion cycle and inputs are switched to the generated timing signals at the count of twelve from counter 266. A second pulse is generated which is connected through the multiplexer 274 and becomes the select signal going to the analog-to-digital converter 110 to begin the conversion. The chip select also triggers a one shot 281 which provides a write signal to the A-to-D converter 110 which enables conversion to begin. The data which is connected from the multiplexer is the cell array 44 readings. The processor 101, in the meantime, can be performing other system tasks since a request for data to the A-to-D converter 110 is addressed to the wait port and a reading will not occur until the acknowledge is received by the multiprocessor 101.

The other circuitry shown on FIG. 5d as primarily timing circuits 111. A clock generator 284 and dividers 286, 287 generate timing to the various components of the system. The eight megahertz signal operates the central processing unit 101. The four megahertz signal is used to run interrupt circuitry and is further used for a baud rate generator. One shots 290 and 291 are used. The first takes the rectified 60 cycle power signal and converts it into a 120 cycle pulse train to indicate the condition of the line frequency for purposes of coordinating the control of the lamps 37. The second one shot 291 operates the beeper circuit for data entry and the like.

Figures 1, 5E:
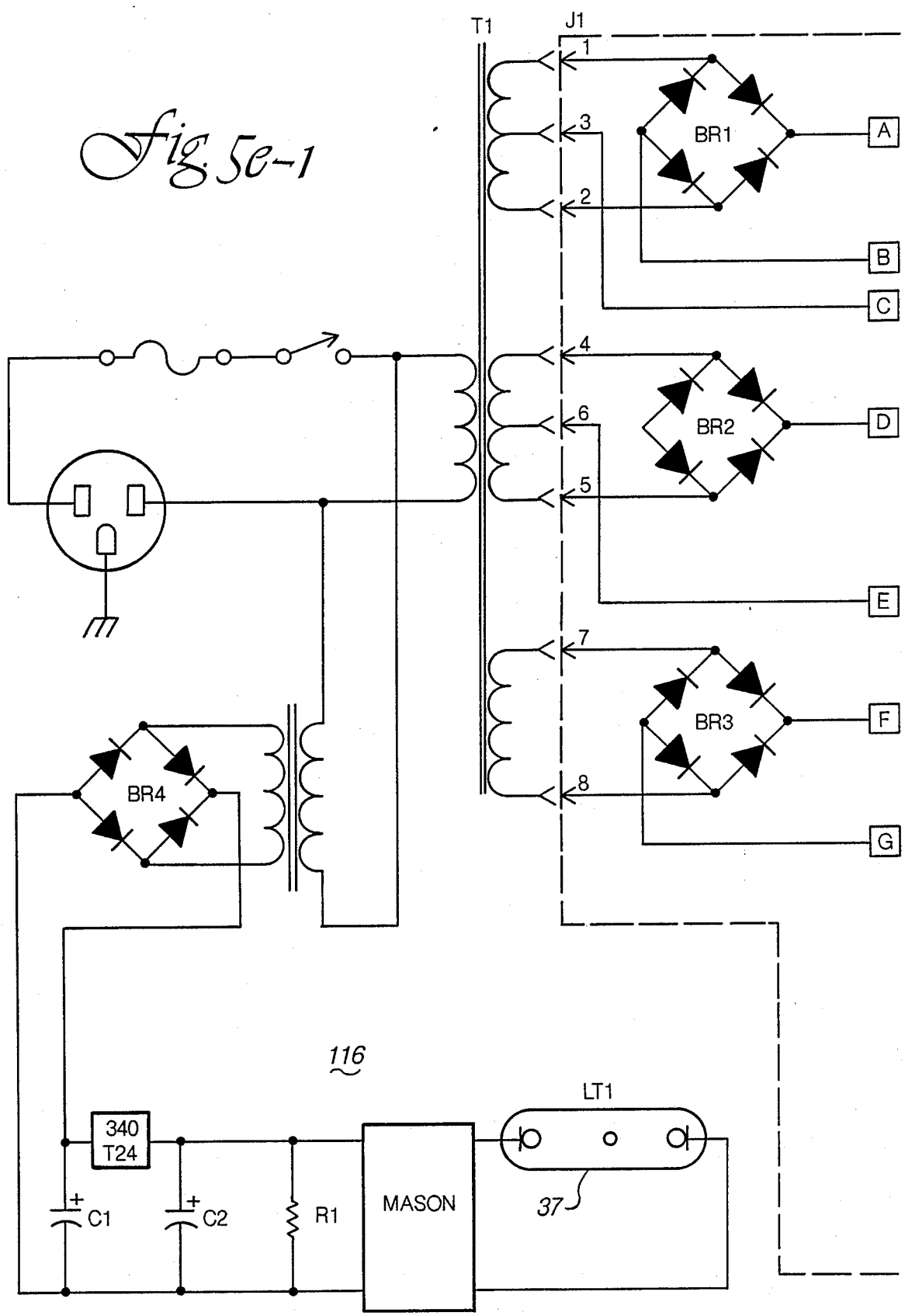
Figure 5E:
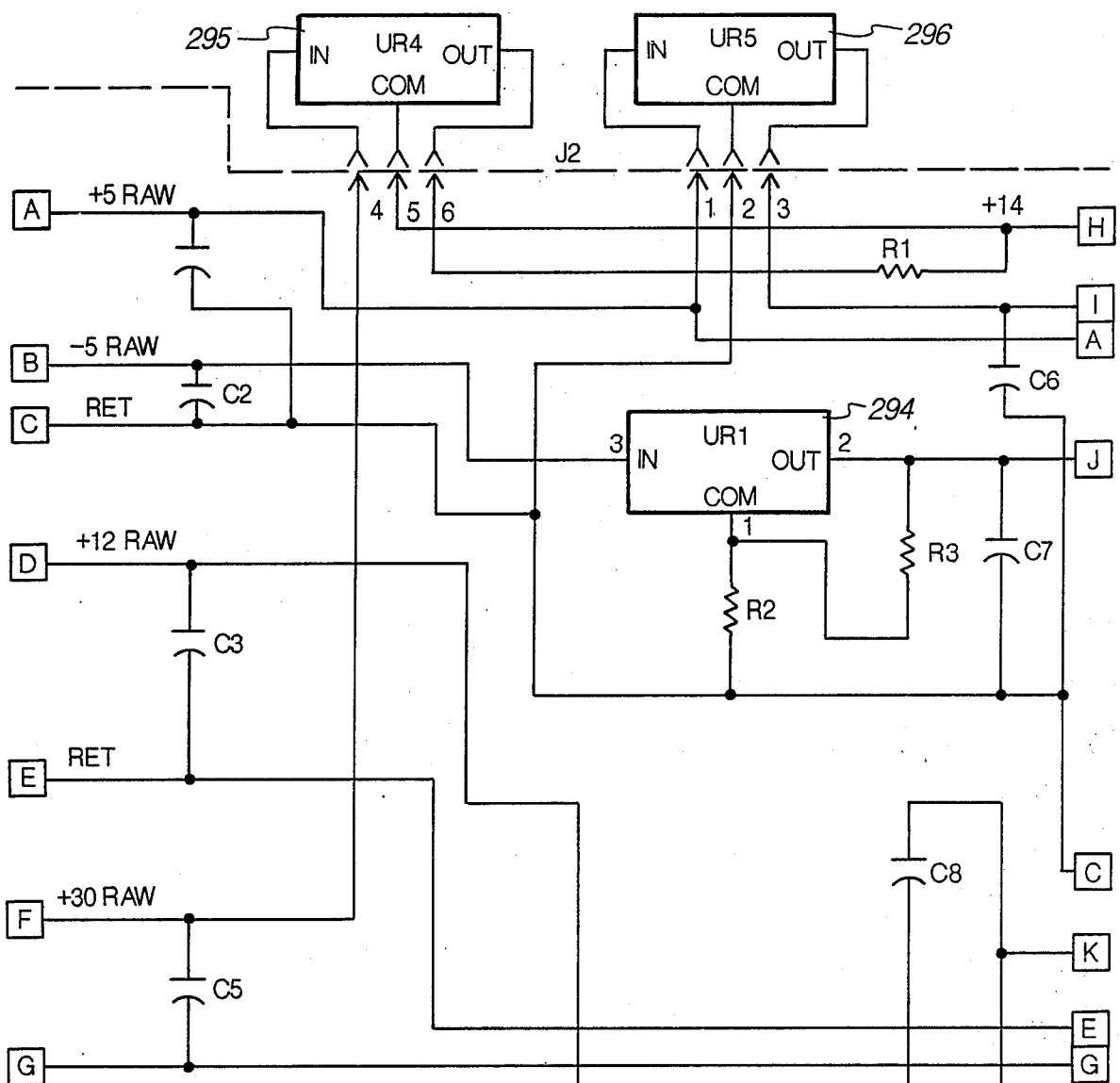
Figure 2:
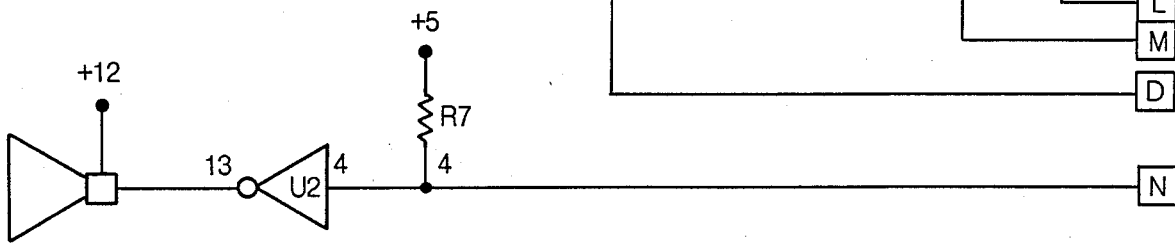
Figures 3, 5E:
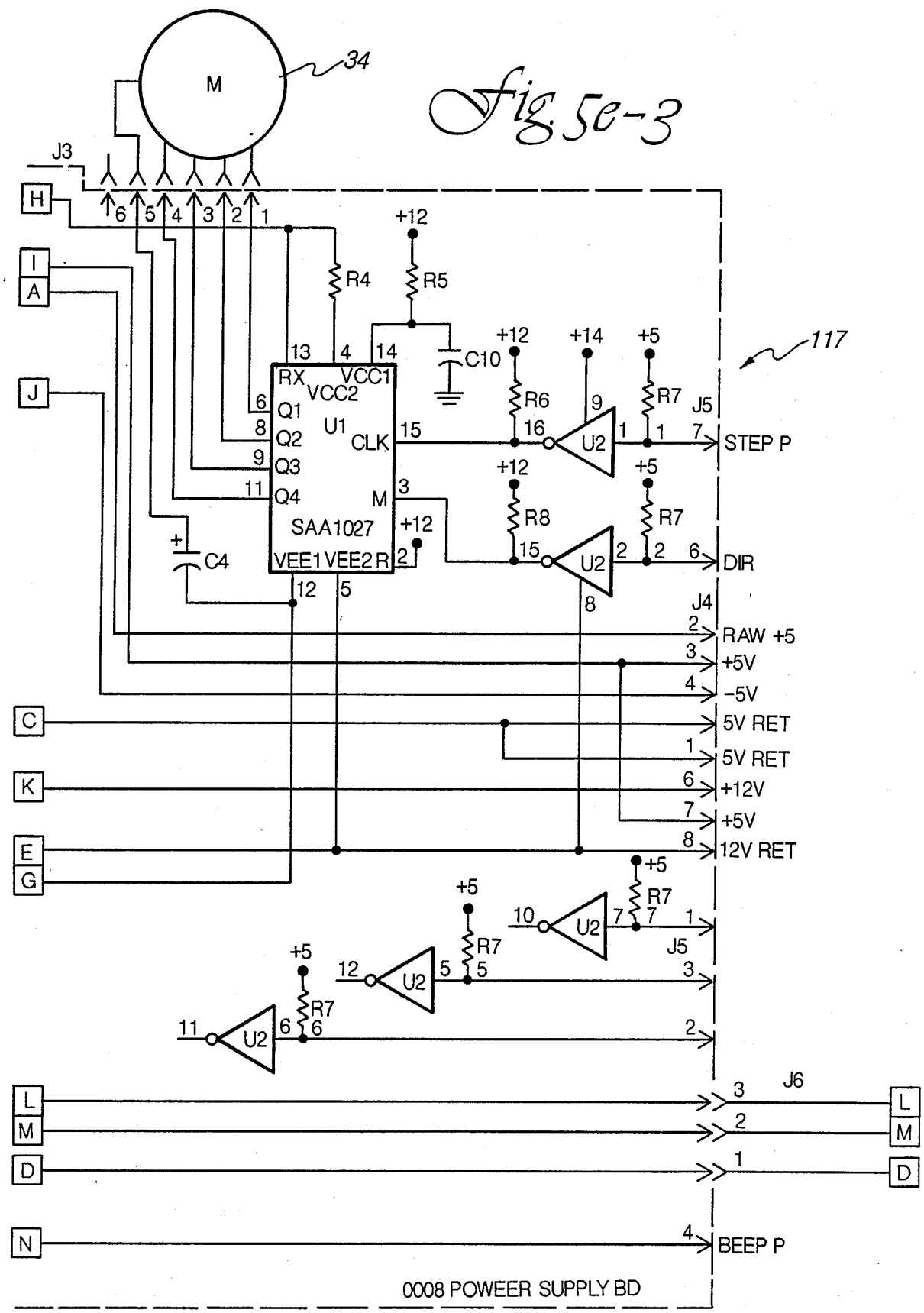
Figures 4, 5E:
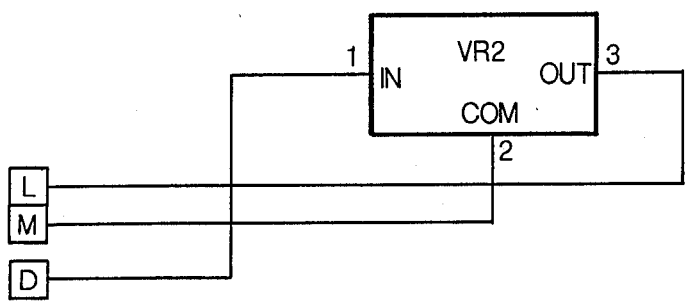

Shown in FIG. 5e is the lamp section 116 and power supply circuits 117. The lamp 37, of course, is an important part of the optical system as it must produce the same amount of light over the integration time. The components of the lamp circuit 116 control the amount of light generated so that illumination is equalized for purposes of making measurements. The power supply section 117 generates all of the operating voltages required by the system. Standard values are used so that three pin regulators 294–296 are all that is needed to control most of the voltages (plus 5, minus 5, plus 12, minus 12). The lamp 37 and motor 34 voltages are stablized for accurate scanning and repeatability.

Figure 6A:
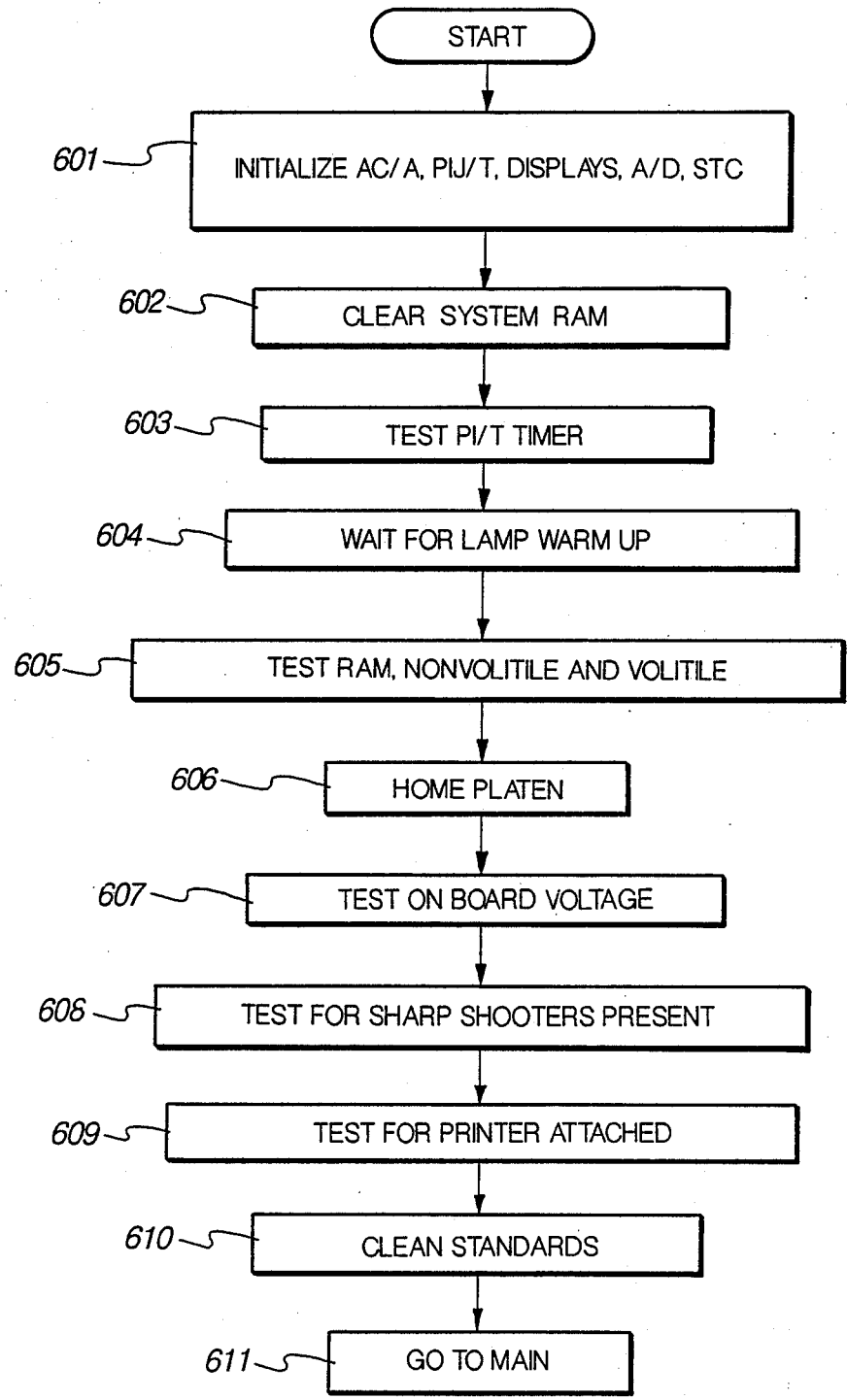
FIGS. 6a-6b represent internal operations.

Operation of the microprocessor based system is achieved through software control. Flow charts of the software used are shown in FIG. 6. Referring to FIG. 6a, when the system is turned on for the major components are initialized 601, the system memory is cleared 602, the parallel interface timer 241 is tested 603, a period of time is allowed to pass so that the lamps 37 warm up to operating voltage 604. Both the nonvolatile and volatile RAMS 102 are tested 605, the platen 16 is returned to the home position 606, onboard voltages are tested 607 and a test is made to determine whether or not exposure computers and printers are attached to the system 608, 609. Previously calculated standards are cleared 610 and operation of the software is passed 611 to the main processing loop.

Figure 6B:
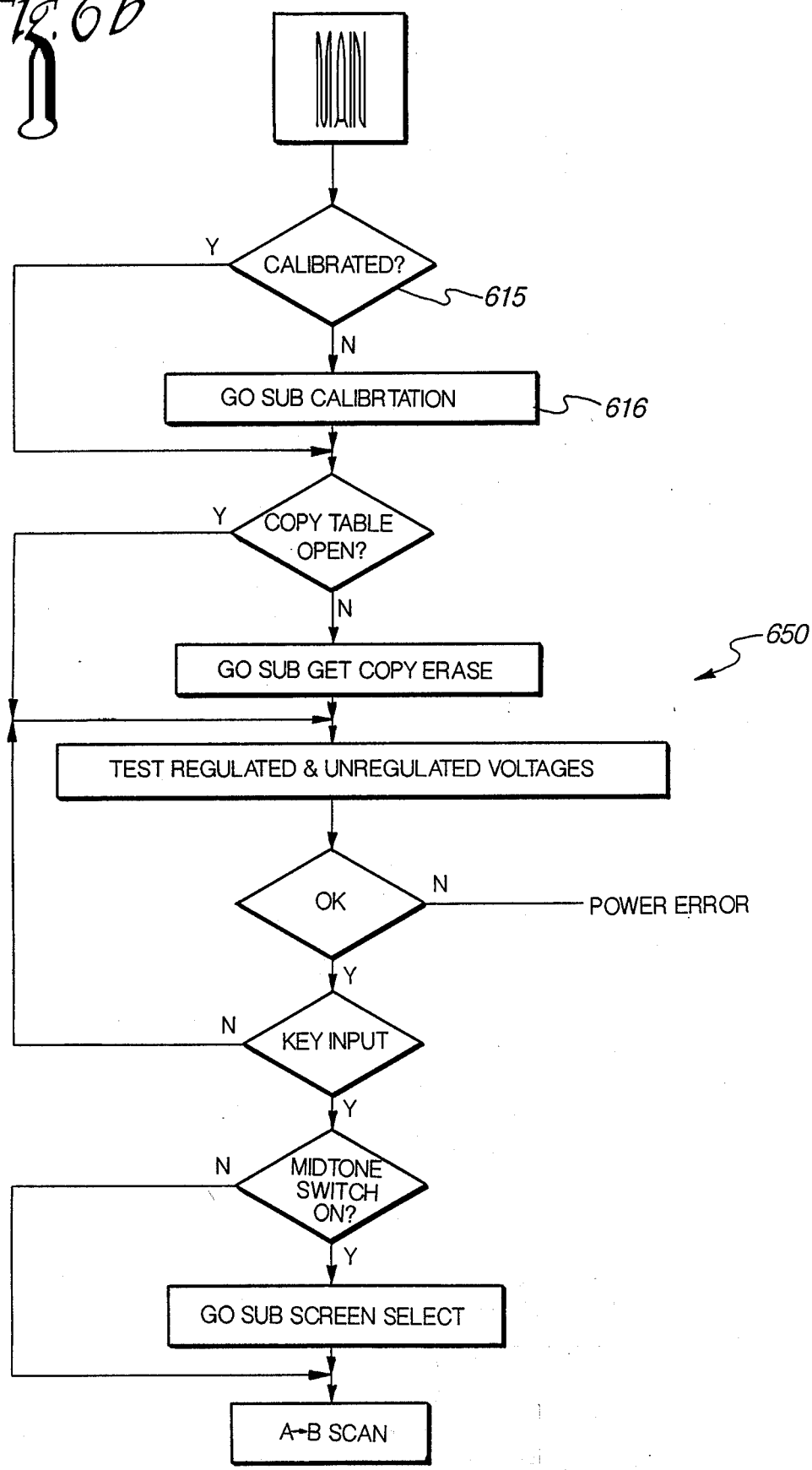

Referring to FIG. 6b, in the main processing loop shown in FIG. 6b a check is made to determine whether or not the system has been calibrated 615, if not calibrated the calibration routine 618 is run 616, as shown on FIG. 6l. Referring to FIG. 6l, the calibration routine 618 calls three additional subroutines 620–622. The calibration of the white and black standard 46, 47, shown on FIG. 6m, the calibration of the auto ruler 115, shown on FIG. 6n, and the calibration of the preferred midtone density range which is also shown on FIG. 6l.

Figure 6C:
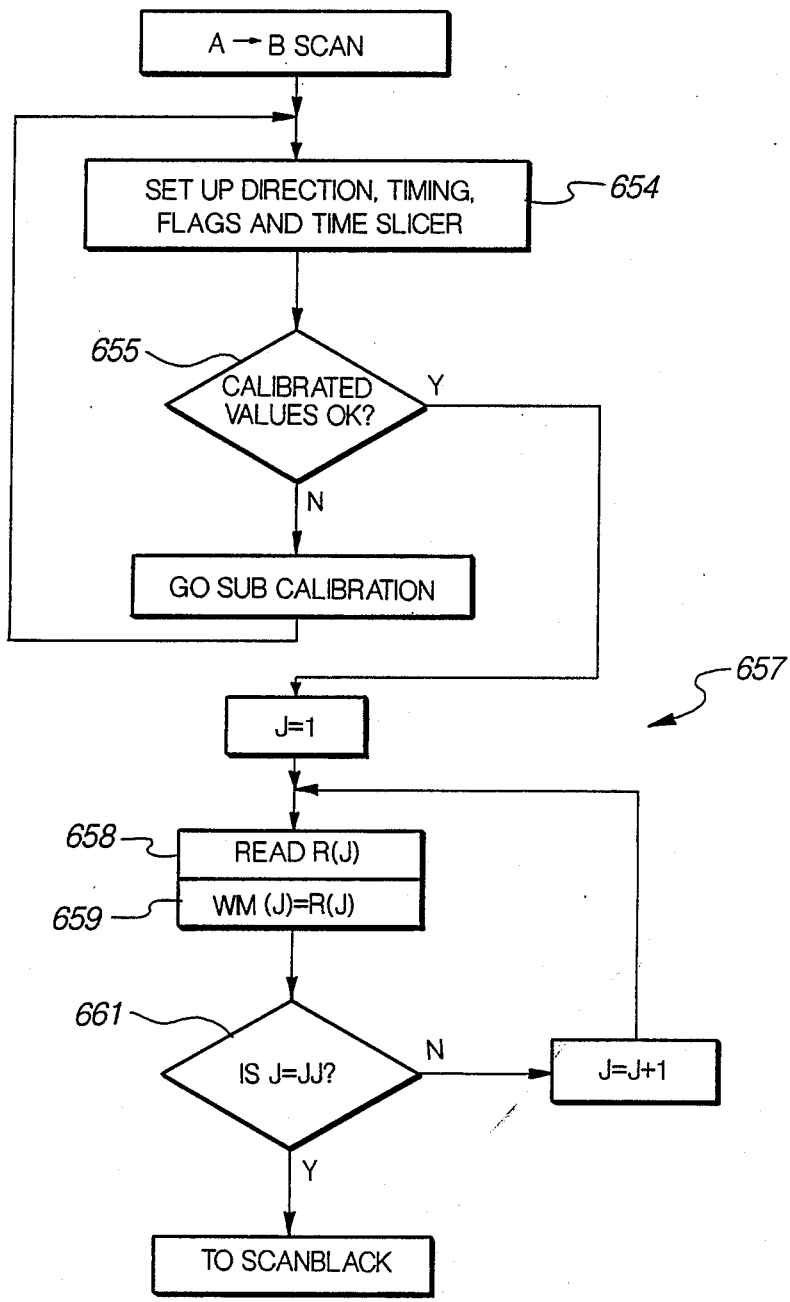
FIGS. 6k-6p represent primarily input/output operations.
Figure 6D:
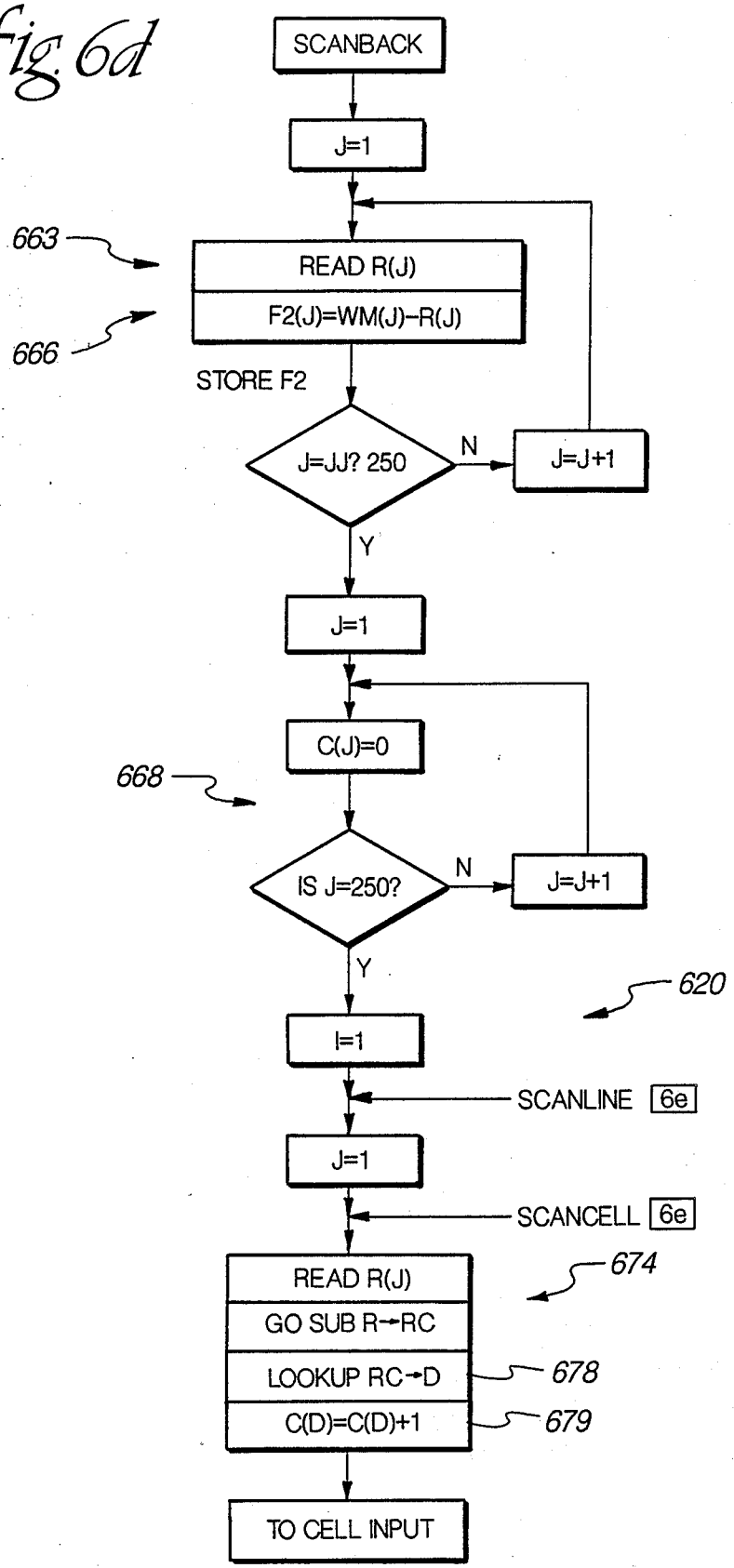
Figure 6E:
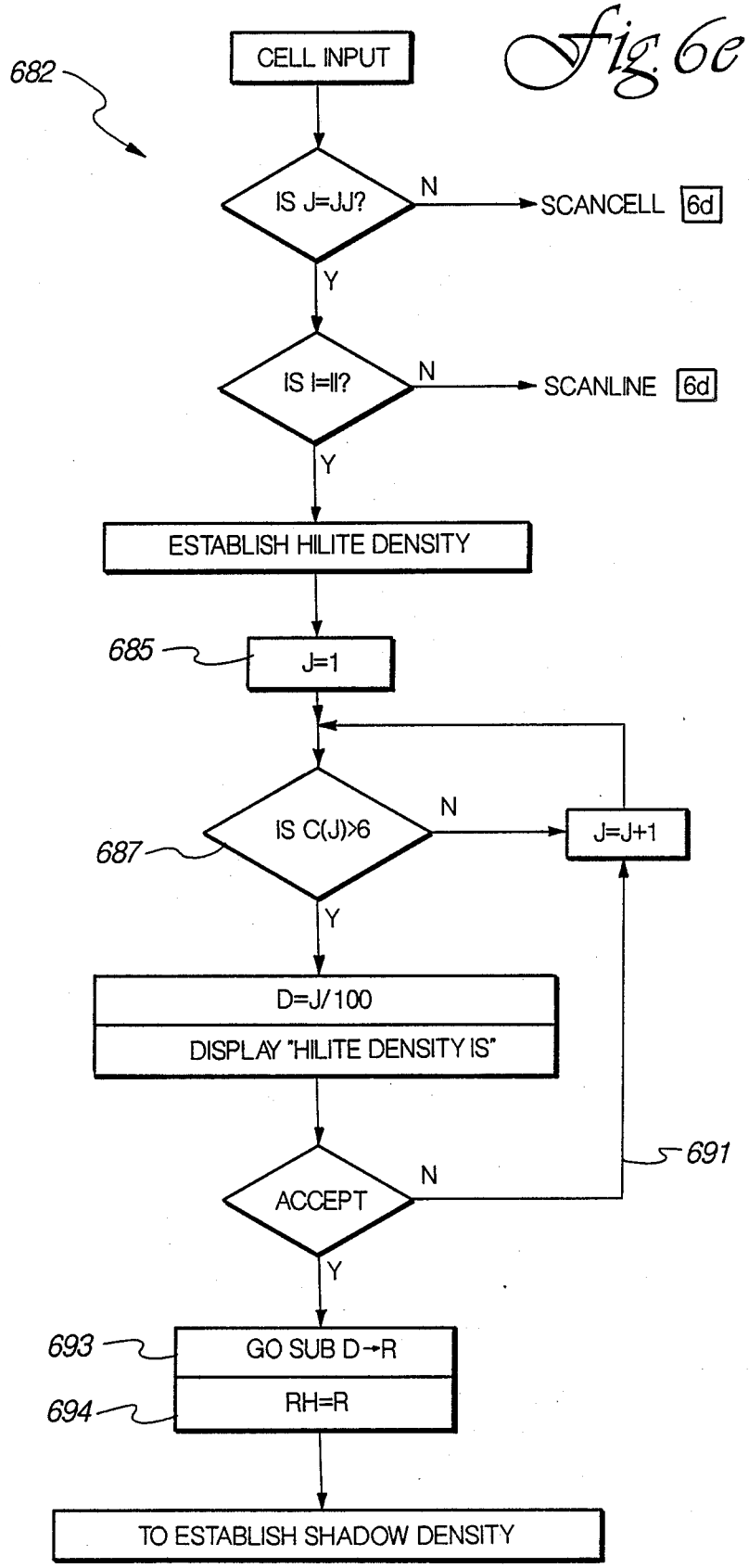
Figure 6G:
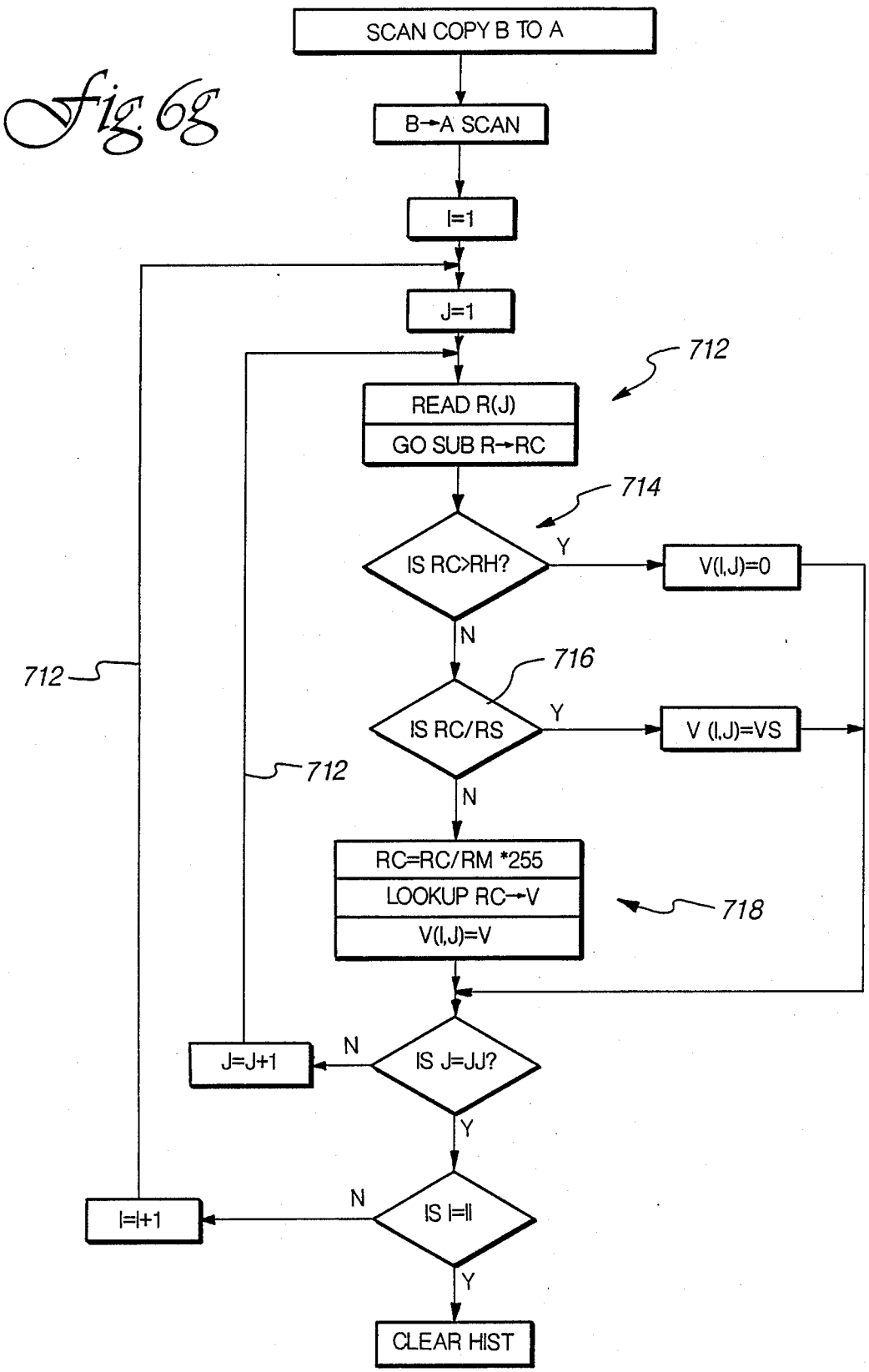
Figure 6H:
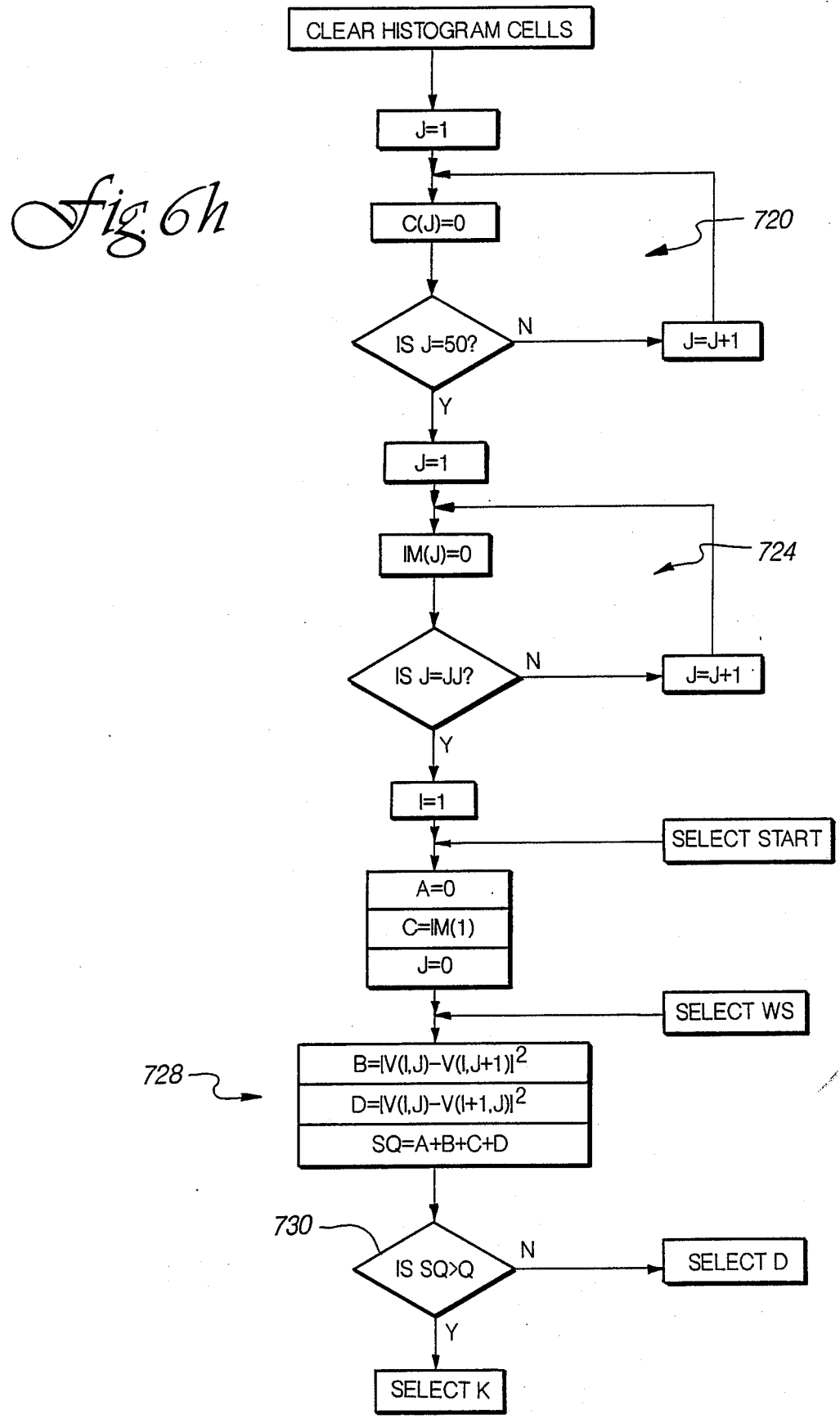
Figure 61:
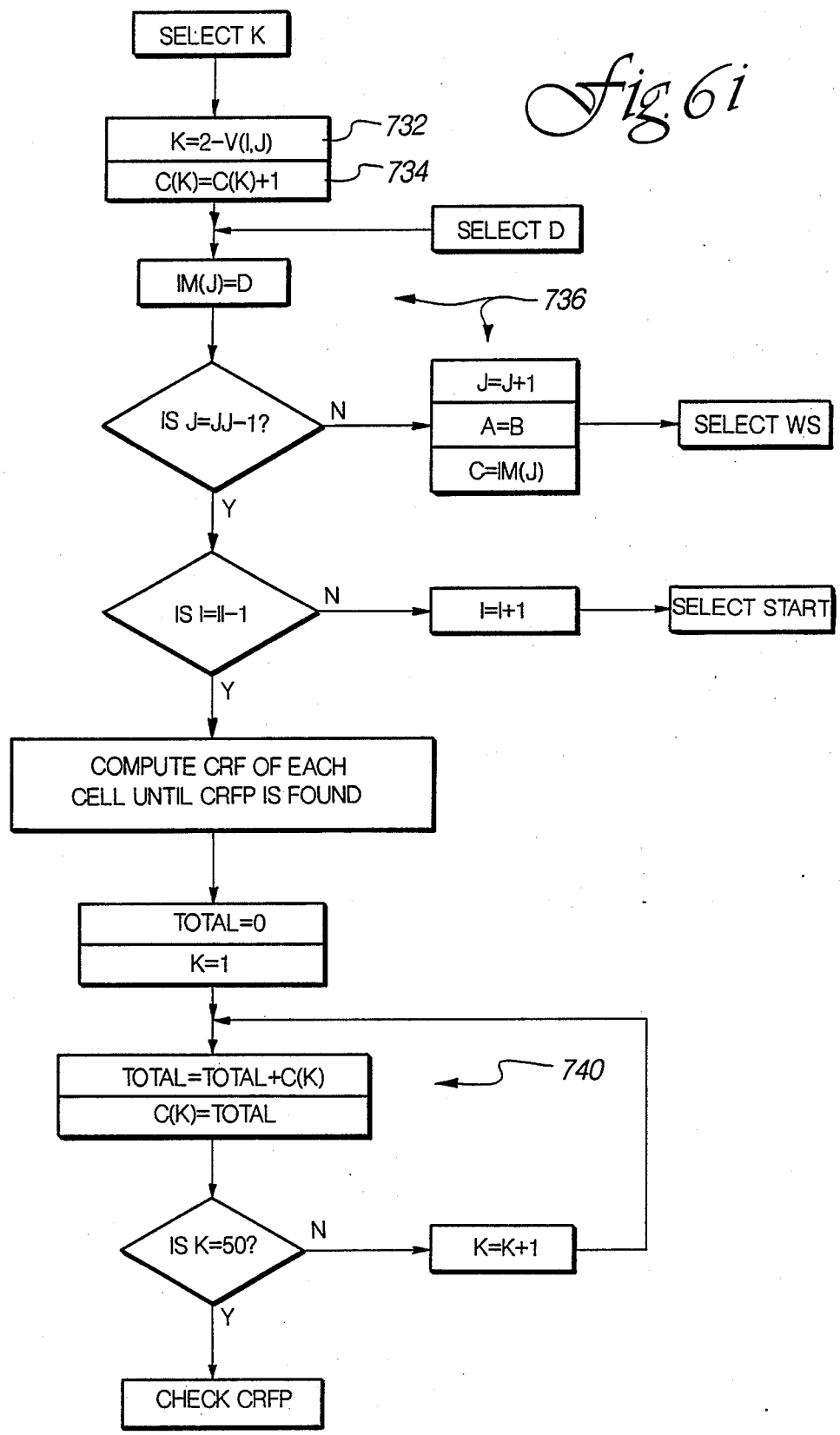
Figure 6J:
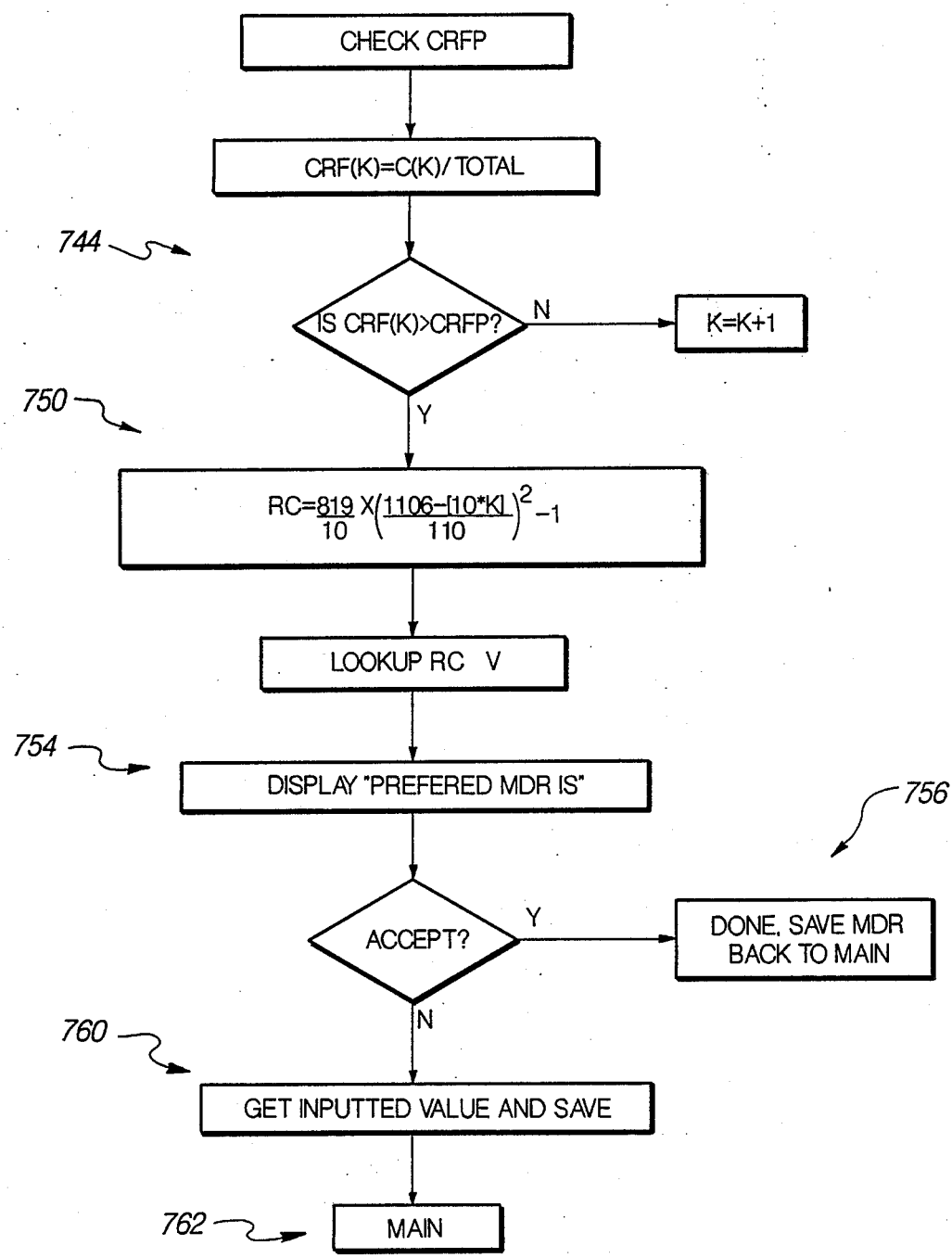
Figure 6K:
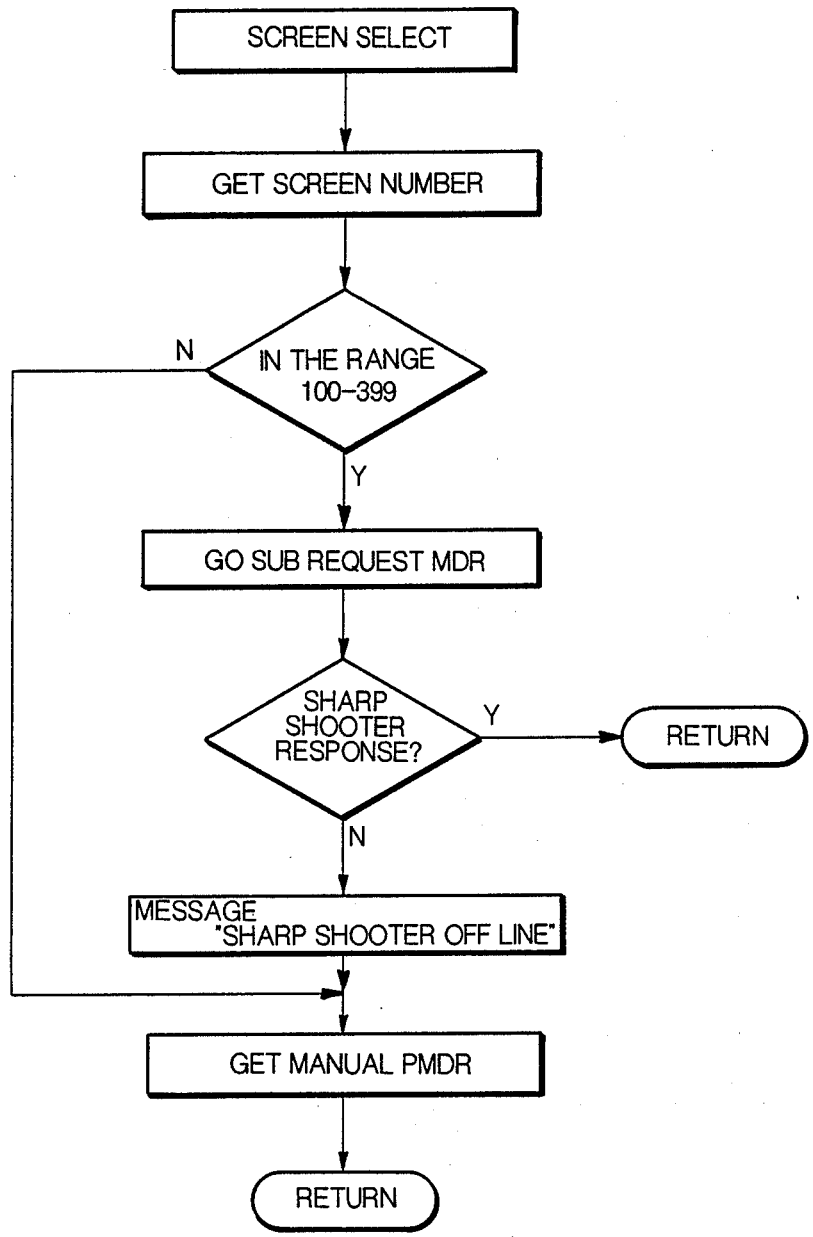

Referring now to FIG. 6m previous standards are scanned 624 and if a white standard density exists it is displayed 625. The operator can enter 626 through the keyboard 245 the density of the white bar 46, in other words an off line measurement with a regular densitometer, indicating the true density of the white bar 46. Using the mathematics 628 shown on FIG. 6p the density value is converted to reflectance 630. The variable WA (white actual) is then assigned the value of reflectance 631 calculated by the density to reflectance routine 628. A similar procedure 633 is followed for the black standard density bar 47 and a numonic F1 is calculated 635 by subtracting the black actual density value from the white actual density value.

Figure 6N:
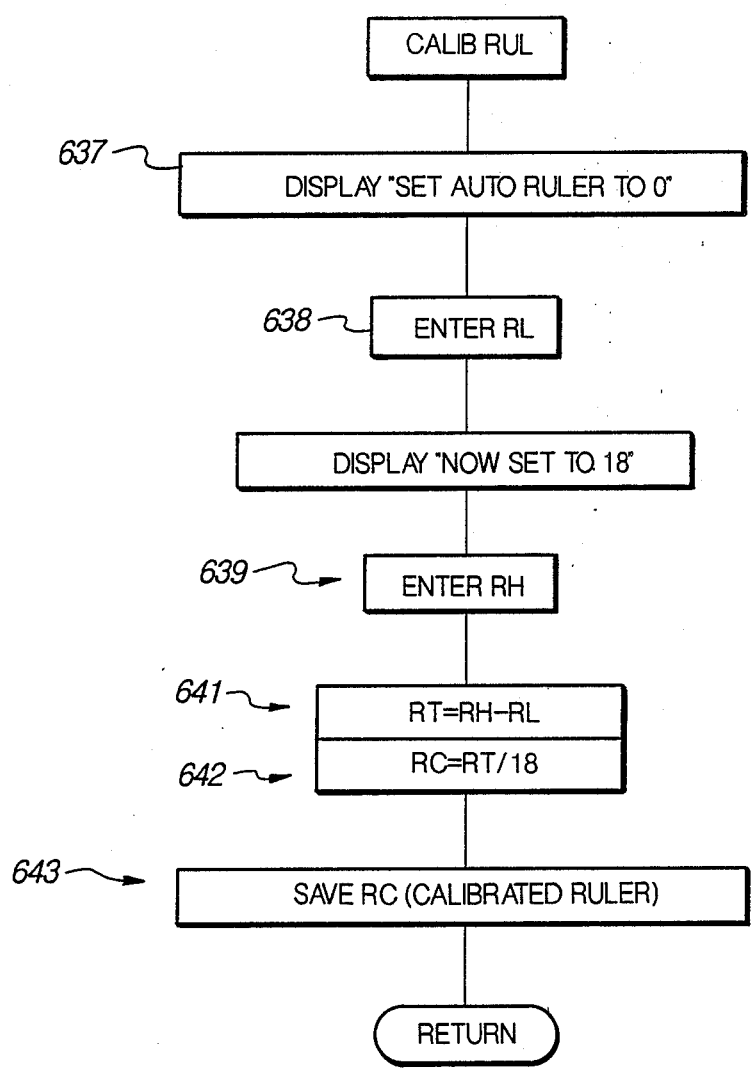
Figure 60:
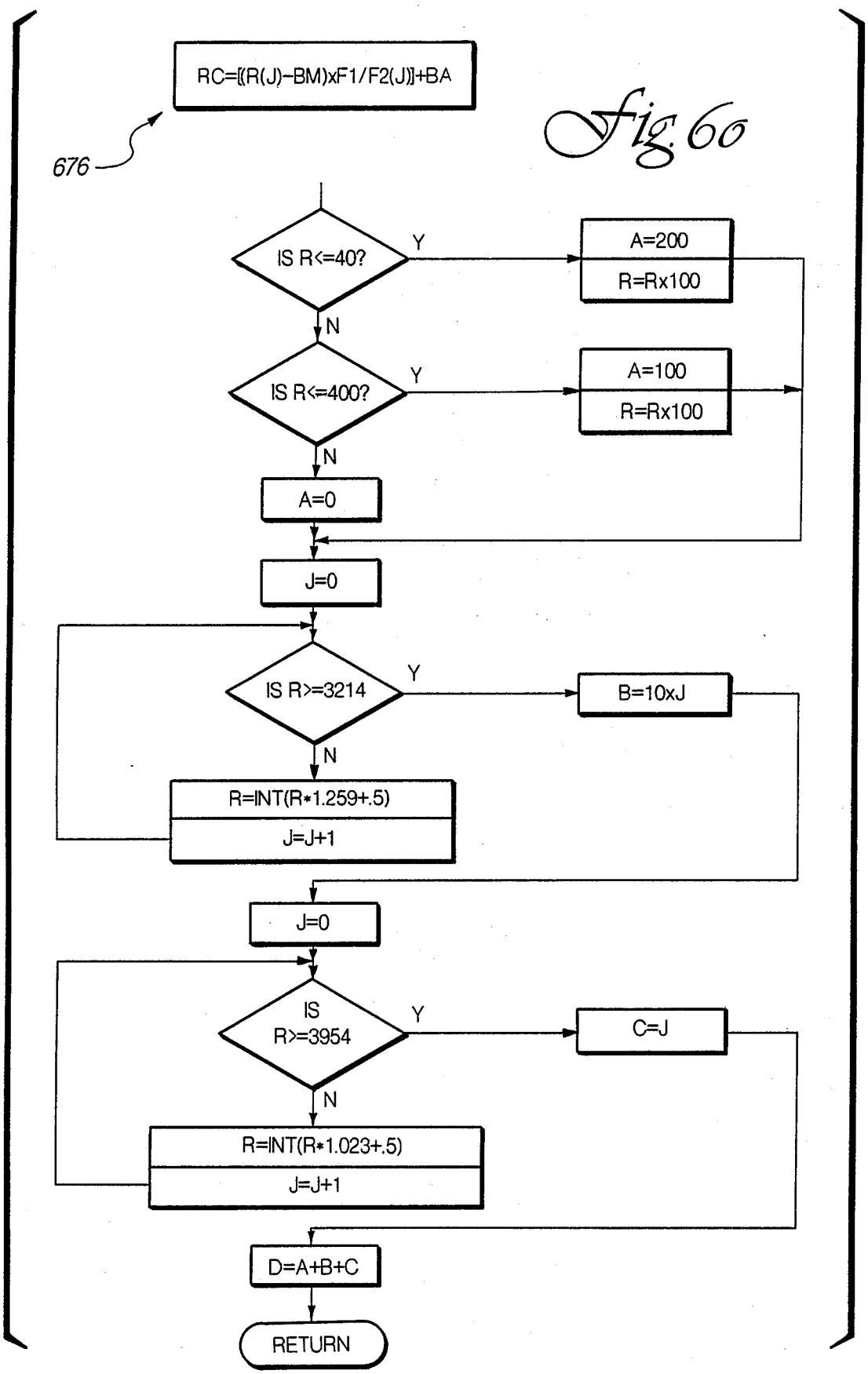
Figure 6P:
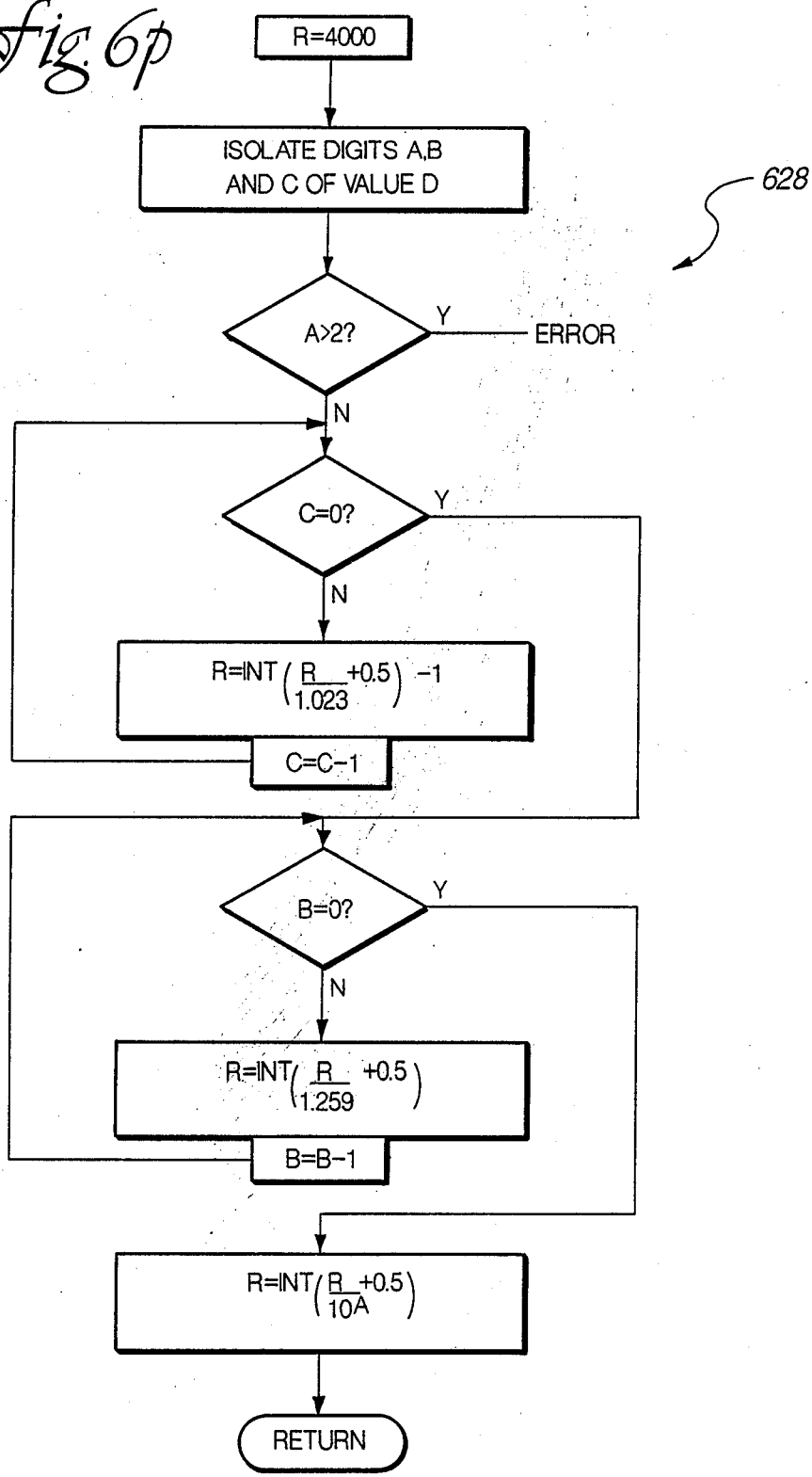

Referring to FIG. 6n, the ruler 115 is calibrated in a similar manner. The auto ruler 115 is set to the lowest reading, zero, 637 and the value RL (ruler low) is measured 638. The ruler 115 is set to the highest value (18 inches) and the high ruler reading is obtained. The total range of the ruler movement is calculated 641, followed by a calculation of the one inch value by dividing the total value by 18 inches 642 and this value is saved as RC 643 to calibrate the ruler. To calibrate the midtone density range, the operator is asked for a preferred midtone density range 645 which is entered by the operator 647. This value is one that is suitable for the printing conditions that are going to be used for printing the half tone reproduction and it is the density range that would be wanted for normal copy, that is copy with normal characteristics which are not high key or low key.

After other system checks 650 shown on FIG. 6b, a scan of the copy can be initiated.

It will be understood by those skilled in the art that while two scans of the copy are described in connection with the preferred embodiment of the invention, all data collected during a single scan could also be utilized to achieve the same results.

The first scan of the copy 14 is in what is referred to as the A to B direction. In a preferred embodiment this creates a histogram of the densities in the copy 14. In other words, the density measured at each cell site (J) in each line (I) of the copy 14 is corrected for nonuniformity of the cell, flare and the like and that value is stored in a memory location corresponding to the density value. Once the frequency of occurrence of the various densities throughout the copy 14 has been determined, the highlight density of the copy 14 and the shadow of the copy 14 can be easily determined and varied using the pinch key.

Referring to FIG. 6c, the direction of travel of the platen 14, the timing flags and the like are setup 654 and calibration is rechecked 655.

The scan of the white bar 46 is a single scan 657 through all the diode cell sites (J through JJ) in the diode array 114.

A reading 658 is taken from each cell in the cell array. The reflectance of each cell reading is determined and stored as WM(J) the white measured reflectance of the standard 659. When all cells have been read, J equals JJ 661, the black bar 47 is similarly scanned 663 as shown on FIG. 6d. For each cell, a factor F2 is calculated 666 which is equal to the white measured J, the measurement of the white bar 46, minus the measurement of the reflectance of the black bar 47.

As shown in FIG. 6d all density cells of the histogram are cleared or set to zero before scanning of the actual copy begins 668. When scanning copy, I refers to the rows of the copy and J refers to the cell sites of the array 114. Both the row (I) and cell site (J) are initialized to one 670 and readings from the capacitive cell array 114 begin.

The diode input R (J) is read for each cell location 672 and this is converted to a corrected reflection (RC) 674, using the formula 676 identified on FIG. 6a, which corrects the measurement according to the factors F1, F2 calculated previously. This is converted to a density 678 and the memory location assigned that density in the histogram is incremented. Memory locations can be established for each 0.01 increment of density and the memory location incremented by one every time a measurement of density occurs. For example, if a measured density of 1.8 is obtained, a memory location 180 (corresponding to 1.8) is incremented by one each time that measurement occurs. This produces the frequency histogram of density necessary to establish the density range of the copy. This process continues for all cell sites and all rows of the copy 682, as shown on FIG. 6e.

After the histogram of the various densities of the copy 14 has been created, the highlight and shadow densities of the copy are determined as shown on FIGS. 6e and 6f. Referring to FIG. 6e, the histogram is then reviewed by setting J equal to one 685 for the first memory location of the histogram which corresponds to the lowest density (highlight). Each sequential memory location is reviewed until one is located which has a plurality of accumulations of density measurements 687. This is targeted as the highlight density. A plurality of hits is required to avoid extraneous effects on the data such as a speck of dust or other nonconformity in the surface of the copy 14. If the value is too high for the operator's acceptance, the operator hits the pinch key on the keyboard 245 and the software jumps 691 to the next cluster of densities having the preselected number 4, 6 or the like, of measured densities. When the selected density is chosen, it is converted back to reflectance 693 and stored 694 as the value RH, reflectance of highlight.

Referring now to FIG. 6f, this same procedure is followed 696 to indicate the chosen shadow density which is again converted to reflectance 698 and is stored 699 as RS, reflectance of shadow.

The reflectance ratio of the highlight to shadow density is converted to darkness 702 and saved 705 as a variable V. V is also used to compute 707 a constant called Q which is the threshold of acceptance or rejection and referred to as the "informational" acceptance limit of the copy 14. This value is used in the calculation of the midtone density range which will be explained below.

During the return scan pixels are analyzed in groups of four rather than cell by cell and line by line in the high resolution scan of the initial A to B scan. The midtone determination attempts to determine the general tones throughout the copy. All values from the B to A scan are kept in the condensed form.

After the data is gathered, each density is compared with adjacent densities (i.e. adjacent in terms of measurement location) to determine if the measurent represents an informational measurement. Non-informational measurements are those areas in the original which are uniform, e.g. a uniform background area. This can be represented as follows:

$$\begin{array}{c} C \\ V(I-1, J) \\ AV(I, J-1)V(I, J)V(I, J+1)B \\ V(I+1, J) \\ D \end{array}$$

$$A = \{V(I, J) - V(I, J-1)\}^2$$
$$B = \{V(I, J) - V(I, J+1)\}^2$$
$$C = \{V(I, I) - V(I-1, J)\}^2$$
$$D = \{V(I, J) - V(I+1, J)\}^2$$

V(I,J) is the object of acceptance or rejection. SQ =A+B+C+D. V(I,J) is rejected if "SQ" exceeds "Q".

Non-informational measurements are discarded. The frequency of informational measurements are accumulated in memory "cells" according to their value. Each cell has a specified density range. For example:

| Cell # | Density Range |
|---|---|
| 1 | 0.0 to 0.08 |
| 2 | .09 to .16 |
| 3 | .17 to .24 |
| etc. | |
| 50 | 3.93 to 4.00 |

For each measurement a cell number is identified according to the valve of the measurement. A value of "1" is then added to that cell. The "Absolute Frequency" of occurrence is thus accumulated for each specified density range.

The Absolute Frequencies thus accumulated are then converted to Cumulative Frequency and then to Cumulative Relative Frequency. The latter is determined by dividing Cumulative Frequencies by the overall total frequency.

| Cell | Cell Midpoint | Absolute Frequency | Cumulative Frequency | Cumulative Relative Frequency |
|---|---|---|---|---|
| 1 | 0.04 | 10 | 10 | 0.01 |
| 2 | 0.12 | 20 | 30 | 0.03 |
| 3 | 0.2 | 20 | 50 | 0.05 |
| . | . | . | . | . |
| . | . | . | . | . |
| 50 | 4.0 | 5 | 1000 | 1.00 |

When the Cumulative Relative Frequency reaches the value "K", the preferred midtone density range has been determined. As those skilled in the art will realize, a similar procedure can be followed to determine proper placement of the 25% dot, the 50% dot and the 75% dot for black and white and color work.

Referring now to FIGS. 6g and 6j, readings are taken 712 of all areas of the copy 14. For values of measured reflectance (RC) which are greater than the reflectance of the selected highlight, the values are set to the highlight value 714. Values measured for the copy (RC) which are less than the reflectance of the selected shadow density RS are set to the value of the shadow density 716. Since all values are converted to darkness values (V) 718 a map is created in memory which indicates the darkness of the copy corresponding to the density range of the copy.

A second set of memory locations are cleared 720 for the histogram which will indicate the cumulative relative frequency of the copy. In doing so, the first line array is cleared 724 and the pixels are analyzed in the groups of five to determine informational areas. The center cell of each group is analyzed and the difference calculated between the darkness of the center cell and the cells to right, the left, the cell above and the cell below. Using the formulas 728 shown on FIG. 6h, and discussed above, the squares of the differences are calculated and sum of the squares is obtained (SQ). If the sum of the squares is greater than the factor Q calculated earlier 730, the pixel is "informational" and K is calculated as shown on FIG. 6i.

Q represents the range of the copy. For short range copy, little difference between highlight and shadow, Q will be small and less values will be thrown out because the range is less. In short range copy what appears to be an insignificant difference becomes more and more significant as the copy becomes compressed.

To calculate K the darkness value is multiplied by two 732 and the appropriate memory location is incremented 734. K ranges from zero to 50 and is stored in the histogram to determine cumulative relative frequency. Reusable values are stored 736 for use in the next calculation.

To find the cumulative relative frequency of each cell, the total values of each cell are added to obtain C (K) total 740. The cumulative relative frequency of each cell is then found by dividing each value by the total value to create percentages of the total 744 which by definition is the cumulative relative frequency. When that calculation indicates that the cumulative relative frequency preferred has been located, the recommended midtone range can be calculated 750 as shown on FIG. 6i. This is equal to the midpoint, the 50 percent location for the midtone dot. The midtone range is then calculated and displayed 754. If the operator selects the analyzed value it is saved 756 and the program returns to the main processing routine. If the operator rejects the value, the preferred midtone range earlier entered by the operator into the keyboard is selected or any other value entered 760 and the main processing loop is again accessed 762.

In the foregoing manner, all values necessary for a reproduction of original copy are obtained and can be printed out on the printer attached to the system. The automation provided in the foregoing hardware and software automatically and rapidly produces everything necessary for the operator to reproduce the copy with precisely selected highlight and shadow density values and a midtone range which enhances the reproduction of the copy. The reproduction size is also easily chosen with the system. While many and varied changes can be made to the system described upon review of the disclosure by those skilled in the art, each and every such modification that falls within the scope of the appended claims is within the intendment of the invention.

We claim:

1. An apparatus for automatically determining the densities of a graphic image having highlight, shadow and intermediate densities comprising:

a support means for supporting the graphic image;

a light source positioned to direct light on or through the graphic image;

a scanning head positioned adjacent the support means to measure the highlight, shadow and intermediate densities, the scanning head comprising:

a plurality of light sensitive elements positioned to detect the amount of light from the graphic image and thereby to provide data relating to the density of the graphic image; and means for focusing the light on the plurality of light sensitive elements;

automated means for causing relative scanning movement between the scanning head and the graphic image for at least two scans, one of which measures highlight and shadow densities and another of which determines the intermediate densities;

means for calibrating the plurality of light sensitive elements;

means for correcting the data from each light sensitive element according to the calibration; and means for processing the corrected data from each of the light sensitive elements to determine the highlight and shadow densities of the graphic image and the intermediate densities of graphic image.

2. The apparatus of claim 1 wherein the first scan of said two scans measures said highlight and shadow densities and the second scan of said two scans determines the intermediate densities.

3. The apparatus of claim 2 wherein the first scan is a high resolution scan and wherein the second scan is a low resolution scan.

4. The apparatus of claim 2 wherein both the first scan and the second scan are performed at the same resolution.

5. The apparatus of claim 2 wherein the second scan sequentially measures intermediate densities and wherein the processing means excludes redundant densities measured during the second scan so that the background in the graphic image is disregarded for purposes of analysis.

6. The apparatus of claim 1 wherein the plurality of light sensitive elements comprise a monolithic array of photosensitive cells.

7. The apparatus of claim 6 wherein each cell detects the density of a one millimeter portion of the graphic image.

8. The apparatus of claim 7 wherein the array of cells comprises a plurality of cells positioned adjacent one another and wherein the density detected by any cell is compared with adjacent cells to provide a three millimeter aperture.

9. The apparatus of claim 7 wherein the focusing means is adjustable to vary the portion of the graphic image detected by each cell of the cell array.

10. The apparatus of claim 6 wherein the monolithic array comprises multiplexed photodiodes.

11. The apparatus of claim 6 wherein the monolithic array comprises charged coupled cells.

12. The apparatus of claim 6 wherein the monolithic array comprises charged coupled photodiodes.

13. The apparatus of claim 12 wherein the frequency of occurrence of all densities are stored in the memory.

14. The apparatus of claim 1 wherein the processing means comprises means for calculating the preferred intermediate density range for reproduction of the graphic image.

15. The apparatus of claim 1 wherein the processing means comprises means for calculating the absolute frequency of occurrence of densities within pre-selected density ranges.

16. The apparatus of claim 15 wherein the processing means comprises means for calculating the cummulative frequency of occurrence for increasing or decreasing density values.

17. The apparatus of claim 16 wherein the processing means comprises means for calculating the cummulative relative frequency of occurrence for increasing or decreasing densities.

18. The apparatus of claim 1 wherein the scanning means comprises means for causing a first scan in a first direction to measure highlight and shadow densities and a return scan in the opposite direction to determine the intermediate densities.

19. The apparatus of claim 1 wherein the means for calibrating the plurality of light sensitive elements comprises means for calibrating the light sensitive elements for thermal noise generated in the light sensitive elements.

* * * * *